(12) United States Patent
Zangar et al.

(10) Patent No.: US 8,822,164 B2
(45) Date of Patent: Sep. 2, 2014

(54) BIOMARKERS FOR LYMPHOMA

(71) Applicant: Battelle Memorial Institute, Richland, WA (US)

(72) Inventors: Richard C. Zangar, Richland, WA (US); Susan M. Varnum, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 13/690,073

(22) Filed: Nov. 30, 2012

(65) Prior Publication Data

US 2013/0137595 A1 May 30, 2013

Related U.S. Application Data

(60) Provisional application No. 61/565,036, filed on Nov. 30, 2011.

(51) Int. Cl.
| | | |
|---|---|---|
| *G01N 33/68* | (2006.01) | |
| *G01N 33/53* | (2006.01) | |
| *G01N 33/574* | (2006.01) | |
| *C40B 30/04* | (2006.01) | |

(52) U.S. Cl.
CPC ...... *G01N 33/6893* (2013.01); *G01N 33/57407* (2013.01); *G01N 2333/70539* (2013.01); *G01N 33/6848* (2013.01); *G01N 33/57488* (2013.01); *G01N 2333/904* (2013.01); *G01N 2333/4737* (2013.01); *G01N 33/57426* (2013.01)
USPC .................. 435/7.1; 435/7.23; 435/23; 506/9

(58) Field of Classification Search
CPC . G01N 33/53; G01N 33/574; G01N 33/6848; G01N 2458/15; C12Q 1/37; C40B 30/04
USPC .................. 435/7.1, 7.23, 23; 436/501; 506/9
See application file for complete search history.

(56) References Cited

U.S. PATENT DOCUMENTS

2005/0277131 A1* 12/2005 Jaffrey ............................. 435/6
2007/0249000 A1 10/2007 Tuse et al.
2011/0257890 A1 10/2011 Weinschenk et al.

FOREIGN PATENT DOCUMENTS

JP         2011 226882 A      11/2011

OTHER PUBLICATIONS

Qian et al., "Plasma Proteome Response to Severe Burn Injury Revealed by 18O-Labeled "Universal" Reference-Based Quantitative Proteomics," J. Proteome Res. 2010, 9, 4779-4789.*
Varnum et al., "Plasma Biomarkers for Detecting Hodgkin's Lymphoma in HIV Patients," PLoS ONE 2011, 6(12):e29263.*
Kingsmore, "Multiplexed protein measurement: technologies and applications of protein and antibody arrays," Nat. Rev. Drug Discov. 2006, 5:310-320.*
Beltran et al., "Different Prognostic Factors for Survival in the Acute and Lymphomatous Adult T-Cell Leukemia/Lymphoma," *Leuk. Res.* 35:334-339, 2010.
Child et al., "Serum Beta 2 Microglobulin and C-Reactive Protein in the Monitoring of Lymphomas: Findings in a Multicenter Study and Experience in Selected Patients," *Cancer* 45:318-326, 1980.

* cited by examiner

*Primary Examiner* — Samuel Woolwine
*Assistant Examiner* — Kaijiang Zhang
(74) *Attorney, Agent, or Firm* — Klarquist Sparkman, LLP

(57) ABSTRACT

A biomarker, method, test kit, and diagnostic system for detecting the presence of lymphoma in a person are disclosed. The lymphoma may be Hodgkin's lymphoma or non-Hodgkin's lymphoma. The person may be a high-risk subject. In one embodiment, a plasma sample from a person is obtained. The level of at least one protein listed in Table S3 in the plasma sample is measured. The level of at least one protein in the plasma sample is compared with the level in a normal or healthy subject. The lymphoma is diagnosed based upon the level of the at least one protein in the plasma sample in comparison to the normal or healthy level.

8 Claims, No Drawings

SEQUENCE LISTING

```
<160> NUMBER OF SEQ ID NOS: 646

<210> SEQ ID NO 1
<211> LENGTH: 8
<212> TYPE: PRT
<213> ORGANISM: Homo sapiens

<400> SEQUENCE: 1

Phe Val Thr Lys Ala Glu Glu Lys
1               5

<210> SEQ ID NO 2
<211> LENGTH: 9
<212> TYPE: PRT
<213> ORGANISM: Homo sapiens

<400> SEQUENCE: 2

Tyr Asn Asp Tyr Leu Ile Thr Ile Lys
1               5

<210> SEQ ID NO 3
<211> LENGTH: 20
<212> TYPE: PRT
<213> ORGANISM: Homo sapiens

<400> SEQUENCE: 3

Ser Leu Pro Ala Pro Trp Leu Ser Met Ala Pro Val Ser Trp Ile Thr
1               5                   10                  15
```

```
Pro Gly Leu Lys
        20
```

<210> SEQ ID NO 4
<211> LENGTH: 17
<212> TYPE: PRT
<213> ORGANISM: Homo sapiens

<400> SEQUENCE: 4

```
Ala Phe Gln Pro Phe Phe Val Glu Leu Thr Met Pro Tyr Ser Val Ile
1               5                   10                  15

Arg
```

<210> SEQ ID NO 5
<211> LENGTH: 16
<212> TYPE: PRT
<213> ORGANISM: Homo sapiens

<400> SEQUENCE: 5

```
Ala Ser Val Ser Val Leu Gly Asp Ile Leu Gly Ser Ala Met Gln Asn
1               5                   10                  15
```

<210> SEQ ID NO 6
<211> LENGTH: 9
<212> TYPE: PRT
<213> ORGANISM: Homo sapiens

<400> SEQUENCE: 6

```
Ala Thr Val Leu Asn Tyr Leu Pro Lys
1               5
```

<210> SEQ ID NO 7
<211> LENGTH: 27
<212> TYPE: PRT
<213> ORGANISM: Homo sapiens

<400> SEQUENCE: 7

```
Ala Val Asp Gln Ser Val Leu Leu Met Lys Pro Asp Ala Glu Leu Ser
1               5                   10                  15

Ala Ser Ser Val Tyr Asn Leu Leu Pro Glu Lys
            20                  25
```

<210> SEQ ID NO 8
<211> LENGTH: 13
<212> TYPE: PRT
<213> ORGANISM: Homo sapiens

<400> SEQUENCE: 8

```
Ala Tyr Ala Phe Ala Leu Ala Gly Asn Gln Asp Lys Arg
1               5                   10
```

<210> SEQ ID NO 9
<211> LENGTH: 12
<212> TYPE: PRT
<213> ORGANISM: Homo sapiens

<400> SEQUENCE: 9

```
Asp Met Tyr Ser Phe Leu Glu Asp Met Gly Leu Lys
1               5                   10
```

<210> SEQ ID NO 10
<211> LENGTH: 16
<212> TYPE: PRT
<213> ORGANISM: Homo sapiens

```
<400> SEQUENCE: 10

Asp Thr Val Ile Lys Pro Leu Leu Val Glu Pro Glu Gly Leu Glu Lys
1               5                   10                  15

<210> SEQ ID NO 11
<211> LENGTH: 30
<212> TYPE: PRT
<213> ORGANISM: Homo sapiens

<400> SEQUENCE: 11

Gly Gly Val Glu Asp Glu Val Thr Leu Ser Ala Tyr Ile Thr Ile Ala
1               5                   10                  15

Leu Leu Glu Ile Pro Leu Thr Val Thr His Pro Val Val Arg
            20                  25                  30

<210> SEQ ID NO 12
<211> LENGTH: 10
<212> TYPE: PRT
<213> ORGANISM: Homo sapiens

<400> SEQUENCE: 12

Gly His Phe Ser Ile Ser Ile Pro Val Lys
1               5                   10

<210> SEQ ID NO 13
<211> LENGTH: 7
<212> TYPE: PRT
<213> ORGANISM: Homo sapiens

<400> SEQUENCE: 13

Gly Pro Thr Gln Glu Phe Lys
1               5

<210> SEQ ID NO 14
<211> LENGTH: 12
<212> TYPE: PRT
<213> ORGANISM: Homo sapiens

<400> SEQUENCE: 14

His Tyr Asp Gly Ser Tyr Ser Thr Phe Gly Glu Arg
1               5                   10

<210> SEQ ID NO 15
<211> LENGTH: 18
<212> TYPE: PRT
<213> ORGANISM: Homo sapiens

<400> SEQUENCE: 15

Leu Leu Ile Tyr Ala Val Leu Pro Thr Gly Asp Val Ile Gly Asp Ser
1               5                   10                  15

Ala Lys

<210> SEQ ID NO 16
<211> LENGTH: 18
<212> TYPE: PRT
<213> ORGANISM: Homo sapiens

<400> SEQUENCE: 16

Leu Leu Leu Gln Gln Val Ser Leu Pro Glu Leu Pro Gly Glu Tyr Ser
1               5                   10                  15

Met Lys
```

<210> SEQ ID NO 17
<211> LENGTH: 11
<212> TYPE: PRT
<213> ORGANISM: Homo sapiens

<400> SEQUENCE: 17

Leu Pro Pro Asn Val Val Glu Glu Ser Ala Arg
1               5                   10

<210> SEQ ID NO 18
<211> LENGTH: 10
<212> TYPE: PRT
<213> ORGANISM: Homo sapiens

<400> SEQUENCE: 18

Gln Gly Ile Pro Phe Phe Gly Gln Val Arg
1               5                   10

<210> SEQ ID NO 19
<211> LENGTH: 10
<212> TYPE: PRT
<213> ORGANISM: Homo sapiens

<400> SEQUENCE: 19

Gln Thr Val Ser Trp Ala Val Thr Pro Lys
1               5                   10

<210> SEQ ID NO 20
<211> LENGTH: 8
<212> TYPE: PRT
<213> ORGANISM: Homo sapiens

<400> SEQUENCE: 20

Ser Asp Ile Ala Pro Val Ala Arg
1               5

<210> SEQ ID NO 21
<211> LENGTH: 10
<212> TYPE: PRT
<213> ORGANISM: Homo sapiens

<400> SEQUENCE: 21

Ser Ile Tyr Lys Pro Gly Gln Thr Val Lys
1               5                   10

<210> SEQ ID NO 22
<211> LENGTH: 23
<212> TYPE: PRT
<213> ORGANISM: Homo sapiens

<400> SEQUENCE: 22

Ser Val Ser Gly Lys Pro Gln Tyr Met Val Leu Val Pro Ser Leu Leu
1               5                   10                  15

His Thr Glu Thr Thr Glu Lys
            20

<210> SEQ ID NO 23
<211> LENGTH: 9
<212> TYPE: PRT
<213> ORGANISM: Homo sapiens

<400> SEQUENCE: 23

Thr Gly Thr His Gly Leu Leu Val Lys
1               5

<210> SEQ ID NO 24
<211> LENGTH: 14
<212> TYPE: PRT
<213> ORGANISM: Homo sapiens

<400> SEQUENCE: 24

Val Ile Lys Pro Leu Leu Val Glu Pro Glu Gly Leu Glu Lys
1               5                   10

<210> SEQ ID NO 25
<211> LENGTH: 18
<212> TYPE: PRT
<213> ORGANISM: Homo sapiens

<400> SEQUENCE: 25

Val Ser Val Gln Leu Glu Ala Ser Pro Ala Phe Leu Ala Val Pro Val
1               5                   10                  15

Glu Lys

<210> SEQ ID NO 26
<211> LENGTH: 10
<212> TYPE: PRT
<213> ORGANISM: Homo sapiens

<400> SEQUENCE: 26

Ala Gly Phe Ala Gly Asp Asp Ala Pro Arg
1               5                   10

<210> SEQ ID NO 27
<211> LENGTH: 8
<212> TYPE: PRT
<213> ORGANISM: Homo sapiens

<400> SEQUENCE: 27

Asp Leu Thr Asp Tyr Leu Met Lys
1               5

<210> SEQ ID NO 28
<211> LENGTH: 12
<212> TYPE: PRT
<213> ORGANISM: Homo sapiens

<400> SEQUENCE: 28

Asp Ser Tyr Val Gly Asp Glu Ala Gln Ser Lys Arg
1               5                   10

<210> SEQ ID NO 29
<211> LENGTH: 11
<212> TYPE: PRT
<213> ORGANISM: Homo sapiens

<400> SEQUENCE: 29

Glu Ile Thr Ala Leu Ala Pro Ser Thr Met Lys
1               5                   10

<210> SEQ ID NO 30
<211> LENGTH: 11
<212> TYPE: PRT
<213> ORGANISM: Homo sapiens

<400> SEQUENCE: 30

His Gln Gly Val Met Val Gly Met Gly Gln Lys
1               5                   10

<210> SEQ ID NO 31
<211> LENGTH: 16
<212> TYPE: PRT
<213> ORGANISM: Homo sapiens

<400> SEQUENCE: 31

Ser Tyr Glu Leu Pro Asp Gly Gln Val Ile Thr Ile Gly Asn Glu Arg
1               5                   10                  15

<210> SEQ ID NO 32
<211> LENGTH: 27
<212> TYPE: PRT
<213> ORGANISM: Homo sapiens

<400> SEQUENCE: 32

Tyr Pro Ile Glu His Gly Ile Ile Thr Asn Trp Asp Asp Met Glu Lys
1               5                   10                  15

Ile Trp His His Thr Phe Tyr Asn Glu Leu Arg
            20                  25

<210> SEQ ID NO 33
<211> LENGTH: 10
<212> TYPE: PRT
<213> ORGANISM: Homo sapiens

<400> SEQUENCE: 33

Ala Gly Phe Ala Gly Asp Asp Ala Pro Arg
1               5                   10

<210> SEQ ID NO 34
<211> LENGTH: 8
<212> TYPE: PRT
<213> ORGANISM: Homo sapiens

<400> SEQUENCE: 34

Asp Leu Thr Asp Tyr Leu Met Lys
1               5

<210> SEQ ID NO 35
<211> LENGTH: 12
<212> TYPE: PRT
<213> ORGANISM: Homo sapiens

<400> SEQUENCE: 35

Asp Ser Tyr Val Gly Asp Glu Ala Gln Ser Lys Arg
1               5                   10

<210> SEQ ID NO 36
<211> LENGTH: 11
<212> TYPE: PRT
<213> ORGANISM: Homo sapiens

<400> SEQUENCE: 36

Glu Ile Thr Ala Leu Ala Pro Ser Thr Met Lys
1               5                   10

<210> SEQ ID NO 37
<211> LENGTH: 11
<212> TYPE: PRT
<213> ORGANISM: Homo sapiens

<400> SEQUENCE: 37

His Gln Gly Val Met Val Gly Met Gly Gln Lys

```
1               5                   10
```

<210> SEQ ID NO 38
<211> LENGTH: 16
<212> TYPE: PRT
<213> ORGANISM: Homo sapiens

<400> SEQUENCE: 38

```
Ser Tyr Glu Leu Pro Asp Gly Gln Val Ile Thr Ile Gly Asn Glu Arg
1               5                   10                  15
```

<210> SEQ ID NO 39
<211> LENGTH: 30
<212> TYPE: PRT
<213> ORGANISM: Homo sapiens

<400> SEQUENCE: 39

```
Thr Thr Gly Ile Val Met Asp Ser Gly Asp Gly Val Thr His Thr Val
1               5                   10                  15

Pro Ile Tyr Glu Gly Tyr Ala Leu Pro His Ala Ile Leu Arg
            20                  25                  30
```

<210> SEQ ID NO 40
<211> LENGTH: 12
<212> TYPE: PRT
<213> ORGANISM: Homo sapiens

<400> SEQUENCE: 40

```
Leu Ala Ile Leu Gly Ile His Asn Glu Val Ser Lys
1               5                   10
```

<210> SEQ ID NO 41
<211> LENGTH: 12
<212> TYPE: PRT
<213> ORGANISM: Homo sapiens

<400> SEQUENCE: 41

```
Val Gly Trp Glu Gln Leu Leu Thr Thr Ile Ala Arg
1               5                   10
```

<210> SEQ ID NO 42
<211> LENGTH: 10
<212> TYPE: PRT
<213> ORGANISM: Homo sapiens

<400> SEQUENCE: 42

```
Asn Phe Asn Ile Ala Gly Thr Val Val Lys
1               5                   10
```

<210> SEQ ID NO 43
<211> LENGTH: 14
<212> TYPE: PRT
<213> ORGANISM: Homo sapiens

<400> SEQUENCE: 43

```
Ser Thr Leu Ala Phe Asn Thr Tyr Val His Phe Gln Gly Lys
1               5                   10
```

<210> SEQ ID NO 44
<211> LENGTH: 17
<212> TYPE: PRT
<213> ORGANISM: Homo sapiens

<400> SEQUENCE: 44

```
Val Gly Glu Val Leu Asn Ser Ile Phe Phe Glu Leu Glu Ala Asp Glu
1               5                   10                  15

Arg

<210> SEQ ID NO 45
<211> LENGTH: 7
<212> TYPE: PRT
<213> ORGANISM: Homo sapiens

<400> SEQUENCE: 45

Phe Ser Val Val Tyr Ala Lys
1               5

<210> SEQ ID NO 46
<211> LENGTH: 8
<212> TYPE: PRT
<213> ORGANISM: Homo sapiens

<400> SEQUENCE: 46

Ala Glu Phe Ala Glu Val Ser Lys
1               5

<210> SEQ ID NO 47
<211> LENGTH: 12
<212> TYPE: PRT
<213> ORGANISM: Homo sapiens

<400> SEQUENCE: 47

Ala Val Met Asp Asp Phe Ala Ala Phe Val Glu Lys
1               5                   10

<210> SEQ ID NO 48
<211> LENGTH: 13
<212> TYPE: PRT
<213> ORGANISM: Homo sapiens

<400> SEQUENCE: 48

Asp Val Phe Leu Gly Met Phe Leu Tyr Glu Tyr Ala Arg
1               5                   10

<210> SEQ ID NO 49
<211> LENGTH: 10
<212> TYPE: PRT
<213> ORGANISM: Homo sapiens

<400> SEQUENCE: 49

Phe Lys Asp Leu Gly Glu Glu Asn Phe Lys
1               5                   10

<210> SEQ ID NO 50
<211> LENGTH: 8
<212> TYPE: PRT
<213> ORGANISM: Homo sapiens

<400> SEQUENCE: 50

Phe Gln Asn Ala Leu Leu Val Arg
1               5

<210> SEQ ID NO 51
<211> LENGTH: 10
<212> TYPE: PRT
<213> ORGANISM: Homo sapiens

<400> SEQUENCE: 51
```

```
Lys Gln Thr Ala Leu Val Glu Leu Val Lys
 1               5                  10

<210> SEQ ID NO 52
<211> LENGTH: 8
<212> TYPE: PRT
<213> ORGANISM: Homo sapiens

<400> SEQUENCE: 52

Lys Tyr Leu Tyr Glu Ile Ala Arg
 1               5

<210> SEQ ID NO 53
<211> LENGTH: 11
<212> TYPE: PRT
<213> ORGANISM: Homo sapiens

<400> SEQUENCE: 53

Leu Val Ala Ala Ser Gln Ala Ala Leu Gly Leu
 1               5                  10

<210> SEQ ID NO 54
<211> LENGTH: 10
<212> TYPE: PRT
<213> ORGANISM: Homo sapiens

<400> SEQUENCE: 54

Leu Val Asn Glu Val Thr Glu Phe Ala Lys
 1               5                  10

<210> SEQ ID NO 55
<211> LENGTH: 7
<212> TYPE: PRT
<213> ORGANISM: Homo sapiens

<400> SEQUENCE: 55

Leu Val Thr Asp Leu Thr Lys
 1               5

<210> SEQ ID NO 56
<211> LENGTH: 13
<212> TYPE: PRT
<213> ORGANISM: Homo sapiens

<400> SEQUENCE: 56

Gln Asn Cys Glu Leu Phe Glu Gln Leu Gly Glu Tyr Lys
 1               5                  10

<210> SEQ ID NO 57
<211> LENGTH: 15
<212> TYPE: PRT
<213> ORGANISM: Homo sapiens

<400> SEQUENCE: 57

Arg His Pro Tyr Phe Tyr Ala Pro Glu Leu Leu Phe Phe Ala Lys
 1               5                  10                  15

<210> SEQ ID NO 58
<211> LENGTH: 8
<212> TYPE: PRT
<213> ORGANISM: Homo sapiens

<400> SEQUENCE: 58

Thr Tyr Glu Thr Thr Leu Glu Lys
 1               5
```

<210> SEQ ID NO 59
<211> LENGTH: 17
<212> TYPE: PRT
<213> ORGANISM: Homo sapiens

<400> SEQUENCE: 59

Val Phe Asp Glu Phe Lys Pro Leu Val Glu Glu Pro Gln Asn Leu Ile
1               5                   10                  15

Lys

<210> SEQ ID NO 60
<211> LENGTH: 14
<212> TYPE: PRT
<213> ORGANISM: Homo sapiens

<400> SEQUENCE: 60

Val Pro Gln Val Ser Thr Pro Thr Leu Val Glu Val Ser Arg
1               5                   10

<210> SEQ ID NO 61
<211> LENGTH: 7
<212> TYPE: PRT
<213> ORGANISM: Homo sapiens

<400> SEQUENCE: 61

Tyr Leu Tyr Glu Ile Ala Arg
1               5

<210> SEQ ID NO 62
<211> LENGTH: 30
<212> TYPE: PRT
<213> ORGANISM: Homo sapiens

<400> SEQUENCE: 62

Phe Met Asn Ser Gly Gln Thr Cys Val Ala Pro Asp Tyr Ile Leu Cys
1               5                   10                  15

Asp Pro Ser Ile Gln Asn Gln Ile Val Glu Lys Leu Lys Lys
            20                  25                  30

<210> SEQ ID NO 63
<211> LENGTH: 12
<212> TYPE: PRT
<213> ORGANISM: Homo sapiens

<400> SEQUENCE: 63

Ala Phe Ile Gln Leu Trp Ala Phe Asp Ala Val Lys
1               5                   10

<210> SEQ ID NO 64
<211> LENGTH: 11
<212> TYPE: PRT
<213> ORGANISM: Homo sapiens

<400> SEQUENCE: 64

Thr Val Ala Ala Cys Asn Leu Pro Ile Val Arg
1               5                   10

<210> SEQ ID NO 65
<211> LENGTH: 6
<212> TYPE: PRT
<213> ORGANISM: Homo sapiens

<400> SEQUENCE: 65

```
Lys Arg Glu Arg Leu Lys
1               5

<210> SEQ ID NO 66
<211> LENGTH: 8
<212> TYPE: PRT
<213> ORGANISM: Homo sapiens

<400> SEQUENCE: 66

Ala Leu Glu Gln Ala Leu Glu Lys
1               5

<210> SEQ ID NO 67
<211> LENGTH: 9
<212> TYPE: PRT
<213> ORGANISM: Homo sapiens

<400> SEQUENCE: 67

Ala Lys Pro Ala Leu Glu Asp Leu Arg
1               5

<210> SEQ ID NO 68
<211> LENGTH: 10
<212> TYPE: PRT
<213> ORGANISM: Homo sapiens

<400> SEQUENCE: 68

Phe Leu Ser Ala Leu Glu Glu Tyr Thr Lys
1               5                   10

<210> SEQ ID NO 69
<211> LENGTH: 18
<212> TYPE: PRT
<213> ORGANISM: Homo sapiens

<400> SEQUENCE: 69

Leu His Glu Leu Gln Glu Lys Leu Ser Pro Leu Gly Glu Glu Met Arg
1               5                   10                  15

Asp Arg

<210> SEQ ID NO 70
<211> LENGTH: 7
<212> TYPE: PRT
<213> ORGANISM: Homo sapiens

<400> SEQUENCE: 70

Gln Lys Val Glu Pro Leu Arg
1               5

<210> SEQ ID NO 71
<211> LENGTH: 15
<212> TYPE: PRT
<213> ORGANISM: Homo sapiens

<400> SEQUENCE: 71

Gln Lys Val Glu Pro Leu Arg Ala Glu Leu Gln Glu Gly Ala Arg
1               5                   10                  15

<210> SEQ ID NO 72
<211> LENGTH: 13
<212> TYPE: PRT
<213> ORGANISM: Homo sapiens

<400> SEQUENCE: 72
```

Val Glu Pro Leu Arg Ala Glu Leu Gln Glu Gly Ala Arg
1               5                   10

<210> SEQ ID NO 73
<211> LENGTH: 11
<212> TYPE: PRT
<213> ORGANISM: Homo sapiens

<400> SEQUENCE: 73

Val Gln Pro Tyr Leu Asp Asp Phe Gln Lys Lys
1               5                   10

<210> SEQ ID NO 74
<211> LENGTH: 12
<212> TYPE: PRT
<213> ORGANISM: Homo sapiens

<400> SEQUENCE: 74

Val Ser Phe Leu Ser Ala Leu Glu Glu Tyr Thr Lys
1               5                   10

<210> SEQ ID NO 75
<211> LENGTH: 11
<212> TYPE: PRT
<213> ORGANISM: Homo sapiens

<400> SEQUENCE: 75

Asp Ser Glu Lys Leu Lys Glu Glu Ile Gly Lys
1               5                   10

<210> SEQ ID NO 76
<211> LENGTH: 11
<212> TYPE: PRT
<213> ORGANISM: Homo sapiens

<400> SEQUENCE: 76

Ile Ser Ala Ser Ala Glu Glu Leu Arg Gln Arg
1               5                   10

<210> SEQ ID NO 77
<211> LENGTH: 8
<212> TYPE: PRT
<213> ORGANISM: Homo sapiens

<400> SEQUENCE: 77

Gln Leu Thr Pro Tyr Ala Gln Arg
1               5

<210> SEQ ID NO 78
<211> LENGTH: 12
<212> TYPE: PRT
<213> ORGANISM: Homo sapiens

<400> SEQUENCE: 78

Arg Arg Val Glu Pro Tyr Gly Glu Asn Phe Asn Lys
1               5                   10

<210> SEQ ID NO 79
<211> LENGTH: 10
<212> TYPE: PRT
<213> ORGANISM: Homo sapiens

<400> SEQUENCE: 79

Val Glu Pro Tyr Gly Glu Asn Phe Asn Lys

```
                        1               5                      10
```

<210> SEQ ID NO 80
<211> LENGTH: 15
<212> TYPE: PRT
<213> ORGANISM: Homo sapiens

<400> SEQUENCE: 80

```
Ala Leu Tyr Trp Val Asn Gly Gln Val Pro Asp Gly Val Ser Lys
1               5                   10                  15
```

<210> SEQ ID NO 81
<211> LENGTH: 10
<212> TYPE: PRT
<213> ORGANISM: Homo sapiens

<400> SEQUENCE: 81

```
Asp Lys Ile Gly Val Glu Leu Thr Gly Arg
1               5                   10
```

<210> SEQ ID NO 82
<211> LENGTH: 18
<212> TYPE: PRT
<213> ORGANISM: Homo sapiens

<400> SEQUENCE: 82

```
Glu Glu Glu Ala Ala Ser Gly Leu Leu Thr Ser Leu Lys Asp Asn Val
1               5                   10                  15

Pro Lys
```

<210> SEQ ID NO 83
<211> LENGTH: 11
<212> TYPE: PRT
<213> ORGANISM: Homo sapiens

<400> SEQUENCE: 83

```
Glu Asn Phe Ala Gly Glu Ala Thr Leu Gln Arg
1               5                   10
```

<210> SEQ ID NO 84
<211> LENGTH: 8
<212> TYPE: PRT
<213> ORGANISM: Homo sapiens

<400> SEQUENCE: 84

```
Glu Ser Val Lys Phe Ser Ser Lys
1               5
```

<210> SEQ ID NO 85
<211> LENGTH: 15
<212> TYPE: PRT
<213> ORGANISM: Homo sapiens

<400> SEQUENCE: 85

```
His Ile Tyr Ala Ile Ser Ser Ala Ala Leu Ser Ala Ser Tyr Lys
1               5                   10                  15
```

<210> SEQ ID NO 86
<211> LENGTH: 19
<212> TYPE: PRT
<213> ORGANISM: Homo sapiens

<400> SEQUENCE: 86

```
Asn Ile Gln Glu Tyr Leu Ser Ile Leu Thr Asp Pro Asp Gly Lys Gly
1               5                   10                  15
```

```
1               5                   10                  15

Lys Glu Lys

<210> SEQ ID NO 87
<211> LENGTH: 8
<212> TYPE: PRT
<213> ORGANISM: Homo sapiens

<400> SEQUENCE: 87

Gln Ile Asp Asp Ile Asp Val Arg
1               5

<210> SEQ ID NO 88
<211> LENGTH: 8
<212> TYPE: PRT
<213> ORGANISM: Homo sapiens

<400> SEQUENCE: 88

Ser Lys Glu Val Pro Glu Ala Arg
1               5

<210> SEQ ID NO 89
<211> LENGTH: 12
<212> TYPE: PRT
<213> ORGANISM: Homo sapiens

<400> SEQUENCE: 89

Ser Lys Pro Thr Val Ser Ser Met Glu Phe Lys
1               5                   10

<210> SEQ ID NO 90
<211> LENGTH: 17
<212> TYPE: PRT
<213> ORGANISM: Homo sapiens

<400> SEQUENCE: 90

Thr Glu His Gly Ser Glu Met Leu Phe Phe Gly Asn Ala Ile Glu Gly
1               5                   10                  15

Lys

<210> SEQ ID NO 91
<211> LENGTH: 15
<212> TYPE: PRT
<213> ORGANISM: Homo sapiens

<400> SEQUENCE: 91

Thr Leu Gln Gly Ile Pro Gln Met Ile Gly Glu Val Ile Arg Lys
1               5                   10                  15

<210> SEQ ID NO 92
<211> LENGTH: 28
<212> TYPE: PRT
<213> ORGANISM: Homo sapiens

<400> SEQUENCE: 92

Val Leu Val Asp His Phe Gly Tyr Thr Lys Asp Asp Lys His Glu Gln
1               5                   10                  15

Asp Met Val Asn Gly Ile Met Leu Ser Val Glu Lys
                20                  25

<210> SEQ ID NO 93
<211> LENGTH: 11
<212> TYPE: PRT
```

<213> ORGANISM: Homo sapiens

<400> SEQUENCE: 93

Val Arg Glu Ser Asp Glu Glu Thr Gln Ile Lys
1               5                   10

<210> SEQ ID NO 94
<211> LENGTH: 13
<212> TYPE: PRT
<213> ORGANISM: Homo sapiens

<400> SEQUENCE: 94

Tyr Glu Val Asp Gln Gln Ile Gln Val Leu Met Asp Lys
1               5                   10

<210> SEQ ID NO 95
<211> LENGTH: 9
<212> TYPE: PRT
<213> ORGANISM: Homo sapiens

<400> SEQUENCE: 95

Tyr Lys Asn Phe Ala Thr Ser Asn Lys
1               5

<210> SEQ ID NO 96
<211> LENGTH: 20
<212> TYPE: PRT
<213> ORGANISM: Homo sapiens

<400> SEQUENCE: 96

Tyr Leu Arg Thr Glu His Gly Ser Glu Met Leu Phe Phe Gly Asn Ala
1               5                   10                  15

Ile Glu Gly Lys
            20

<210> SEQ ID NO 97
<211> LENGTH: 9
<212> TYPE: PRT
<213> ORGANISM: Homo sapiens

<400> SEQUENCE: 97

Glu Trp Phe Ser Glu Thr Phe Gln Lys
1               5

<210> SEQ ID NO 98
<211> LENGTH: 11
<212> TYPE: PRT
<213> ORGANISM: Homo sapiens

<400> SEQUENCE: 98

Leu Lys Glu Phe Gly Asn Thr Leu Glu Asp Lys
1               5                   10

<210> SEQ ID NO 99
<211> LENGTH: 11
<212> TYPE: PRT
<213> ORGANISM: Homo sapiens

<400> SEQUENCE: 99

Met Arg Glu Trp Phe Ser Glu Thr Phe Gln Lys
1               5                   10

<210> SEQ ID NO 100
<211> LENGTH: 21

```
<212> TYPE: PRT
<213> ORGANISM: Homo sapiens

<400> SEQUENCE: 100

Thr Pro Asp Val Ser Ser Ala Leu Asp Lys Leu Lys Glu Phe Gly Asn
1               5                   10                  15

Thr Leu Glu Asp Lys
            20

<210> SEQ ID NO 101
<211> LENGTH: 9
<212> TYPE: PRT
<213> ORGANISM: Homo sapiens

<400> SEQUENCE: 101

Thr Ala Ala Gln Asn Leu Tyr Glu Lys
1               5

<210> SEQ ID NO 102
<211> LENGTH: 17
<212> TYPE: PRT
<213> ORGANISM: Homo sapiens

<400> SEQUENCE: 102

Ser Glu Ala Glu Asp Ala Ser Leu Leu Ser Phe Met Gln Gly Tyr Met
1               5                   10                  15

Lys

<210> SEQ ID NO 103
<211> LENGTH: 6
<212> TYPE: PRT
<213> ORGANISM: Homo sapiens

<400> SEQUENCE: 103

Phe Trp Asp Tyr Leu Arg
1               5

<210> SEQ ID NO 104
<211> LENGTH: 15
<212> TYPE: PRT
<213> ORGANISM: Homo sapiens

<400> SEQUENCE: 104

Gly Glu Val Gln Ala Met Leu Gly Gln Ser Thr Glu Glu Leu Arg
1               5                   10                  15

<210> SEQ ID NO 105
<211> LENGTH: 9
<212> TYPE: PRT
<213> ORGANISM: Homo sapiens

<400> SEQUENCE: 105

Leu Glu Glu Gln Ala Gln Gln Ile Arg
1               5

<210> SEQ ID NO 106
<211> LENGTH: 14
<212> TYPE: PRT
<213> ORGANISM: Homo sapiens

<400> SEQUENCE: 106

Leu Lys Ser Trp Phe Glu Pro Leu Val Glu Asp Met Gln Arg
1               5                   10
```

```
<210> SEQ ID NO 107
<211> LENGTH: 7
<212> TYPE: PRT
<213> ORGANISM: Homo sapiens

<400> SEQUENCE: 107

Met Glu Glu Met Gly Ser Arg
1               5

<210> SEQ ID NO 108
<211> LENGTH: 8
<212> TYPE: PRT
<213> ORGANISM: Homo sapiens

<400> SEQUENCE: 108

Gln Trp Ala Gly Leu Val Glu Lys
1               5

<210> SEQ ID NO 109
<211> LENGTH: 10
<212> TYPE: PRT
<213> ORGANISM: Homo sapiens

<400> SEQUENCE: 109

Arg Leu Ala Val Tyr Gln Ala Gly Ala Arg
1               5                   10

<210> SEQ ID NO 110
<211> LENGTH: 23
<212> TYPE: PRT
<213> ORGANISM: Homo sapiens

<400> SEQUENCE: 110

Trp Val Gln Thr Leu Ser Glu Gln Val Gln Glu Glu Leu Leu Ser Ser
1               5                   10                  15

Gln Val Thr Gln Glu Leu Arg
            20

<210> SEQ ID NO 111
<211> LENGTH: 14
<212> TYPE: PRT
<213> ORGANISM: Homo sapiens

<400> SEQUENCE: 111

Ser Gly Val Gln Gln Leu Ile Gln Tyr Tyr Gln Asp Gln Lys
1               5                   10

<210> SEQ ID NO 112
<211> LENGTH: 9
<212> TYPE: PRT
<213> ORGANISM: Homo sapiens

<400> SEQUENCE: 112

Ala Thr Val Val Tyr Gln Gly Glu Arg
1               5

<210> SEQ ID NO 113
<211> LENGTH: 9
<212> TYPE: PRT
<213> ORGANISM: Homo sapiens

<400> SEQUENCE: 113

Glu His Ser Ser Leu Ala Phe Trp Lys
1               5
```

<210> SEQ ID NO 114
<211> LENGTH: 17
<212> TYPE: PRT
<213> ORGANISM: Homo sapiens

<400> SEQUENCE: 114

Thr Cys Pro Lys Pro Asp Asp Leu Pro Phe Ser Thr Val Val Pro Leu
1               5                   10                  15

Lys

<210> SEQ ID NO 115
<211> LENGTH: 9
<212> TYPE: PRT
<213> ORGANISM: Homo sapiens

<400> SEQUENCE: 115

Asn Trp Phe Leu Lys Glu Phe Pro Arg
1               5

<210> SEQ ID NO 116
<211> LENGTH: 7
<212> TYPE: PRT
<213> ORGANISM: Homo sapiens

<400> SEQUENCE: 116

Ala Phe Leu Leu Thr Pro Arg
1               5

<210> SEQ ID NO 117
<211> LENGTH: 6
<212> TYPE: PRT
<213> ORGANISM: Homo sapiens

<400> SEQUENCE: 117

Phe Leu Leu Tyr Asn Arg
1               5

<210> SEQ ID NO 118
<211> LENGTH: 14
<212> TYPE: PRT
<213> ORGANISM: Homo sapiens

<400> SEQUENCE: 118

Lys Trp Ile Tyr His Leu Thr Glu Gly Ser Thr Asp Leu Arg
1               5                   10

<210> SEQ ID NO 119
<211> LENGTH: 12
<212> TYPE: PRT
<213> ORGANISM: Homo sapiens

<400> SEQUENCE: 119

Glu Thr Ile Val Leu Lys Glu Gly Ser Glu Tyr Arg
1               5                   10

<210> SEQ ID NO 120
<211> LENGTH: 13
<212> TYPE: PRT
<213> ORGANISM: Homo sapiens

<400> SEQUENCE: 120

Thr Leu Leu Gly Asp Gly Pro Val Val Thr Asp Pro Lys
1               5                   10

<210> SEQ ID NO 121
<211> LENGTH: 8
<212> TYPE: PRT
<213> ORGANISM: Homo sapiens

<400> SEQUENCE: 121

Glu Met Thr Gly Ser Gly Arg Arg
1               5

<210> SEQ ID NO 122
<211> LENGTH: 8
<212> TYPE: PRT
<213> ORGANISM: Homo sapiens

<400> SEQUENCE: 122

Ala Leu Leu Gln Ala Gln Gln Ala
1               5

<210> SEQ ID NO 123
<211> LENGTH: 10
<212> TYPE: PRT
<213> ORGANISM: Homo sapiens

<400> SEQUENCE: 123

Ala Gly Glu Val Gln Glu Pro Glu Leu Arg
1               5                   10

<210> SEQ ID NO 124
<211> LENGTH: 21
<212> TYPE: PRT
<213> ORGANISM: Homo sapiens

<400> SEQUENCE: 124

His Val Glu Asp Val Pro Ala Phe Gln Ala Leu Gly Ser Leu Asn Asp
1               5                   10                  15

Leu Gln Phe Phe Arg
            20

<210> SEQ ID NO 125
<211> LENGTH: 7
<212> TYPE: PRT
<213> ORGANISM: Homo sapiens

<400> SEQUENCE: 125

Ile Asp Val His Trp Thr Arg
1               5

<210> SEQ ID NO 126
<211> LENGTH: 12
<212> TYPE: PRT
<213> ORGANISM: Homo sapiens

<400> SEQUENCE: 126

Tyr Ser Leu Thr Tyr Ile Tyr Thr Gly Leu Ser Lys
1               5                   10

<210> SEQ ID NO 127
<211> LENGTH: 13
<212> TYPE: PRT
<213> ORGANISM: Homo sapiens

<400> SEQUENCE: 127

Ile Glu Lys Val Glu His Ser Asp Leu Ser Phe Ser Lys

```
1               5                   10
```

<210> SEQ ID NO 128
<211> LENGTH: 6
<212> TYPE: PRT
<213> ORGANISM: Homo sapiens

<400> SEQUENCE: 128

```
Ile Gln Val Tyr Ser Arg
1               5
```

<210> SEQ ID NO 129
<211> LENGTH: 8
<212> TYPE: PRT
<213> ORGANISM: Homo sapiens

<400> SEQUENCE: 129

```
Asp Asn Asn Ser Ile Ile Thr Arg
1               5
```

<210> SEQ ID NO 130
<211> LENGTH: 9
<212> TYPE: PRT
<213> ORGANISM: Homo sapiens

<400> SEQUENCE: 130

```
Trp Asn Asn Tyr Met Met Asp Trp Lys
1               5
```

<210> SEQ ID NO 131
<211> LENGTH: 17
<212> TYPE: PRT
<213> ORGANISM: Homo sapiens

<400> SEQUENCE: 131

```
Ala Gly Pro Trp Thr Pro Glu Ala Ala Val Glu His Pro Glu Ala Val
1               5                   10                  15

Arg
```

<210> SEQ ID NO 132
<211> LENGTH: 9
<212> TYPE: PRT
<213> ORGANISM: Homo sapiens

<400> SEQUENCE: 132

```
His Asp Leu Gly His Phe Met Leu Arg
1               5
```

<210> SEQ ID NO 133
<211> LENGTH: 19
<212> TYPE: PRT
<213> ORGANISM: Homo sapiens

<400> SEQUENCE: 133

```
Met Ala Ala Leu Asn Met Ile Trp Ala Gly Ser Arg Thr Tyr Asp Pro
1               5                   10                  15

Asn Leu Arg
```

<210> SEQ ID NO 134
<211> LENGTH: 6
<212> TYPE: PRT
<213> ORGANISM: Homo sapiens

<400> SEQUENCE: 134

```
Ala Ser Ala Val Ala Arg
1               5
```

<210> SEQ ID NO 135
<211> LENGTH: 24
<212> TYPE: PRT
<213> ORGANISM: Homo sapiens

<400> SEQUENCE: 135

```
Gln Glu Ala Leu Glu Leu Met Asn Gln Asn Leu Asp Ile Tyr Glu Gln
1               5                   10                  15

Gln Val Met Thr Ala Ala Gln Lys
            20
```

<210> SEQ ID NO 136
<211> LENGTH: 10
<212> TYPE: PRT
<213> ORGANISM: Homo sapiens

<400> SEQUENCE: 136

```
Ser Leu Gly Phe Cys Asp Thr Thr Asn Lys
1               5                   10
```

<210> SEQ ID NO 137
<211> LENGTH: 20
<212> TYPE: PRT
<213> ORGANISM: Homo sapiens

<400> SEQUENCE: 137

```
Asp Gln Thr Ile Arg Phe Asp His Val Ile Thr Asn Met Asn Asn Asn
1               5                   10                  15

Tyr Glu Pro Arg
            20
```

<210> SEQ ID NO 138
<211> LENGTH: 7
<212> TYPE: PRT
<213> ORGANISM: Homo sapiens

<400> SEQUENCE: 138

```
Tyr Thr Thr Glu Ile Ile Lys
1               5
```

<210> SEQ ID NO 139
<211> LENGTH: 8
<212> TYPE: PRT
<213> ORGANISM: Homo sapiens

<400> SEQUENCE: 139

```
Glu Phe Met Ser Gln Gly Asn Lys
1               5
```

<210> SEQ ID NO 140
<211> LENGTH: 14
<212> TYPE: PRT
<213> ORGANISM: Homo sapiens

<400> SEQUENCE: 140

```
Gly Ser Glu Ala Ile Asn Ala Pro Gly Asp Asn Pro Ala Lys
1               5                   10
```

<210> SEQ ID NO 141
<211> LENGTH: 15

```
<212> TYPE: PRT
<213> ORGANISM: Homo sapiens

<400> SEQUENCE: 141

Leu Gly Asn Phe Pro Trp Gln Ala Phe Thr Ser Ile His Gly Arg
1               5                   10                  15

<210> SEQ ID NO 142
<211> LENGTH: 28
<212> TYPE: PRT
<213> ORGANISM: Homo sapiens

<400> SEQUENCE: 142

Glu Val Lys Val Glu Lys Pro Thr Ala Asp Ala Glu Ala Tyr Val Phe
1               5                   10                  15

Thr Pro Asn Met Ile Cys Ala Gly Gly Glu Lys Gly
            20                  25

<210> SEQ ID NO 143
<211> LENGTH: 10
<212> TYPE: PRT
<213> ORGANISM: Homo sapiens

<400> SEQUENCE: 143

Ile Ile Gly Gly Ser Asp Ala Asp Ile Lys
1               5                   10

<210> SEQ ID NO 144
<211> LENGTH: 11
<212> TYPE: PRT
<213> ORGANISM: Homo sapiens

<400> SEQUENCE: 144

Thr Asn Phe Asp Asn Asp Ile Ala Leu Val Arg
1               5                   10

<210> SEQ ID NO 145
<211> LENGTH: 10
<212> TYPE: PRT
<213> ORGANISM: Homo sapiens

<400> SEQUENCE: 145

Val Lys Asn Tyr Val Asp Trp Ile Met Lys
1               5                   10

<210> SEQ ID NO 146
<211> LENGTH: 12
<212> TYPE: PRT
<213> ORGANISM: Homo sapiens

<400> SEQUENCE: 146

Ser Ser Gly Gln Trp Gln Thr Pro Gly Ala Thr Arg
1               5                   10

<210> SEQ ID NO 147
<211> LENGTH: 10
<212> TYPE: PRT
<213> ORGANISM: Homo sapiens

<400> SEQUENCE: 147

Thr Pro Trp His Val Thr Ile Lys Pro Lys
1               5                   10

<210> SEQ ID NO 148
```

```
<211> LENGTH: 12
<212> TYPE: PRT
<213> ORGANISM: Homo sapiens

<400> SEQUENCE: 148

Ala Pro Ser Thr Trp Leu Thr Ala Tyr Val Val Lys
1               5                   10

<210> SEQ ID NO 149
<211> LENGTH: 11
<212> TYPE: PRT
<213> ORGANISM: Homo sapiens

<400> SEQUENCE: 149

Asp Gln Leu Thr Cys Asn Lys Phe Asp Leu Lys
1               5                   10

<210> SEQ ID NO 150
<211> LENGTH: 10
<212> TYPE: PRT
<213> ORGANISM: Homo sapiens

<400> SEQUENCE: 150

Asp Ser Cys Val Gly Ser Leu Val Val Lys
1               5                   10

<210> SEQ ID NO 151
<211> LENGTH: 8
<212> TYPE: PRT
<213> ORGANISM: Homo sapiens

<400> SEQUENCE: 151

Glu Ala Leu Lys Leu Glu Glu Lys
1               5

<210> SEQ ID NO 152
<211> LENGTH: 15
<212> TYPE: PRT
<213> ORGANISM: Homo sapiens

<400> SEQUENCE: 152

Glu Thr Lys Glu Asn Glu Gly Phe Thr Val Thr Ala Glu Gly Lys
1               5                   10                  15

<210> SEQ ID NO 153
<211> LENGTH: 24
<212> TYPE: PRT
<213> ORGANISM: Homo sapiens

<400> SEQUENCE: 153

Glu Tyr Val Leu Pro Ser Phe Glu Val Ile Val Glu Pro Thr Glu Lys
1               5                   10                  15

Phe Tyr Tyr Ile Tyr Asn Glu Lys
            20

<210> SEQ ID NO 154
<211> LENGTH: 14
<212> TYPE: PRT
<213> ORGANISM: Homo sapiens

<400> SEQUENCE: 154

Gly Gln Gly Thr Leu Ser Val Val Thr Met Tyr His Ala Lys
1               5                   10
```

```
<210> SEQ ID NO 155
<211> LENGTH: 8
<212> TYPE: PRT
<213> ORGANISM: Homo sapiens

<400> SEQUENCE: 155

Ile Glu Gly Asp His Gly Ala Arg
1               5

<210> SEQ ID NO 156
<211> LENGTH: 22
<212> TYPE: PRT
<213> ORGANISM: Homo sapiens

<400> SEQUENCE: 156

Ile Leu Leu Gln Gly Thr Pro Val Ala Gln Met Thr Glu Asp Ala Val
1               5                   10                  15

Asp Ala Glu Arg Leu Lys
            20

<210> SEQ ID NO 157
<211> LENGTH: 16
<212> TYPE: PRT
<213> ORGANISM: Homo sapiens

<400> SEQUENCE: 157

Pro Glu Ser Trp Leu Trp Asn Val Glu Asp Leu Lys Glu Pro Pro Lys
1               5                   10                  15

<210> SEQ ID NO 158
<211> LENGTH: 17
<212> TYPE: PRT
<213> ORGANISM: Homo sapiens

<400> SEQUENCE: 158

Pro Pro Ala Asp Leu Ser Asp Gln Val Pro Asp Thr Glu Ser Glu Thr
1               5                   10                  15

Arg

<210> SEQ ID NO 159
<211> LENGTH: 17
<212> TYPE: PRT
<213> ORGANISM: Homo sapiens

<400> SEQUENCE: 159

Pro Tyr Val Ile Val Pro Leu Lys Thr Gly Leu Gln Glu Val Glu Val
1               5                   10                  15

Lys

<210> SEQ ID NO 160
<211> LENGTH: 12
<212> TYPE: PRT
<213> ORGANISM: Homo sapiens

<400> SEQUENCE: 160

Ser Gly Ser Asp Glu Val Gln Val Gly Gln Gln Arg
1               5                   10

<210> SEQ ID NO 161
<211> LENGTH: 16
<212> TYPE: PRT
<213> ORGANISM: Homo sapiens

<400> SEQUENCE: 161
```

```
Ser Ile Asn Thr His Pro Ser Gln Lys Pro Leu Ser Ile Thr Val Arg
1               5                   10                  15

<210> SEQ ID NO 162
<211> LENGTH: 10
<212> TYPE: PRT
<213> ORGANISM: Homo sapiens

<400> SEQUENCE: 162

Val Leu Leu Asp Gly Val Gln Asn Pro Arg
1               5                   10

<210> SEQ ID NO 163
<211> LENGTH: 17
<212> TYPE: PRT
<213> ORGANISM: Homo sapiens

<400> SEQUENCE: 163

Val Val Leu Val Ser Leu Gln Ser Gly Tyr Leu Phe Ile Gln Thr Asp
1               5                   10                  15

Lys

<210> SEQ ID NO 164
<211> LENGTH: 11
<212> TYPE: PRT
<213> ORGANISM: Homo sapiens

<400> SEQUENCE: 164

Gly Gln Ile Val Phe Met Asn Arg Glu Pro Lys
1               5                   10

<210> SEQ ID NO 165
<211> LENGTH: 16
<212> TYPE: PRT
<213> ORGANISM: Homo sapiens

<400> SEQUENCE: 165

Gly Ser Gly Ala Thr Phe Ser His Tyr Tyr Met Ile Leu Ser Arg
1               5                   10                  15

<210> SEQ ID NO 166
<211> LENGTH: 15
<212> TYPE: PRT
<213> ORGANISM: Homo sapiens

<400> SEQUENCE: 166

His Leu Val Pro Gly Ala Pro Phe Leu Leu Gln Ala Leu Val Arg
1               5                   10                  15

<210> SEQ ID NO 167
<211> LENGTH: 11
<212> TYPE: PRT
<213> ORGANISM: Homo sapiens

<400> SEQUENCE: 167

Leu Gly Gln Tyr Ala Ser Pro Thr Ala Lys Arg
1               5                   10

<210> SEQ ID NO 168
<211> LENGTH: 12
<212> TYPE: PRT
<213> ORGANISM: Homo sapiens

<400> SEQUENCE: 168
```

```
Leu Asn Met Gly Ile Thr Asp Leu Gln Gly Leu Arg
1               5                   10

<210> SEQ ID NO 169
<211> LENGTH: 12
<212> TYPE: PRT
<213> ORGANISM: Homo sapiens

<400> SEQUENCE: 169

Leu Val Asn Gly Gln Ser His Ile Ser Leu Ser Lys
1               5                   10

<210> SEQ ID NO 170
<211> LENGTH: 14
<212> TYPE: PRT
<213> ORGANISM: Homo sapiens

<400> SEQUENCE: 170

Pro Asn Met Ile Pro Asp Gly Asp Phe Asn Ser Tyr Val Arg
1               5                   10

<210> SEQ ID NO 171
<211> LENGTH: 41
<212> TYPE: PRT
<213> ORGANISM: Homo sapiens

<400> SEQUENCE: 171

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys Gln Arg
        35                  40

<210> SEQ ID NO 172
<211> LENGTH: 22
<212> TYPE: PRT
<213> ORGANISM: Homo sapiens

<400> SEQUENCE: 172

Ser Pro Ser Val Val His Leu Gly Val Pro Leu Ser Val Gly Val Gln
1               5                   10                  15

Leu Gln Asp Val Pro Arg
            20

<210> SEQ ID NO 173
<211> LENGTH: 13
<212> TYPE: PRT
<213> ORGANISM: Homo sapiens

<400> SEQUENCE: 173

Thr Ile Thr Val Met Val Glu Asn Ser His Gly Leu Arg
1               5                   10

<210> SEQ ID NO 174
<211> LENGTH: 11
<212> TYPE: PRT
<213> ORGANISM: Homo sapiens

<400> SEQUENCE: 174

Gly Gln Ile Val Phe Met Asn Arg Glu Pro Lys
1               5                   10
```

```
<210> SEQ ID NO 175
<211> LENGTH: 16
<212> TYPE: PRT
<213> ORGANISM: Homo sapiens

<400> SEQUENCE: 175

Gly Ser Gly Ala Thr Phe Ser His Tyr Tyr Tyr Met Ile Leu Ser Arg
1               5                   10                  15

<210> SEQ ID NO 176
<211> LENGTH: 15
<212> TYPE: PRT
<213> ORGANISM: Homo sapiens

<400> SEQUENCE: 176

His Leu Val Pro Gly Ala Pro Phe Leu Leu Gln Ala Leu Val Arg
1               5                   10                  15

<210> SEQ ID NO 177
<211> LENGTH: 11
<212> TYPE: PRT
<213> ORGANISM: Homo sapiens

<400> SEQUENCE: 177

Leu Gly Gln Tyr Ala Ser Pro Thr Ala Lys Arg
1               5                   10

<210> SEQ ID NO 178
<211> LENGTH: 12
<212> TYPE: PRT
<213> ORGANISM: Homo sapiens

<400> SEQUENCE: 178

Leu Asn Met Gly Ile Thr Asp Leu Gln Gly Leu Arg
1               5                   10

<210> SEQ ID NO 179
<211> LENGTH: 27
<212> TYPE: PRT
<213> ORGANISM: Homo sapiens

<400> SEQUENCE: 179

Leu Gln Glu Thr Ser Asn Trp Leu Leu Ser Gln Gln Gln Ala Asp Gly
1               5                   10                  15

Ser Phe Gln Asp Leu Ser Pro Val Ile His Arg
            20                  25

<210> SEQ ID NO 180
<211> LENGTH: 12
<212> TYPE: PRT
<213> ORGANISM: Homo sapiens

<400> SEQUENCE: 180

Leu Val Asn Gly Gln Ser His Ile Ser Leu Ser Lys
1               5                   10

<210> SEQ ID NO 181
<211> LENGTH: 14
<212> TYPE: PRT
<213> ORGANISM: Homo sapiens

<400> SEQUENCE: 181

Pro Asn Met Ile Pro Asp Gly Asp Phe Asn Ser Tyr Val Arg
1               5                   10
```

<210> SEQ ID NO 182
<211> LENGTH: 17
<212> TYPE: PRT
<213> ORGANISM: Homo sapiens

<400> SEQUENCE: 182

Pro Val Ala Phe Ser Val Val Pro Thr Ala Ala Thr Ala Val Ser Leu
1               5                   10                  15

Lys

<210> SEQ ID NO 183
<211> LENGTH: 41
<212> TYPE: PRT
<213> ORGANISM: Homo sapiens

<400> SEQUENCE: 183

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys Gln Arg
        35                  40

<210> SEQ ID NO 184
<211> LENGTH: 22
<212> TYPE: PRT
<213> ORGANISM: Homo sapiens

<400> SEQUENCE: 184

Ser Pro Ser Val Val His Leu Gly Val Pro Leu Ser Val Gly Val Gln
1               5                   10                  15

Leu Gln Asp Val Pro Arg
            20

<210> SEQ ID NO 185
<211> LENGTH: 13
<212> TYPE: PRT
<213> ORGANISM: Homo sapiens

<400> SEQUENCE: 185

Thr Ile Thr Val Met Val Glu Asn Ser His Gly Leu Arg
1               5                   10

<210> SEQ ID NO 186
<211> LENGTH: 15
<212> TYPE: PRT
<213> ORGANISM: Homo sapiens

<400> SEQUENCE: 186

Gly Val Gly Trp Ser His Pro Leu Pro Gln Cys Glu Ile Val Lys
1               5                   10                  15

<210> SEQ ID NO 187
<211> LENGTH: 8
<212> TYPE: PRT
<213> ORGANISM: Homo sapiens

<400> SEQUENCE: 187

Ala Thr Leu Leu Asp Ile Tyr Lys
1               5

```
<210> SEQ ID NO 188
<211> LENGTH: 32
<212> TYPE: PRT
<213> ORGANISM: Homo sapiens

<400> SEQUENCE: 188

Asp Ser Leu Asp Gln Leu Val Gly Gly Val Pro Val Thr Leu Asn Ala
1               5                   10                  15

Gln Thr Ile Asp Val Asn Gln Glu Thr Ser Asp Leu Asp Pro Ser Lys
            20                  25                  30

<210> SEQ ID NO 189
<211> LENGTH: 6
<212> TYPE: PRT
<213> ORGANISM: Homo sapiens

<400> SEQUENCE: 189

Glu Ala Leu Gln Ile Lys
1               5

<210> SEQ ID NO 190
<211> LENGTH: 32
<212> TYPE: PRT
<213> ORGANISM: Homo sapiens

<400> SEQUENCE: 190

Glu Thr Val Leu Thr Phe Ile Asp Pro Glu Gly Ser Glu Val Asp Met
1               5                   10                  15

Val Glu Glu Ile Asp His Ile Gly Ile Ile Ser Phe Pro Asp Phe Lys
            20                  25                  30

<210> SEQ ID NO 191
<211> LENGTH: 12
<212> TYPE: PRT
<213> ORGANISM: Homo sapiens

<400> SEQUENCE: 191

Ile Asp Thr Gln Asp Ile Glu Ala Ser His Tyr Arg
1               5                   10

<210> SEQ ID NO 192
<211> LENGTH: 8
<212> TYPE: PRT
<213> ORGANISM: Homo sapiens

<400> SEQUENCE: 192

Lys Ile Glu Glu Ile Ala Ala Lys
1               5

<210> SEQ ID NO 193
<211> LENGTH: 12
<212> TYPE: PRT
<213> ORGANISM: Homo sapiens

<400> SEQUENCE: 193

Leu Lys Glu Gly Met Leu Ser Ile Met Ser Tyr Arg
1               5                   10

<210> SEQ ID NO 194
<211> LENGTH: 10
<212> TYPE: PRT
<213> ORGANISM: Homo sapiens

<400> SEQUENCE: 194
```

```
Leu Gln Gly Thr Leu Pro Val Glu Ala Arg
1               5                   10
```

<210> SEQ ID NO 195
<211> LENGTH: 26
<212> TYPE: PRT
<213> ORGANISM: Homo sapiens

<400> SEQUENCE: 195

```
Met Val Glu Thr Thr Ala Tyr Ala Leu Leu Thr Ser Leu Asn Leu Lys
1               5                   10                  15

Asp Ile Asn Tyr Val Asn Pro Val Ile Lys
            20                  25
```

<210> SEQ ID NO 196
<211> LENGTH: 7
<212> TYPE: PRT
<213> ORGANISM: Homo sapiens

<400> SEQUENCE: 196

```
Asn Phe Glu Ile Thr Ile Lys
1               5
```

<210> SEQ ID NO 197
<211> LENGTH: 19
<212> TYPE: PRT
<213> ORGANISM: Homo sapiens

<400> SEQUENCE: 197

```
Gln Leu Pro Gly Gly Gln Asn Pro Val Ser Tyr Val Tyr Leu Glu Val
1               5                   10                  15

Val Ser Lys
```

<210> SEQ ID NO 198
<211> LENGTH: 7
<212> TYPE: PRT
<213> ORGANISM: Homo sapiens

<400> SEQUENCE: 198

```
Gln Tyr Leu Ile Met Gly Lys
1               5
```

<210> SEQ ID NO 199
<211> LENGTH: 13
<212> TYPE: PRT
<213> ORGANISM: Homo sapiens

<400> SEQUENCE: 199

```
Thr Asp Ala Pro Asp Leu Pro Glu Glu Asn Gln Ala Arg
1               5                   10
```

<210> SEQ ID NO 200
<211> LENGTH: 11
<212> TYPE: PRT
<213> ORGANISM: Homo sapiens

<400> SEQUENCE: 200

```
Thr Leu Leu Pro Val Ser Lys Pro Glu Ile Arg
1               5                   10
```

<210> SEQ ID NO 201
<211> LENGTH: 7
<212> TYPE: PRT
<213> ORGANISM: Homo sapiens

```
<400> SEQUENCE: 201

Val Phe Gln Phe Leu Glu Lys
1               5

<210> SEQ ID NO 202
<211> LENGTH: 36
<212> TYPE: PRT
<213> ORGANISM: Homo sapiens

<400> SEQUENCE: 202

Val Gln Val Lys Asp Ser Leu Asp Gln Leu Val Gly Gly Val Pro Val
1               5                   10                  15

Thr Leu Asn Ala Gln Thr Ile Asp Val Asn Gln Glu Thr Ser Asp Leu
            20                  25                  30

Asp Pro Ser Lys
            35

<210> SEQ ID NO 203
<211> LENGTH: 8
<212> TYPE: PRT
<213> ORGANISM: Homo sapiens

<400> SEQUENCE: 203

Val Val Pro Glu Gly Val Lys Arg
1               5

<210> SEQ ID NO 204
<211> LENGTH: 7
<212> TYPE: PRT
<213> ORGANISM: Homo sapiens

<400> SEQUENCE: 204

Trp Leu Ser Glu Glu Gln Arg
1               5

<210> SEQ ID NO 205
<211> LENGTH: 7
<212> TYPE: PRT
<213> ORGANISM: Homo sapiens

<400> SEQUENCE: 205

Tyr Gly Met Trp Thr Ile Lys
1               5

<210> SEQ ID NO 206
<211> LENGTH: 6
<212> TYPE: PRT
<213> ORGANISM: Homo sapiens

<400> SEQUENCE: 206

Tyr Asn Phe Ser Phe Arg
1               5

<210> SEQ ID NO 207
<211> LENGTH: 11
<212> TYPE: PRT
<213> ORGANISM: Homo sapiens

<400> SEQUENCE: 207

Ile Gly Glu Ser Ile Glu Leu Thr Cys Pro Lys
1               5                   10
```

-continued

<210> SEQ ID NO 208
<211> LENGTH: 15
<212> TYPE: PRT
<213> ORGANISM: Homo sapiens

<400> SEQUENCE: 208

Leu Ser Glu Lys His Glu Gly Ser Phe Ile Gln Gly Ala Glu Lys
1               5                   10                  15

<210> SEQ ID NO 209
<211> LENGTH: 17
<212> TYPE: PRT
<213> ORGANISM: Homo sapiens

<400> SEQUENCE: 209

Ala Ala Ser Gly Thr Gln Asn Asn Val Leu Arg Gly Glu Pro Phe Ile
1               5                   10                  15

Arg

<210> SEQ ID NO 210
<211> LENGTH: 22
<212> TYPE: PRT
<213> ORGANISM: Homo sapiens

<400> SEQUENCE: 210

Gly Gly Gly Ala Gly Phe Ile Ser Gly Leu Ser Tyr Leu Glu Leu Asp
1               5                   10                  15

Asn Pro Ala Gly Asn Lys
            20

<210> SEQ ID NO 211
<211> LENGTH: 11
<212> TYPE: PRT
<213> ORGANISM: Homo sapiens

<400> SEQUENCE: 211

Val Leu Phe Tyr Val Asp Ser Glu Lys Leu Lys
1               5                   10

<210> SEQ ID NO 212
<211> LENGTH: 7
<212> TYPE: PRT
<213> ORGANISM: Homo sapiens

<400> SEQUENCE: 212

Ser Leu Leu Gln Pro Asn Lys
1               5

<210> SEQ ID NO 213
<211> LENGTH: 18
<212> TYPE: PRT
<213> ORGANISM: Homo sapiens

<400> SEQUENCE: 213

Tyr Asn Pro Val Val Ile Asp Phe Glu Met Gln Pro Ile His Glu Val
1               5                   10                  15

Leu Arg

<210> SEQ ID NO 214
<211> LENGTH: 36
<212> TYPE: PRT
<213> ORGANISM: Homo sapiens

<400> SEQUENCE: 214

```
Gly Gly Ala Ser Glu His Ile Thr Thr Leu Ala Tyr Gln Glu Leu Pro
1               5                   10                  15

Thr Ala Asp Leu Met Gln Glu Trp Gly Asp Ala Val Gln Tyr Asn Pro
            20                  25                  30

Ala Ile Ile Lys
        35

<210> SEQ ID NO 215
<211> LENGTH: 6
<212> TYPE: PRT
<213> ORGANISM: Homo sapiens

<400> SEQUENCE: 215

Lys Gly Val Glu Leu Lys
1               5

<210> SEQ ID NO 216
<211> LENGTH: 12
<212> TYPE: PRT
<213> ORGANISM: Homo sapiens

<400> SEQUENCE: 216

Thr Glu His Tyr Glu Glu Gln Ile Glu Ala Phe Lys
1               5                   10

<210> SEQ ID NO 217
<211> LENGTH: 9
<212> TYPE: PRT
<213> ORGANISM: Homo sapiens

<400> SEQUENCE: 217

Gly Gly Pro Phe Ser Asp Ser Tyr Arg
1               5

<210> SEQ ID NO 218
<211> LENGTH: 18
<212> TYPE: PRT
<213> ORGANISM: Homo sapiens

<400> SEQUENCE: 218

His Asp Thr Ser Leu Lys Pro Ile Ser Val Ser Tyr Asn Pro Ala Thr
1               5                   10                  15

Ala Lys

<210> SEQ ID NO 219
<211> LENGTH: 25
<212> TYPE: PRT
<213> ORGANISM: Homo sapiens

<400> SEQUENCE: 219

Ser Leu Leu Ser Asn Val Glu Gly Asp Asn Ala Val Pro Met Gln His
1               5                   10                  15

Asn Asn Arg Pro Thr Gln Pro Leu Lys
            20                  25

<210> SEQ ID NO 220
<211> LENGTH: 11
<212> TYPE: PRT
<213> ORGANISM: Homo sapiens

<400> SEQUENCE: 220

Thr Pro Asn Lys Ile Asp Leu Tyr Asp Val Arg
```

```
1               5                   10
```

<210> SEQ ID NO 221
<211> LENGTH: 7
<212> TYPE: PRT
<213> ORGANISM: Homo sapiens

<400> SEQUENCE: 221

```
Glu Arg Glu Leu Asn Gly Lys
1               5
```

<210> SEQ ID NO 222
<211> LENGTH: 19
<212> TYPE: PRT
<213> ORGANISM: Homo sapiens

<400> SEQUENCE: 222

```
Ala Phe Pro Ala Leu Thr Ser Leu Asp Leu Ser Asp Asn Pro Gly Leu
1               5                   10                  15

Gly Glu Arg
```

<210> SEQ ID NO 223
<211> LENGTH: 9
<212> TYPE: PRT
<213> ORGANISM: Homo sapiens

<400> SEQUENCE: 223

```
Ala Thr Val Asn Pro Ser Ala Pro Arg
1               5
```

<210> SEQ ID NO 224
<211> LENGTH: 10
<212> TYPE: PRT
<213> ORGANISM: Homo sapiens

<400> SEQUENCE: 224

```
Phe Pro Ala Ile Gln Asn Leu Ala Leu Arg
1               5                   10
```

<210> SEQ ID NO 225
<211> LENGTH: 21
<212> TYPE: PRT
<213> ORGANISM: Homo sapiens

<400> SEQUENCE: 225

```
Ile Thr Gly Thr Met Pro Pro Leu Pro Leu Glu Ala Thr Gly Leu Ala
1               5                   10                  15

Leu Ser Ser Leu Arg
                20
```

<210> SEQ ID NO 226
<211> LENGTH: 18
<212> TYPE: PRT
<213> ORGANISM: Homo sapiens

<400> SEQUENCE: 226

```
Leu Thr Val Gly Ala Ala Gln Val Pro Ala Gln Leu Leu Val Gly Ala
1               5                   10                  15

Leu Arg
```

<210> SEQ ID NO 227
<211> LENGTH: 15
<212> TYPE: PRT

```
<213> ORGANISM: Homo sapiens

<400> SEQUENCE: 227

Ser Trp Leu Ala Glu Leu Gln Gln Trp Leu Lys Pro Gly Leu Lys
1               5                   10                  15

<210> SEQ ID NO 228
<211> LENGTH: 14
<212> TYPE: PRT
<213> ORGANISM: Homo sapiens

<400> SEQUENCE: 228

Val His Asp Val Asn Asp Asn Trp Pro Val Phe Thr His Arg
1               5                   10

<210> SEQ ID NO 229
<211> LENGTH: 10
<212> TYPE: PRT
<213> ORGANISM: Homo sapiens

<400> SEQUENCE: 229

Ser Asp Val Asp Gln Leu Tyr Leu Ile Arg
1               5                   10

<210> SEQ ID NO 230
<211> LENGTH: 9
<212> TYPE: PRT
<213> ORGANISM: Homo sapiens

<400> SEQUENCE: 230

Trp Ile Leu Leu Glu Asp Tyr Arg Lys
1               5

<210> SEQ ID NO 231
<211> LENGTH: 7
<212> TYPE: PRT
<213> ORGANISM: Homo sapiens

<400> SEQUENCE: 231

Ala Glu Leu Glu Lys Glu Arg
1               5

<210> SEQ ID NO 232
<211> LENGTH: 24
<212> TYPE: PRT
<213> ORGANISM: Homo sapiens

<400> SEQUENCE: 232

Gln Glu Phe Gly Trp Leu Ile Pro Met Gln Leu Met Ser Tyr Pro Leu
1               5                   10                  15

Ser Glu Gly Gln Leu Asp Gln Lys
            20

<210> SEQ ID NO 233
<211> LENGTH: 11
<212> TYPE: PRT
<213> ORGANISM: Homo sapiens

<400> SEQUENCE: 233

Leu Glu Asp Ser Val Thr Tyr His Cys Ser Arg
1               5                   10

<210> SEQ ID NO 234
<211> LENGTH: 9
```

```
<212> TYPE: PRT
<213> ORGANISM: Homo sapiens

<400> SEQUENCE: 234

Leu Gln Asp Glu Asp Leu Gly Phe Leu
1               5

<210> SEQ ID NO 235
<211> LENGTH: 13
<212> TYPE: PRT
<213> ORGANISM: Homo sapiens

<400> SEQUENCE: 235

Gln Leu Asn Glu Ile Asn Tyr Glu Asp His Lys Leu Lys
1               5                   10

<210> SEQ ID NO 236
<211> LENGTH: 6
<212> TYPE: PRT
<213> ORGANISM: Homo sapiens

<400> SEQUENCE: 236

Leu Tyr Asp Val Leu Arg
1               5

<210> SEQ ID NO 237
<211> LENGTH: 9
<212> TYPE: PRT
<213> ORGANISM: Homo sapiens

<400> SEQUENCE: 237

Ile Asp Val His Leu Val Pro Asp Arg
1               5

<210> SEQ ID NO 238
<211> LENGTH: 8
<212> TYPE: PRT
<213> ORGANISM: Homo sapiens

<400> SEQUENCE: 238

Ile Val Ile Glu Tyr Val Asp Arg
1               5

<210> SEQ ID NO 239
<211> LENGTH: 6
<212> TYPE: PRT
<213> ORGANISM: Homo sapiens

<400> SEQUENCE: 239

Thr Met Phe Ile Cys Lys
1               5

<210> SEQ ID NO 240
<211> LENGTH: 14
<212> TYPE: PRT
<213> ORGANISM: Homo sapiens

<400> SEQUENCE: 240

Val Ala Asn Tyr Phe Asp Trp Ile Ser Tyr His Val Gly Arg
1               5                   10

<210> SEQ ID NO 241
<211> LENGTH: 20
<212> TYPE: PRT
<213> ORGANISM: Homo sapiens
```

<400> SEQUENCE: 241

Glu Ile Leu Val Gly Asp Val Gly Gln Thr Val Asp Asp Pro Tyr Ala
1               5                   10                  15

Thr Phe Val Lys
            20

<210> SEQ ID NO 242
<211> LENGTH: 21
<212> TYPE: PRT
<213> ORGANISM: Homo sapiens

<400> SEQUENCE: 242

Phe Thr Thr Leu Val Gln Asp Leu Ala Asn Ala Phe Gln Gln Glu Ala
1               5                   10                  15

Gln Thr Ser Gly Lys
            20

<210> SEQ ID NO 243
<211> LENGTH: 7
<212> TYPE: PRT
<213> ORGANISM: Homo sapiens

<400> SEQUENCE: 243

Lys Asp Val Val Asn Thr Lys
1               5

<210> SEQ ID NO 244
<211> LENGTH: 12
<212> TYPE: PRT
<213> ORGANISM: Homo sapiens

<400> SEQUENCE: 244

Leu Asp Thr Leu Ala Gln Glu Val Ala Leu Leu Lys
1               5                   10

<210> SEQ ID NO 245
<211> LENGTH: 6
<212> TYPE: PRT
<213> ORGANISM: Homo sapiens

<400> SEQUENCE: 245

Met Phe Glu Glu Leu Lys
1               5

<210> SEQ ID NO 246
<211> LENGTH: 14
<212> TYPE: PRT
<213> ORGANISM: Homo sapiens

<400> SEQUENCE: 246

Ser Arg Leu Asp Thr Leu Ala Gln Glu Val Ala Leu Leu Lys
1               5                   10

<210> SEQ ID NO 247
<211> LENGTH: 9
<212> TYPE: PRT
<213> ORGANISM: Homo sapiens

<400> SEQUENCE: 247

Asp Gly Ser Thr Ile Pro Ile Ala Lys
1               5

```
<210> SEQ ID NO 248
<211> LENGTH: 9
<212> TYPE: PRT
<213> ORGANISM: Homo sapiens

<400> SEQUENCE: 248

His Leu Glu Asp Val Phe Ser Lys Arg
1               5

<210> SEQ ID NO 249
<211> LENGTH: 8
<212> TYPE: PRT
<213> ORGANISM: Homo sapiens

<400> SEQUENCE: 249

Met Phe Gln Glu Ile Val His Lys
1               5

<210> SEQ ID NO 250
<211> LENGTH: 17
<212> TYPE: PRT
<213> ORGANISM: Homo sapiens

<400> SEQUENCE: 250

Tyr Val His Lys Asp Glu Thr Met Ser Pro Ser Thr Ala Phe Gln Val
1               5                   10                  15

Lys

<210> SEQ ID NO 251
<211> LENGTH: 9
<212> TYPE: PRT
<213> ORGANISM: Homo sapiens

<400> SEQUENCE: 251

Asp Tyr Glu Val Asp Ala Thr Leu Lys
1               5

<210> SEQ ID NO 252
<211> LENGTH: 13
<212> TYPE: PRT
<213> ORGANISM: Homo sapiens

<400> SEQUENCE: 252

Ser Asp Asp Glu Val Asp Pro Ala Val Glu Leu Lys
1               5                   10

<210> SEQ ID NO 253
<211> LENGTH: 14
<212> TYPE: PRT
<213> ORGANISM: Homo sapiens

<400> SEQUENCE: 253

Glu Val Gly Pro Thr Asn Ala Asp Pro Val Cys Leu Ala Lys
1               5                   10

<210> SEQ ID NO 254
<211> LENGTH: 20
<212> TYPE: PRT
<213> ORGANISM: Homo sapiens

<400> SEQUENCE: 254

Lys Leu Ile Ser Val Asp Thr Glu His Ser Asn Ile Tyr Leu Gln Asn
1               5                   10                  15

Gly Pro Asp Arg
```

```
<210> SEQ ID NO 255
<211> LENGTH: 16
<212> TYPE: PRT
<213> ORGANISM: Homo sapiens

<400> SEQUENCE: 255

Pro Asp Gln Val Asp Lys Glu Asp Glu Asp Phe Gln Glu Ser Asn Lys
1               5                   10                  15

<210> SEQ ID NO 256
<211> LENGTH: 12
<212> TYPE: PRT
<213> ORGANISM: Homo sapiens

<400> SEQUENCE: 256

Pro Val Trp Leu Gly Phe Leu Gly Pro Ile Ile Lys
1               5                   10

<210> SEQ ID NO 257
<211> LENGTH: 8
<212> TYPE: PRT
<213> ORGANISM: Homo sapiens

<400> SEQUENCE: 257

Tyr Ser Phe Thr Ile Glu Leu Arg
1               5

<210> SEQ ID NO 258
<211> LENGTH: 9
<212> TYPE: PRT
<213> ORGANISM: Homo sapiens

<400> SEQUENCE: 258

Ile Val Gln Leu Ile Gln Asp Thr Arg
1               5

<210> SEQ ID NO 259
<211> LENGTH: 14
<212> TYPE: PRT
<213> ORGANISM: Homo sapiens

<400> SEQUENCE: 259

Thr Ala Ser Thr Pro Thr Pro Asp Asp Lys Leu Phe Gln Lys
1               5                   10

<210> SEQ ID NO 260
<211> LENGTH: 12
<212> TYPE: PRT
<213> ORGANISM: Homo sapiens

<400> SEQUENCE: 260

Ala Gly Gly Ser Trp Asp Leu Ala Val Gln Glu Arg
1               5                   10

<210> SEQ ID NO 261
<211> LENGTH: 16
<212> TYPE: PRT
<213> ORGANISM: Homo sapiens

<400> SEQUENCE: 261

Leu Ser Asn Asn Ala Leu Ser Gly Leu Pro Gln Gly Val Phe Gly Lys
1               5                   10                  15
```

```
<210> SEQ ID NO 262
<211> LENGTH: 12
<212> TYPE: PRT
<213> ORGANISM: Homo sapiens

<400> SEQUENCE: 262

Cys Val Ile Ala Gly Gln Gly Val Ala Trp Thr Lys
1               5                   10

<210> SEQ ID NO 263
<211> LENGTH: 6
<212> TYPE: PRT
<213> ORGANISM: Homo sapiens

<400> SEQUENCE: 263

Ala Phe Val Phe Pro Lys
1               5

<210> SEQ ID NO 264
<211> LENGTH: 8
<212> TYPE: PRT
<213> ORGANISM: Homo sapiens

<400> SEQUENCE: 264

Ala Pro Leu Thr Lys Pro Leu Lys
1               5

<210> SEQ ID NO 265
<211> LENGTH: 10
<212> TYPE: PRT
<213> ORGANISM: Homo sapiens

<400> SEQUENCE: 265

Glu Ser Asp Thr Ser Tyr Val Ser Leu Lys
1               5                   10

<210> SEQ ID NO 266
<211> LENGTH: 10
<212> TYPE: PRT
<213> ORGANISM: Homo sapiens

<400> SEQUENCE: 266

Gly Tyr Ser Ile Phe Ser Tyr Ala Thr Lys
1               5                   10

<210> SEQ ID NO 267
<211> LENGTH: 7
<212> TYPE: PRT
<213> ORGANISM: Homo sapiens

<400> SEQUENCE: 267

Lys Ala Phe Val Phe Pro Lys
1               5

<210> SEQ ID NO 268
<211> LENGTH: 11
<212> TYPE: PRT
<213> ORGANISM: Homo sapiens

<400> SEQUENCE: 268

Gln Asp Asn Glu Ile Leu Ile Phe Trp Ser Lys
1               5                   10

<210> SEQ ID NO 269
```

```
<211> LENGTH: 12
<212> TYPE: PRT
<213> ORGANISM: Homo sapiens

<400> SEQUENCE: 269

Arg Gln Asp Asn Glu Ile Leu Ile Phe Trp Ser Lys
1               5                   10

<210> SEQ ID NO 270
<211> LENGTH: 15
<212> TYPE: PRT
<213> ORGANISM: Homo sapiens

<400> SEQUENCE: 270

Tyr Glu Val Gln Gly Glu Val Phe Thr Lys Pro Gln Leu Trp Pro
1               5                   10                  15

<210> SEQ ID NO 271
<211> LENGTH: 11
<212> TYPE: PRT
<213> ORGANISM: Homo sapiens

<400> SEQUENCE: 271

Val Phe Glu Phe Gly Gly Pro Glu Val Leu Lys
1               5                   10

<210> SEQ ID NO 272
<211> LENGTH: 9
<212> TYPE: PRT
<213> ORGANISM: Homo sapiens

<400> SEQUENCE: 272

Ala Ser Asn Asp Met Tyr His Ser Arg
1               5

<210> SEQ ID NO 273
<211> LENGTH: 17
<212> TYPE: PRT
<213> ORGANISM: Homo sapiens

<400> SEQUENCE: 273

Leu Val Gly Gly Pro Met Asp Ala Ser Val Glu Glu Gly Val Arg
1               5                   10                  15

Arg

<210> SEQ ID NO 274
<211> LENGTH: 13
<212> TYPE: PRT
<213> ORGANISM: Homo sapiens

<400> SEQUENCE: 274

Tyr Gly Asp Ser Gly Glu Gln Ile Ala Gly Phe Val Lys
1               5                   10

<210> SEQ ID NO 275
<211> LENGTH: 18
<212> TYPE: PRT
<213> ORGANISM: Homo sapiens

<400> SEQUENCE: 275

Ser Gly Val Tyr Gln His Val Thr Gly Glu Met Met Gly Gly His Ala
1               5                   10                  15

Ile Arg
```

<210> SEQ ID NO 276
<211> LENGTH: 8
<212> TYPE: PRT
<213> ORGANISM: Homo sapiens

<400> SEQUENCE: 276

Arg Ile Glu Ser Leu Ile Asp Arg
1               5

<210> SEQ ID NO 277
<211> LENGTH: 17
<212> TYPE: PRT
<213> ORGANISM: Homo sapiens

<400> SEQUENCE: 277

Leu Leu Asp Leu Ile Thr Trp Glu Leu Glu Pro Asp Gly Ala Leu Asp
1               5                   10                  15

Arg

<210> SEQ ID NO 278
<211> LENGTH: 7
<212> TYPE: PRT
<213> ORGANISM: Homo sapiens

<400> SEQUENCE: 278

Met Ile Tyr Ala Ser Ser Lys
1               5

<210> SEQ ID NO 279
<211> LENGTH: 10
<212> TYPE: PRT
<213> ORGANISM: Homo sapiens

<400> SEQUENCE: 279

Asn Leu Pro Ala Thr Asp Pro Leu Gln Arg
1               5                   10

<210> SEQ ID NO 280
<211> LENGTH: 13
<212> TYPE: PRT
<213> ORGANISM: Homo sapiens

<400> SEQUENCE: 280

Gln Thr Ser Pro Val Ser Ala Met Leu Val Leu Val Lys
1               5                   10

<210> SEQ ID NO 281
<211> LENGTH: 10
<212> TYPE: PRT
<213> ORGANISM: Homo sapiens

<400> SEQUENCE: 281

Asp Met Asn Glu Val Glu Thr Gln Phe Lys
1               5                   10

<210> SEQ ID NO 282
<211> LENGTH: 12
<212> TYPE: PRT
<213> ORGANISM: Homo sapiens

<400> SEQUENCE: 282

Gln Thr Leu Asn Ala Arg Asp Glu Ser Ile Lys Lys
1               5                   10

<210> SEQ ID NO 283
<211> LENGTH: 19
<212> TYPE: PRT
<213> ORGANISM: Homo sapiens

<400> SEQUENCE: 283

Ala Pro Ala Cys Leu Pro Glu Arg Asp Trp Ala Glu Ser Thr Leu Met
1               5                   10                  15

Thr Gln Lys

<210> SEQ ID NO 284
<211> LENGTH: 9
<212> TYPE: PRT
<213> ORGANISM: Homo sapiens

<400> SEQUENCE: 284

Met Leu Glu Val Pro Tyr Val Asp Arg
1               5

<210> SEQ ID NO 285
<211> LENGTH: 19
<212> TYPE: PRT
<213> ORGANISM: Homo sapiens

<400> SEQUENCE: 285

Glu Arg Pro Gly Val Tyr Thr Asn Val Val Gly Tyr Val Asp Trp Ile
1               5                   10                  15

Leu Glu Lys

<210> SEQ ID NO 286
<211> LENGTH: 12
<212> TYPE: PRT
<213> ORGANISM: Homo sapiens

<400> SEQUENCE: 286

Met Ala Glu Ser Gly Tyr Asp Ile Ala Leu Leu Lys
1               5                   10

<210> SEQ ID NO 287
<211> LENGTH: 20
<212> TYPE: PRT
<213> ORGANISM: Homo sapiens

<400> SEQUENCE: 287

Gly Gln Pro Ser Val Leu Gln Val Val Asn Leu Pro Ile Val Glu Arg
1               5                   10                  15

Pro Val Cys Lys
            20

<210> SEQ ID NO 288
<211> LENGTH: 20
<212> TYPE: PRT
<213> ORGANISM: Homo sapiens

<400> SEQUENCE: 288

Ile Val Glu Gly Ser Asp Ala Glu Ile Gly Met Ser Pro Trp Gln Val
1               5                   10                  15

Met Leu Phe Arg
            20

<210> SEQ ID NO 289
<211> LENGTH: 9

```
<212> TYPE: PRT
<213> ORGANISM: Homo sapiens

<400> SEQUENCE: 289

Ser Gly Ile Glu Cys Gln Leu Trp Arg
1               5

<210> SEQ ID NO 290
<211> LENGTH: 18
<212> TYPE: PRT
<213> ORGANISM: Homo sapiens

<400> SEQUENCE: 290

Ser Leu Glu Asp Lys Thr Glu Arg Glu Leu Leu Glu Ser Tyr Ile Asp
1               5                   10                  15

Gly Arg

<210> SEQ ID NO 291
<211> LENGTH: 13
<212> TYPE: PRT
<213> ORGANISM: Homo sapiens

<400> SEQUENCE: 291

Thr Ala Thr Ser Glu Tyr Gln Thr Phe Phe Asn Pro Arg
1               5                   10

<210> SEQ ID NO 292
<211> LENGTH: 7
<212> TYPE: PRT
<213> ORGANISM: Homo sapiens

<400> SEQUENCE: 292

Val Ile Asp Gln Phe Gly Glu
1               5

<210> SEQ ID NO 293
<211> LENGTH: 11
<212> TYPE: PRT
<213> ORGANISM: Homo sapiens

<400> SEQUENCE: 293

Ala Ser Glu Phe Leu Gly Tyr Trp Glu Pro Arg
1               5                   10

<210> SEQ ID NO 294
<211> LENGTH: 14
<212> TYPE: PRT
<213> ORGANISM: Homo sapiens

<400> SEQUENCE: 294

Tyr Ala Pro Ile Phe Glu Ser Asp Phe Ile Gln Ile Thr Lys
1               5                   10

<210> SEQ ID NO 295
<211> LENGTH: 11
<212> TYPE: PRT
<213> ORGANISM: Homo sapiens

<400> SEQUENCE: 295

Leu Asp Phe Ser Thr Ala Ile Leu Asp Ser Arg
1               5                   10

<210> SEQ ID NO 296
<211> LENGTH: 18
```

```
<212> TYPE: PRT
<213> ORGANISM: Homo sapiens

<400> SEQUENCE: 296

Leu Leu Phe Asp Gly Asp Ala His Leu Leu Met Ser Ile Pro Ser Pro
1               5                   10                  15
Phe Arg

<210> SEQ ID NO 297
<211> LENGTH: 11
<212> TYPE: PRT
<213> ORGANISM: Homo sapiens

<400> SEQUENCE: 297

Ala Val Val Phe Leu Glu Pro Gln Trp Tyr Arg
1               5                   10

<210> SEQ ID NO 298
<211> LENGTH: 16
<212> TYPE: PRT
<213> ORGANISM: Homo sapiens

<400> SEQUENCE: 298

Phe Ser Glu Gly Thr Ala Gly Asp Ser Leu Ser Leu His Ser Gly Arg
1               5                   10                  15

<210> SEQ ID NO 299
<211> LENGTH: 13
<212> TYPE: PRT
<213> ORGANISM: Homo sapiens

<400> SEQUENCE: 299

Met Glu Leu Glu Arg Pro Gly Gly Asn Glu Ile Thr Arg
1               5                   10

<210> SEQ ID NO 300
<211> LENGTH: 13
<212> TYPE: PRT
<213> ORGANISM: Homo sapiens

<400> SEQUENCE: 300

Met Glu Leu Glu Arg Pro Gly Gly Asn Glu Ile Thr Arg
1               5                   10

<210> SEQ ID NO 301
<211> LENGTH: 21
<212> TYPE: PRT
<213> ORGANISM: Homo sapiens

<400> SEQUENCE: 301

Asn Pro Ser Ser Ala Gly Ser Trp Asn Ser Gly Ser Ser Gly Pro Gly
1               5                   10                  15
Ser Thr Gly Asn Arg
                20

<210> SEQ ID NO 302
<211> LENGTH: 8
<212> TYPE: PRT
<213> ORGANISM: Homo sapiens

<400> SEQUENCE: 302

Ser Arg Ile Glu Val Leu Lys Arg
1               5
```

<210> SEQ ID NO 303
<211> LENGTH: 17
<212> TYPE: PRT
<213> ORGANISM: Homo sapiens

<400> SEQUENCE: 303

Met Gly Pro Thr Glu Leu Leu Ile Glu Met Glu Asp Trp Lys Gly Asp
1               5                   10                  15

Lys

<210> SEQ ID NO 304
<211> LENGTH: 14
<212> TYPE: PRT
<213> ORGANISM: Homo sapiens

<400> SEQUENCE: 304

His Leu Ile Ser Thr Gln Ser Ala Ile Pro Tyr Ala Leu Arg
1               5                   10

<210> SEQ ID NO 305
<211> LENGTH: 16
<212> TYPE: PRT
<213> ORGANISM: Homo sapiens

<400> SEQUENCE: 305

His Leu Ser Pro Thr Gly Thr Thr Glu Phe Trp Leu Gly Asn Glu Lys
1               5                   10                  15

<210> SEQ ID NO 306
<211> LENGTH: 8
<212> TYPE: PRT
<213> ORGANISM: Homo sapiens

<400> SEQUENCE: 306

Lys Met Leu Glu Glu Ile Met Lys
1               5

<210> SEQ ID NO 307
<211> LENGTH: 8
<212> TYPE: PRT
<213> ORGANISM: Homo sapiens

<400> SEQUENCE: 307

Met Ile Asp Ala Ala Thr Leu Lys
1               5

<210> SEQ ID NO 308
<211> LENGTH: 8
<212> TYPE: PRT
<213> ORGANISM: Homo sapiens

<400> SEQUENCE: 308

Met Ile Asp Ala Ala Thr Leu Lys
1               5

<210> SEQ ID NO 309
<211> LENGTH: 6
<212> TYPE: PRT
<213> ORGANISM: Homo sapiens

<400> SEQUENCE: 309

Lys Asp Pro Tyr Ser Arg
1               5

<210> SEQ ID NO 310
<211> LENGTH: 6
<212> TYPE: PRT
<213> ORGANISM: Homo sapiens

<400> SEQUENCE: 310

Thr Val Ser Ile Pro Arg
1               5

<210> SEQ ID NO 311
<211> LENGTH: 16
<212> TYPE: PRT
<213> ORGANISM: Homo sapiens

<400> SEQUENCE: 311

Ala Phe Gly Pro Gly Leu Gln Gly Gly Ser Ala Gly Ser Pro Ala Arg
1               5                   10                  15

<210> SEQ ID NO 312
<211> LENGTH: 14
<212> TYPE: PRT
<213> ORGANISM: Homo sapiens

<400> SEQUENCE: 312

Ala Tyr Gly Pro Gly Ile Glu Pro Thr Gly Asn Met Val Lys
1               5                   10

<210> SEQ ID NO 313
<211> LENGTH: 12
<212> TYPE: PRT
<213> ORGANISM: Homo sapiens

<400> SEQUENCE: 313

Gly Lys Leu Asp Val Gln Phe Ser Gly Leu Thr Lys
1               5                   10

<210> SEQ ID NO 314
<211> LENGTH: 13
<212> TYPE: PRT
<213> ORGANISM: Homo sapiens

<400> SEQUENCE: 314

Ile Ala Asn Leu Gln Thr Asp Leu Ser Asp Gly Leu Arg
1               5                   10

<210> SEQ ID NO 315
<211> LENGTH: 8
<212> TYPE: PRT
<213> ORGANISM: Homo sapiens

<400> SEQUENCE: 315

Ile Gln Gln Asn Thr Phe Thr Arg
1               5

<210> SEQ ID NO 316
<211> LENGTH: 11
<212> TYPE: PRT
<213> ORGANISM: Homo sapiens

<400> SEQUENCE: 316

Leu Ile Ala Leu Leu Glu Val Leu Ser Gln Lys
1               5                   10

<210> SEQ ID NO 317

```
<211> LENGTH: 11
<212> TYPE: PRT
<213> ORGANISM: Homo sapiens

<400> SEQUENCE: 317

Leu Pro Gln Leu Pro Ile Thr Asn Phe Ser Arg
1               5                   10

<210> SEQ ID NO 318
<211> LENGTH: 16
<212> TYPE: PRT
<213> ORGANISM: Homo sapiens

<400> SEQUENCE: 318

Thr Gly Val Ala Val Asn Lys Pro Ala Glu Phe Thr Val Asp Ala Lys
1               5                   10                  15

<210> SEQ ID NO 319
<211> LENGTH: 12
<212> TYPE: PRT
<213> ORGANISM: Homo sapiens

<400> SEQUENCE: 319

Val Asp Val Gly Lys Asp Gln Glu Phe Thr Val Lys
1               5                   10

<210> SEQ ID NO 320
<211> LENGTH: 17
<212> TYPE: PRT
<213> ORGANISM: Homo sapiens

<400> SEQUENCE: 320

Val Thr Ala Gln Gly Pro Gly Leu Glu Pro Ser Gly Asn Ile Ala Asn
1               5                   10                  15

Lys

<210> SEQ ID NO 321
<211> LENGTH: 12
<212> TYPE: PRT
<213> ORGANISM: Homo sapiens

<400> SEQUENCE: 321

Val Thr Val Leu Phe Ala Gly Gln His Ile Ala Lys
1               5                   10

<210> SEQ ID NO 322
<211> LENGTH: 8
<212> TYPE: PRT
<213> ORGANISM: Homo sapiens

<400> SEQUENCE: 322

Ile Gln Gln Asn Thr Phe Thr Arg
1               5

<210> SEQ ID NO 323
<211> LENGTH: 11
<212> TYPE: PRT
<213> ORGANISM: Homo sapiens

<400> SEQUENCE: 323

Leu Ile Ala Leu Leu Glu Val Leu Ser Gln Lys
1               5                   10

<210> SEQ ID NO 324
```

```
<211> LENGTH: 12
<212> TYPE: PRT
<213> ORGANISM: Homo sapiens

<400> SEQUENCE: 324

Gly Ala Thr Tyr Asn Ile Ile Val Glu Ala Leu Lys
1               5                   10

<210> SEQ ID NO 325
<211> LENGTH: 7
<212> TYPE: PRT
<213> ORGANISM: Homo sapiens

<400> SEQUENCE: 325

Ile Thr Gly Tyr Ile Ile Lys
1               5

<210> SEQ ID NO 326
<211> LENGTH: 14
<212> TYPE: PRT
<213> ORGANISM: Homo sapiens

<400> SEQUENCE: 326

Ser Tyr Thr Ile Thr Gly Leu Gln Pro Gly Thr Asp Tyr Lys
1               5                   10

<210> SEQ ID NO 327
<211> LENGTH: 9
<212> TYPE: PRT
<213> ORGANISM: Homo sapiens

<400> SEQUENCE: 327

Val Gly Asp Thr Tyr Glu Arg Pro Lys
1               5

<210> SEQ ID NO 328
<211> LENGTH: 17
<212> TYPE: PRT
<213> ORGANISM: Homo sapiens

<400> SEQUENCE: 328

Val Thr Trp Ala Pro Pro Pro Ser Ile Asp Leu Thr Asn Phe Leu Val
1               5                   10                  15

Arg

<210> SEQ ID NO 329
<211> LENGTH: 9
<212> TYPE: PRT
<213> ORGANISM: Homo sapiens

<400> SEQUENCE: 329

Tyr Glu Lys Pro Gly Ser Pro Pro Arg
1               5

<210> SEQ ID NO 330
<211> LENGTH: 15
<212> TYPE: PRT
<213> ORGANISM: Homo sapiens

<400> SEQUENCE: 330

Leu Gly Gly Pro Glu Ala Gly Leu Gly Glu Tyr Leu Phe Glu Arg
1               5                   10                  15

<210> SEQ ID NO 331
```

```
<211> LENGTH: 15
<212> TYPE: PRT
<213> ORGANISM: Homo sapiens

<400> SEQUENCE: 331

Gly Ala Leu Gln Asn Ile Ile Pro Ala Ser Thr Gly Ala Ala Lys
1               5                   10                  15

<210> SEQ ID NO 332
<211> LENGTH: 28
<212> TYPE: PRT
<213> ORGANISM: Homo sapiens

<400> SEQUENCE: 332

Val Asp Ile Val Ala Ile Asn Asp Pro Phe Ile Asp Leu Asn Tyr Met
1               5                   10                  15

Val Tyr Met Phe Gln Tyr Asp Ser Thr His Gly Lys
            20                  25

<210> SEQ ID NO 333
<211> LENGTH: 12
<212> TYPE: PRT
<213> ORGANISM: Homo sapiens

<400> SEQUENCE: 333

Val Val Asp Leu Met Ala His Met Ala Ser Lys Glu
1               5                   10

<210> SEQ ID NO 334
<211> LENGTH: 9
<212> TYPE: PRT
<213> ORGANISM: Homo sapiens

<400> SEQUENCE: 334

Asp Lys Tyr Thr Phe Glu Leu Ser Arg
1               5

<210> SEQ ID NO 335
<211> LENGTH: 8
<212> TYPE: PRT
<213> ORGANISM: Homo sapiens

<400> SEQUENCE: 335

Glu Leu Ser Ser Phe Ile Asp Lys
1               5

<210> SEQ ID NO 336
<211> LENGTH: 21
<212> TYPE: PRT
<213> ORGANISM: Homo sapiens

<400> SEQUENCE: 336

Ser Ile Asn Ser Pro Pro Leu Tyr Cys Asp Ser Glu Ile Asp Ala Glu
1               5                   10                  15

Leu Lys Asn Ile Leu
            20

<210> SEQ ID NO 337
<211> LENGTH: 24
<212> TYPE: PRT
<213> ORGANISM: Homo sapiens

<400> SEQUENCE: 337

Met Phe Gln Asn Phe Pro Thr Glu Leu Leu Leu Ser Leu Ala Val Glu
```

-continued

```
                1               5                  10                  15
Pro Leu Thr Ala Asn Phe His Lys
            20

<210> SEQ ID NO 338
<211> LENGTH: 14
<212> TYPE: PRT
<213> ORGANISM: Homo sapiens

<400> SEQUENCE: 338

Thr Ala Phe Tyr Leu Ala Glu Phe Phe Val Asn Glu Ala Arg
1               5                   10

<210> SEQ ID NO 339
<211> LENGTH: 8
<212> TYPE: PRT
<213> ORGANISM: Homo sapiens

<400> SEQUENCE: 339

Leu Lys Gln Ile Gly Ala Leu Gln
1               5

<210> SEQ ID NO 340
<211> LENGTH: 10
<212> TYPE: PRT
<213> ORGANISM: Homo sapiens

<400> SEQUENCE: 340

Glu Phe Asn Thr Gln Leu Ala Gln Lys Glu
1               5                   10

<210> SEQ ID NO 341
<211> LENGTH: 10
<212> TYPE: PRT
<213> ORGANISM: Homo sapiens

<400> SEQUENCE: 341

Leu Thr Ser Leu Pro Leu Gly Ala Leu Arg
1               5                   10

<210> SEQ ID NO 342
<211> LENGTH: 12
<212> TYPE: PRT
<213> ORGANISM: Homo sapiens

<400> SEQUENCE: 342

Thr Leu Pro Pro Gly Leu Leu Thr Pro Thr Pro Lys
1               5                   10

<210> SEQ ID NO 343
<211> LENGTH: 25
<212> TYPE: PRT
<213> ORGANISM: Homo sapiens

<400> SEQUENCE: 343

Phe Gly Gly Val Leu His Leu Ser Asp Leu Asp Asp Gly Leu Asp
1               5                   10                  15

Glu Ile Ile Met Ala Ala Pro Leu Arg
            20                  25

<210> SEQ ID NO 344
<211> LENGTH: 10
<212> TYPE: PRT
<213> ORGANISM: Homo sapiens
```

<400> SEQUENCE: 344

Ile Leu Glu Gly Phe Gln Pro Ser Gly Arg
1               5                   10

<210> SEQ ID NO 345
<211> LENGTH: 10
<212> TYPE: PRT
<213> ORGANISM: Homo sapiens

<400> SEQUENCE: 345

Leu Leu Val Ala Gly Glu Gly His Thr Arg
1               5                   10

<210> SEQ ID NO 346
<211> LENGTH: 12
<212> TYPE: PRT
<213> ORGANISM: Homo sapiens

<400> SEQUENCE: 346

Lys Arg Asp Gln Thr Leu Met Leu Ser Phe Met Arg
1               5                   10

<210> SEQ ID NO 347
<211> LENGTH: 11
<212> TYPE: PRT
<213> ORGANISM: Homo sapiens

<400> SEQUENCE: 347

Ser Phe Ile Asp Leu Ala Pro Ala Ser Glu Lys
1               5                   10

<210> SEQ ID NO 348
<211> LENGTH: 13
<212> TYPE: PRT
<213> ORGANISM: Homo sapiens

<400> SEQUENCE: 348

Ala Gly Ala Leu Asn Ser Asn Asp Ala Phe Val Leu Lys
1               5                   10

<210> SEQ ID NO 349
<211> LENGTH: 11
<212> TYPE: PRT
<213> ORGANISM: Homo sapiens

<400> SEQUENCE: 349

Ala Gly Lys Glu Pro Gly Leu Gln Ile Trp Arg
1               5                   10

<210> SEQ ID NO 350
<211> LENGTH: 22
<212> TYPE: PRT
<213> ORGANISM: Homo sapiens

<400> SEQUENCE: 350

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 351
<211> LENGTH: 7
<212> TYPE: PRT

<213> ORGANISM: Homo sapiens

<400> SEQUENCE: 351

Ala Val Glu Val Leu Pro Lys
1               5

<210> SEQ ID NO 352
<211> LENGTH: 15
<212> TYPE: PRT
<213> ORGANISM: Homo sapiens

<400> SEQUENCE: 352

Asp Ser Gln Glu Glu Lys Thr Glu Ala Leu Thr Ser Ala Lys
1               5                   10                  15

<210> SEQ ID NO 353
<211> LENGTH: 11
<212> TYPE: PRT
<213> ORGANISM: Homo sapiens

<400> SEQUENCE: 353

Glu Gly Gly Gln Thr Ala Pro Ala Ser Thr Arg
1               5                   10

<210> SEQ ID NO 354
<211> LENGTH: 15
<212> TYPE: PRT
<213> ORGANISM: Homo sapiens

<400> SEQUENCE: 354

Glu Val Gln Gly Phe Glu Ser Ala Thr Phe Leu Gly Tyr Phe Lys
1               5                   10                  15

<210> SEQ ID NO 355
<211> LENGTH: 11
<212> TYPE: PRT
<213> ORGANISM: Homo sapiens

<400> SEQUENCE: 355

Gly Ala Ser Gln Ala Gly Ala Pro Gln Gly Arg
1               5                   10

<210> SEQ ID NO 356
<211> LENGTH: 8
<212> TYPE: PRT
<213> ORGANISM: Homo sapiens

<400> SEQUENCE: 356

Gly Gly Val Ala Ser Gly Phe Lys
1               5

<210> SEQ ID NO 357
<211> LENGTH: 11
<212> TYPE: PRT
<213> ORGANISM: Homo sapiens

<400> SEQUENCE: 357

His Val Val Pro Asn Glu Val Val Val Gln Arg
1               5                   10

<210> SEQ ID NO 358
<211> LENGTH: 30
<212> TYPE: PRT
<213> ORGANISM: Homo sapiens

<400> SEQUENCE: 358

```
Ile Glu Gly Ser Asn Lys Val Pro Val Asp Pro Ala Thr Tyr Gly Gln
1               5                   10                  15

Phe Tyr Gly Gly Asp Ser Tyr Ile Ile Leu Tyr Asn Tyr Arg
            20                  25                  30
```

<210> SEQ ID NO 359
<211> LENGTH: 7
<212> TYPE: PRT
<213> ORGANISM: Homo sapiens

<400> SEQUENCE: 359

```
Met Asp Ala His Pro Pro Arg
1               5
```

<210> SEQ ID NO 360
<211> LENGTH: 18
<212> TYPE: PRT
<213> ORGANISM: Homo sapiens

<400> SEQUENCE: 360

```
Pro Ala Leu Pro Ala Gly Thr Glu Asp Thr Ala Lys Glu Asp Ala Ala
1               5                   10                  15

Asn Arg
```

<210> SEQ ID NO 361
<211> LENGTH: 17
<212> TYPE: PRT
<213> ORGANISM: Homo sapiens

<400> SEQUENCE: 361

```
Gln Thr Gln Val Ser Val Leu Pro Glu Gly Gly Glu Thr Pro Leu Phe
1               5                   10                  15

Lys
```

<210> SEQ ID NO 362
<211> LENGTH: 10
<212> TYPE: PRT
<213> ORGANISM: Homo sapiens

<400> SEQUENCE: 362

```
Arg Tyr Ile Glu Thr Asp Pro Ala Asn Arg
1               5                   10
```

<210> SEQ ID NO 363
<211> LENGTH: 8
<212> TYPE: PRT
<213> ORGANISM: Homo sapiens

<400> SEQUENCE: 363

```
Thr Ala Ser Asp Phe Ile Thr Lys
1               5
```

<210> SEQ ID NO 364
<211> LENGTH: 8
<212> TYPE: PRT
<213> ORGANISM: Homo sapiens

<400> SEQUENCE: 364

```
Thr Gly Ala Gln Glu Leu Leu Arg
1               5
```

-continued

<210> SEQ ID NO 365
<211> LENGTH: 7
<212> TYPE: PRT
<213> ORGANISM: Homo sapiens

<400> SEQUENCE: 365

Thr Pro Ile Thr Val Val Lys
1               5

<210> SEQ ID NO 366
<211> LENGTH: 18
<212> TYPE: PRT
<213> ORGANISM: Homo sapiens

<400> SEQUENCE: 366

Thr Pro Ser Ala Ala Tyr Leu Trp Val Gly Thr Gly Ala Ser Glu Ala
1               5                   10                  15

Glu Lys

<210> SEQ ID NO 367
<211> LENGTH: 26
<212> TYPE: PRT
<213> ORGANISM: Homo sapiens

<400> SEQUENCE: 367

Thr Pro Ser Ala Ala Tyr Leu Trp Val Gly Thr Gly Ala Ser Glu Ala
1               5                   10                  15

Glu Lys Thr Gly Ala Gln Glu Leu Leu Arg
            20                  25

<210> SEQ ID NO 368
<211> LENGTH: 18
<212> TYPE: PRT
<213> ORGANISM: Homo sapiens

<400> SEQUENCE: 368

Val Pro Glu Ala Arg Pro Asn Ser Met Val Val Glu His Pro Glu Phe
1               5                   10                  15

Leu Lys

<210> SEQ ID NO 369
<211> LENGTH: 28
<212> TYPE: PRT
<213> ORGANISM: Homo sapiens

<400> SEQUENCE: 369

Val Pro Phe Asp Ala Ala Thr Leu His Thr Ser Thr Ala Met Ala Ala
1               5                   10                  15

Gln His Gly Met Asp Asp Asp Gly Thr Gly Gln Lys
            20                  25

<210> SEQ ID NO 370
<211> LENGTH: 9
<212> TYPE: PRT
<213> ORGANISM: Homo sapiens

<400> SEQUENCE: 370

Tyr Ile Glu Thr Asp Pro Ala Asn Arg
1               5

<210> SEQ ID NO 371
<211> LENGTH: 12
<212> TYPE: PRT

-continued

<213> ORGANISM: Homo sapiens

<400> SEQUENCE: 371

Ile Gln Asp Leu Glu Thr Glu Asn Met Glu Leu Lys
1               5                   10

<210> SEQ ID NO 372
<211> LENGTH: 9
<212> TYPE: PRT
<213> ORGANISM: Homo sapiens

<400> SEQUENCE: 372

Met Phe Leu Ser Phe Pro Thr Thr Lys
1               5

<210> SEQ ID NO 373
<211> LENGTH: 9
<212> TYPE: PRT
<213> ORGANISM: Homo sapiens

<400> SEQUENCE: 373

Asn Lys Asp Ser Asn Ser Ile Ile Lys
1               5

<210> SEQ ID NO 374
<211> LENGTH: 11
<212> TYPE: PRT
<213> ORGANISM: Homo sapiens

<400> SEQUENCE: 374

Glu Ala Leu Val Pro Leu Val Ala Asp His Lys
1               5                   10

<210> SEQ ID NO 375
<211> LENGTH: 9
<212> TYPE: PRT
<213> ORGANISM: Homo sapiens

<400> SEQUENCE: 375

Met Lys Val Asp Met Asp Ile Cys Arg
1               5

<210> SEQ ID NO 376
<211> LENGTH: 10
<212> TYPE: PRT
<213> ORGANISM: Homo sapiens

<400> SEQUENCE: 376

His Tyr Glu Gly Ser Thr Val Pro Glu Lys
1               5                   10

<210> SEQ ID NO 377
<211> LENGTH: 14
<212> TYPE: PRT
<213> ORGANISM: Homo sapiens

<400> SEQUENCE: 377

Leu Arg Thr Glu Gly Asp Gly Val Tyr Thr Leu Asn Asp Lys
1               5                   10

<210> SEQ ID NO 378
<211> LENGTH: 11
<212> TYPE: PRT
<213> ORGANISM: Homo sapiens

```
<400> SEQUENCE: 378

Pro Glu Cys Glu Ala Val Cys Gly Lys Pro Lys
1               5                   10

<210> SEQ ID NO 379
<211> LENGTH: 14
<212> TYPE: PRT
<213> ORGANISM: Homo sapiens

<400> SEQUENCE: 379

Leu Arg Thr Glu Gly Asp Gly Val Tyr Thr Leu Asn Asp Lys
1               5                   10

<210> SEQ ID NO 380
<211> LENGTH: 11
<212> TYPE: PRT
<213> ORGANISM: Homo sapiens

<400> SEQUENCE: 380

Pro Glu Cys Glu Ala Val Cys Gly Lys Pro Lys
1               5                   10

<210> SEQ ID NO 381
<211> LENGTH: 24
<212> TYPE: PRT
<213> ORGANISM: Homo sapiens

<400> SEQUENCE: 381

Glu Val Gly Thr Pro His Gly Ile Ile Leu Asp Ser Val Asp Ala Ala
1               5                   10                  15

Phe Ile Cys Pro Gly Ser Ser Arg
            20

<210> SEQ ID NO 382
<211> LENGTH: 9
<212> TYPE: PRT
<213> ORGANISM: Homo sapiens

<400> SEQUENCE: 382

Val Asp Gly Ala Leu Cys Met Glu Lys
1               5

<210> SEQ ID NO 383
<211> LENGTH: 11
<212> TYPE: PRT
<213> ORGANISM: Homo sapiens

<400> SEQUENCE: 383

Tyr Tyr Cys Phe Gln Gly Asn Gln Phe Leu Arg
1               5                   10

<210> SEQ ID NO 384
<211> LENGTH: 11
<212> TYPE: PRT
<213> ORGANISM: Homo sapiens

<400> SEQUENCE: 384

Asp Val Glu Ala Leu Asp Leu Glu Ser Pro Lys
1               5                   10

<210> SEQ ID NO 385
<211> LENGTH: 12
<212> TYPE: PRT
<213> ORGANISM: Homo sapiens
```

<400> SEQUENCE: 385

Asp Ala Gly Thr Ile Ala Gly Leu Asn Val Leu Arg
1               5                   10

<210> SEQ ID NO 386
<211> LENGTH: 16
<212> TYPE: PRT
<213> ORGANISM: Homo sapiens

<400> SEQUENCE: 386

Asn Gln Val Ala Met Asn Pro Thr Asn Thr Val Phe Asp Ala Lys Arg
1               5                   10                  15

<210> SEQ ID NO 387
<211> LENGTH: 10
<212> TYPE: PRT
<213> ORGANISM: Homo sapiens

<400> SEQUENCE: 387

Leu Leu Gly Ile Glu Thr Pro Leu Pro Lys
1               5                   10

<210> SEQ ID NO 388
<211> LENGTH: 14
<212> TYPE: PRT
<213> ORGANISM: Homo sapiens

<400> SEQUENCE: 388

Val Glu Leu Ala Pro Leu Pro Ser Trp Gln Pro Val Gly Lys
1               5                   10

<210> SEQ ID NO 389
<211> LENGTH: 13
<212> TYPE: PRT
<213> ORGANISM: Homo sapiens

<400> SEQUENCE: 389

Arg Leu Glu Met Tyr Cys Ala Pro Leu Lys Pro Ala Lys
1               5                   10

<210> SEQ ID NO 390
<211> LENGTH: 16
<212> TYPE: PRT
<213> ORGANISM: Homo sapiens

<400> SEQUENCE: 390

Leu Ala Tyr Leu Gln Pro Ala Leu Phe Ser Gly Leu Ala Glu Leu Arg
1               5                   10                  15

<210> SEQ ID NO 391
<211> LENGTH: 15
<212> TYPE: PRT
<213> ORGANISM: Homo sapiens

<400> SEQUENCE: 391

Asn Leu Ile Ala Ala Val Ala Pro Gly Ala Phe Leu Gly Leu Lys
1               5                   10                  15

<210> SEQ ID NO 392
<211> LENGTH: 12
<212> TYPE: PRT
<213> ORGANISM: Homo sapiens

<400> SEQUENCE: 392

```
Gly Gly Lys His His Leu Gly Leu Glu Glu Pro Lys
1               5                   10

<210> SEQ ID NO 393
<211> LENGTH: 15
<212> TYPE: PRT
<213> ORGANISM: Homo sapiens

<400> SEQUENCE: 393

His Leu Asp Ser Val Leu Gln Gln Leu Gln Thr Glu Val Tyr Arg
1               5                   10                  15

<210> SEQ ID NO 394
<211> LENGTH: 11
<212> TYPE: PRT
<213> ORGANISM: Homo sapiens

<400> SEQUENCE: 394

Leu Ile Cys Gln Ala Thr Gly Phe Ser Pro Arg
1               5                   10

<210> SEQ ID NO 395
<211> LENGTH: 20
<212> TYPE: PRT
<213> ORGANISM: Homo sapiens

<400> SEQUENCE: 395

Ala Thr Leu Val Cys Leu Ile Ser Asp Phe Tyr Pro Gly Ala Val Thr
1               5                   10                  15

Val Ala Trp Lys
            20

<210> SEQ ID NO 396
<211> LENGTH: 9
<212> TYPE: PRT
<213> ORGANISM: Homo sapiens

<400> SEQUENCE: 396

Phe Ser Gly Ser Leu Leu Gly Gly Lys
1               5

<210> SEQ ID NO 397
<211> LENGTH: 11
<212> TYPE: PRT
<213> ORGANISM: Homo sapiens

<400> SEQUENCE: 397

Asn Val Gly Ser Gln Thr Leu Gln Thr Phe Lys
1               5                   10

<210> SEQ ID NO 398
<211> LENGTH: 10
<212> TYPE: PRT
<213> ORGANISM: Homo sapiens

<400> SEQUENCE: 398

Asp Thr Ala Val Asp Gly Val Phe Ile Arg
1               5                   10

<210> SEQ ID NO 399
<211> LENGTH: 9
<212> TYPE: PRT
<213> ORGANISM: Homo sapiens
```

<400> SEQUENCE: 399

Glu Leu Ala Ala Gln Thr Ile Lys Lys
1               5

<210> SEQ ID NO 400
<211> LENGTH: 10
<212> TYPE: PRT
<213> ORGANISM: Homo sapiens

<400> SEQUENCE: 400

Glu Val Ala Phe Asp Leu Glu Ile Pro Lys
1               5                   10

<210> SEQ ID NO 401
<211> LENGTH: 18
<212> TYPE: PRT
<213> ORGANISM: Homo sapiens

<400> SEQUENCE: 401

Phe Ala His Tyr Val Val Thr Ser Gln Val Val Asn Thr Ala Asn Glu
1               5                   10                  15

Ala Arg

<210> SEQ ID NO 402
<211> LENGTH: 10
<212> TYPE: PRT
<213> ORGANISM: Homo sapiens

<400> SEQUENCE: 402

Gly His Met Leu Glu Asn His Val Glu Arg
1               5                   10

<210> SEQ ID NO 403
<211> LENGTH: 37
<212> TYPE: PRT
<213> ORGANISM: Homo sapiens

<400> SEQUENCE: 403

Gly Ile Glu Ile Leu Asn Gln Val Gln Glu Ser Leu Pro Glu Leu Ser
1               5                   10                  15

Asn His Ala Ser Ile Leu Ile Met Leu Thr Asp Gly Asp Pro Thr Glu
                20                  25                  30

Gly Val Thr Asp Arg
            35

<210> SEQ ID NO 404
<211> LENGTH: 28
<212> TYPE: PRT
<213> ORGANISM: Homo sapiens

<400> SEQUENCE: 404

Gly Met Ala Asp Gln Asp Gly Leu Lys Pro Thr Ile Asp Lys Pro Ser
1               5                   10                  15

Glu Asp Ser Pro Pro Leu Glu Met Leu Gly Pro Arg
                20                  25

<210> SEQ ID NO 405
<211> LENGTH: 19
<212> TYPE: PRT
<213> ORGANISM: Homo sapiens

<400> SEQUENCE: 405

```
Gly Ser Leu Val Gln Ala Ser Glu Ala Asn Leu Gln Ala Ala Gln Asp
1               5                   10                  15

Phe Val Arg

<210> SEQ ID NO 406
<211> LENGTH: 10
<212> TYPE: PRT
<213> ORGANISM: Homo sapiens

<400> SEQUENCE: 406

Ile Ala Asp Asn Lys Gln Ser Ser Phe Lys
1               5                   10

<210> SEQ ID NO 407
<211> LENGTH: 19
<212> TYPE: PRT
<213> ORGANISM: Homo sapiens

<400> SEQUENCE: 407

Ile Leu Gly Asp Met Gln Pro Gly Asp Tyr Phe Asp Leu Val Leu Phe
1               5                   10                  15

Gly Thr Arg

<210> SEQ ID NO 408
<211> LENGTH: 13
<212> TYPE: PRT
<213> ORGANISM: Homo sapiens

<400> SEQUENCE: 408

Lys Ala Ala Ile Ser Gly Glu Asn Ala Gly Leu Val Arg
1               5                   10

<210> SEQ ID NO 409
<211> LENGTH: 17
<212> TYPE: PRT
<213> ORGANISM: Homo sapiens

<400> SEQUENCE: 409

Met Ser Leu Asp Tyr Gly Phe Val Thr Pro Leu Thr Ser Met Ser Ile
1               5                   10                  15

Arg

<210> SEQ ID NO 410
<211> LENGTH: 17
<212> TYPE: PRT
<213> ORGANISM: Homo sapiens

<400> SEQUENCE: 410

Met Ser Leu Asp Tyr Gly Phe Val Thr Pro Leu Thr Ser Met Ser Ile
1               5                   10                  15

Arg

<210> SEQ ID NO 411
<211> LENGTH: 10
<212> TYPE: PRT
<213> ORGANISM: Homo sapiens

<400> SEQUENCE: 411

Asn His Met Gln Tyr Glu Ile Val Ile Lys
1               5                   10

<210> SEQ ID NO 412
```

```
<211> LENGTH: 13
<212> TYPE: PRT
<213> ORGANISM: Homo sapiens

<400> SEQUENCE: 412

Gln Ala Val Asp Thr Ala Val Asp Gly Val Phe Ile Arg
1               5                   10

<210> SEQ ID NO 413
<211> LENGTH: 13
<212> TYPE: PRT
<213> ORGANISM: Homo sapiens

<400> SEQUENCE: 413

Gln Tyr Tyr Glu Gly Ser Glu Ile Val Val Ala Gly Arg
1               5                   10

<210> SEQ ID NO 414
<211> LENGTH: 14
<212> TYPE: PRT
<213> ORGANISM: Homo sapiens

<400> SEQUENCE: 414

Arg Gln Ala Val Asp Thr Ala Val Asp Gly Val Phe Ile Arg
1               5                   10

<210> SEQ ID NO 415
<211> LENGTH: 13
<212> TYPE: PRT
<213> ORGANISM: Homo sapiens

<400> SEQUENCE: 415

Val Thr Phe Gln Leu Thr Tyr Glu Glu Val Leu Lys Arg
1               5                   10

<210> SEQ ID NO 416
<211> LENGTH: 7
<212> TYPE: PRT
<213> ORGANISM: Homo sapiens

<400> SEQUENCE: 416

Val Thr Tyr Asp Val Ser Arg
1               5

<210> SEQ ID NO 417
<211> LENGTH: 36
<212> TYPE: PRT
<213> ORGANISM: Homo sapiens

<400> SEQUENCE: 417

Ala Ile Phe Ile Leu Asn Glu Ala Asn Asn Leu Gly Leu Leu Asp Pro
1               5                   10                  15

Asn Ser Val Ser Leu Ile Ile Leu Val Ser Asp Gly Asp Pro Thr Val
            20                  25                  30

Gly Glu Leu Lys
        35

<210> SEQ ID NO 418
<211> LENGTH: 10
<212> TYPE: PRT
<213> ORGANISM: Homo sapiens

<400> SEQUENCE: 418

Asp Lys His Ala Asp Pro Asp Phe Thr Arg
```

<210> SEQ ID NO 419
<211> LENGTH: 25
<212> TYPE: PRT
<213> ORGANISM: Homo sapiens

<400> SEQUENCE: 419

Glu Asn Ile Gln Asp Asn Ile Ser Leu Phe Ser Leu Gly Met Gly Phe
1               5                   10                  15

Asp Val Asp Tyr Asp Phe Leu Lys Arg
            20                  25

<210> SEQ ID NO 420
<211> LENGTH: 39
<212> TYPE: PRT
<213> ORGANISM: Homo sapiens

<400> SEQUENCE: 420

Phe Asp Pro Ala Lys Leu Asp Gln Ile Glu Ser Val Ile Thr Ala Thr
1               5                   10                  15

Ser Ala Asn Thr Gln Leu Val Leu Glu Thr Leu Ala Gln Met Asp Asp
            20                  25                  30

Leu Gln Asp Phe Leu Ser Lys
        35

<210> SEQ ID NO 421
<211> LENGTH: 39
<212> TYPE: PRT
<213> ORGANISM: Homo sapiens

<400> SEQUENCE: 421

Phe Asp Pro Ala Lys Leu Asp Gln Ile Glu Ser Val Ile Thr Ala Thr
1               5                   10                  15

Ser Ala Asn Thr Gln Leu Val Leu Glu Thr Leu Ala Gln Met Asp Asp
            20                  25                  30

Leu Gln Asp Phe Leu Ser Lys
        35

<210> SEQ ID NO 422
<211> LENGTH: 39
<212> TYPE: PRT
<213> ORGANISM: Homo sapiens

<400> SEQUENCE: 422

Phe Asp Pro Ala Lys Leu Asp Gln Ile Glu Ser Val Ile Thr Ala Thr
1               5                   10                  15

Ser Ala Asn Thr Gln Leu Val Leu Glu Thr Leu Ala Gln Met Asp Asp
            20                  25                  30

Leu Gln Asp Phe Leu Ser Lys
        35

<210> SEQ ID NO 423
<211> LENGTH: 20
<212> TYPE: PRT
<213> ORGANISM: Homo sapiens

<400> SEQUENCE: 423

Phe Leu His Val Pro Asp Thr Phe Glu Gly His Phe Asp Gly Val Pro
1               5                   10                  15

Val Ile Ser Lys

```
<210> SEQ ID NO 424
<211> LENGTH: 11
<212> TYPE: PRT
<213> ORGANISM: Homo sapiens

<400> SEQUENCE: 424

Phe Tyr Asn Gln Val Ser Thr Pro Leu Leu Arg
1               5                   10

<210> SEQ ID NO 425
<211> LENGTH: 8
<212> TYPE: PRT
<213> ORGANISM: Homo sapiens

<400> SEQUENCE: 425

His Ala Asp Pro Asp Phe Thr Arg
1               5

<210> SEQ ID NO 426
<211> LENGTH: 15
<212> TYPE: PRT
<213> ORGANISM: Homo sapiens

<400> SEQUENCE: 426

Ile Gln Pro Ser Gly Gly Thr Asn Ile Asn Glu Ala Leu Leu Arg
1               5                   10                  15

<210> SEQ ID NO 427
<211> LENGTH: 12
<212> TYPE: PRT
<213> ORGANISM: Homo sapiens

<400> SEQUENCE: 427

Ile Tyr Gly Asn Gln Asp Thr Ser Ser Gln Leu Lys
1               5                   10

<210> SEQ ID NO 428
<211> LENGTH: 13
<212> TYPE: PRT
<213> ORGANISM: Homo sapiens

<400> SEQUENCE: 428

Ile Tyr Gly Asn Gln Asp Thr Ser Ser Gln Leu Lys Lys
1               5                   10

<210> SEQ ID NO 429
<211> LENGTH: 7
<212> TYPE: PRT
<213> ORGANISM: Homo sapiens

<400> SEQUENCE: 429

Ile Tyr Leu Gln Pro Gly Arg
1               5

<210> SEQ ID NO 430
<211> LENGTH: 8
<212> TYPE: PRT
<213> ORGANISM: Homo sapiens

<400> SEQUENCE: 430

Lys Leu Gly Ser Tyr Glu His Arg
1               5
```

-continued

```
<210> SEQ ID NO 431
<211> LENGTH: 34
<212> TYPE: PRT
<213> ORGANISM: Homo sapiens

<400> SEQUENCE: 431

Leu Asp Gln Ile Glu Ser Val Ile Thr Ala Thr Ser Ala Asn Thr Gln
1               5                   10                  15

Leu Val Leu Glu Thr Leu Ala Gln Met Asp Asp Leu Gln Asp Phe Leu
            20                  25                  30

Ser Lys

<210> SEQ ID NO 432
<211> LENGTH: 7
<212> TYPE: PRT
<213> ORGANISM: Homo sapiens

<400> SEQUENCE: 432

Leu Gly Ser Tyr Glu His Arg
1               5

<210> SEQ ID NO 433
<211> LENGTH: 11
<212> TYPE: PRT
<213> ORGANISM: Homo sapiens

<400> SEQUENCE: 433

Leu Ser Asn Glu Asn His Gly Ile Ala Gln Arg
1               5                   10

<210> SEQ ID NO 434
<211> LENGTH: 9
<212> TYPE: PRT
<213> ORGANISM: Homo sapiens

<400> SEQUENCE: 434

Met Ala Thr Thr Met Ile Gln Ser Lys
1               5

<210> SEQ ID NO 435
<211> LENGTH: 9
<212> TYPE: PRT
<213> ORGANISM: Homo sapiens

<400> SEQUENCE: 435

Met Lys Gln Thr Val Glu Ala Met Lys
1               5

<210> SEQ ID NO 436
<211> LENGTH: 8
<212> TYPE: PRT
<213> ORGANISM: Homo sapiens

<400> SEQUENCE: 436

Asn Asp Leu Ile Ser Ala Thr Lys
1               5

<210> SEQ ID NO 437
<211> LENGTH: 28
<212> TYPE: PRT
<213> ORGANISM: Homo sapiens

<400> SEQUENCE: 437
```

-continued

Asn Val Lys Glu Asn Ile Gln Asp Asn Ile Ser Leu Phe Ser Leu Gly
1               5                   10                  15

Met Gly Phe Asp Val Asp Tyr Asp Phe Leu Lys Arg
            20                  25

<210> SEQ ID NO 438
<211> LENGTH: 33
<212> TYPE: PRT
<213> ORGANISM: Homo sapiens

<400> SEQUENCE: 438

Asn Val Gln Phe Asn Tyr Pro His Thr Ser Val Thr Asp Val Thr Gln
1               5                   10                  15

Asn Asn Phe His Asn Tyr Phe Gly Gly Ser Glu Ile Val Val Ala Gly
            20                  25                  30

Lys

<210> SEQ ID NO 439
<211> LENGTH: 13
<212> TYPE: PRT
<213> ORGANISM: Homo sapiens

<400> SEQUENCE: 439

Pro Ser Gly Gly Thr Asn Ile Asn Glu Ala Leu Leu Arg
1               5                   10

<210> SEQ ID NO 440
<211> LENGTH: 10
<212> TYPE: PRT
<213> ORGANISM: Homo sapiens

<400> SEQUENCE: 440

Ser Ser Ala Leu Asp Met Glu Asn Phe Arg
1               5                   10

<210> SEQ ID NO 441
<211> LENGTH: 10
<212> TYPE: PRT
<213> ORGANISM: Homo sapiens

<400> SEQUENCE: 441

Ser Ser Ala Leu Asp Met Glu Asn Phe Arg
1               5                   10

<210> SEQ ID NO 442
<211> LENGTH: 6
<212> TYPE: PRT
<213> ORGANISM: Homo sapiens

<400> SEQUENCE: 442

Thr Ala Gly Leu Val Arg
1               5

<210> SEQ ID NO 443
<211> LENGTH: 10
<212> TYPE: PRT
<213> ORGANISM: Homo sapiens

<400> SEQUENCE: 443

Thr Glu Val Asn Val Leu Pro Gly Ala Lys
1               5                   10

<210> SEQ ID NO 444

```
<211> LENGTH: 22
<212> TYPE: PRT
<213> ORGANISM: Homo sapiens

<400> SEQUENCE: 444

Thr Ile Leu Asp Asp Leu Arg Ala Glu Asp His Phe Ser Val Ile Asp
1               5                   10                  15

Phe Asn Gln Asn Ile Arg
            20

<210> SEQ ID NO 445
<211> LENGTH: 11
<212> TYPE: PRT
<213> ORGANISM: Homo sapiens

<400> SEQUENCE: 445

Thr Trp Arg Asn Asp Leu Ile Ser Ala Thr Lys
1               5                   10

<210> SEQ ID NO 446
<211> LENGTH: 11
<212> TYPE: PRT
<213> ORGANISM: Homo sapiens

<400> SEQUENCE: 446

Val Gln Phe Glu Leu His Tyr Gln Glu Val Lys
1               5                   10

<210> SEQ ID NO 447
<211> LENGTH: 8
<212> TYPE: PRT
<213> ORGANISM: Homo sapiens

<400> SEQUENCE: 447

Val Gln Ser Thr Ile Thr Ser Arg
1               5

<210> SEQ ID NO 448
<211> LENGTH: 19
<212> TYPE: PRT
<213> ORGANISM: Homo sapiens

<400> SEQUENCE: 448

Val Val Asn Asn Ser Pro Gln Pro Gln Asn Val Val Phe Asp Val Gln
1               5                   10                  15

Ile Pro Lys

<210> SEQ ID NO 449
<211> LENGTH: 10
<212> TYPE: PRT
<213> ORGANISM: Homo sapiens

<400> SEQUENCE: 449

Ala Arg Glu Glu His Arg Ile Pro Glu Arg
1               5                   10

<210> SEQ ID NO 450
<211> LENGTH: 27
<212> TYPE: PRT
<213> ORGANISM: Homo sapiens

<400> SEQUENCE: 450

Glu Ser Pro Gly Asn Val Gln Ile Val Asn Gly Tyr Phe Val His Phe
1               5                   10                  15
```

Phe Ala Pro Gln Gly Leu Pro Val Val Pro Lys
            20                  25

<210> SEQ ID NO 451
<211> LENGTH: 19
<212> TYPE: PRT
<213> ORGANISM: Homo sapiens

<400> SEQUENCE: 451

Met Ser Ala Gln Thr His Gly Leu Leu Gly Gln Phe Phe Gln Pro Phe
1               5                   10                  15

Asp Phe Lys

<210> SEQ ID NO 452
<211> LENGTH: 16
<212> TYPE: PRT
<213> ORGANISM: Homo sapiens

<400> SEQUENCE: 452

Ser Met Glu Asp Lys Gly Met Thr Asn Ile Asn Asp Gly Leu Leu Arg
1               5                   10                  15

<210> SEQ ID NO 453
<211> LENGTH: 6
<212> TYPE: PRT
<213> ORGANISM: Homo sapiens

<400> SEQUENCE: 453

Thr Ala Gly Leu Val Lys
1               5

<210> SEQ ID NO 454
<211> LENGTH: 20
<212> TYPE: PRT
<213> ORGANISM: Homo sapiens

<400> SEQUENCE: 454

Val Ser Asp Ile Arg Pro Gly Ser Asp Pro Thr Lys Pro Asp Ala Thr
1               5                   10                  15

Leu Val Val Lys
            20

<210> SEQ ID NO 455
<211> LENGTH: 9
<212> TYPE: PRT
<213> ORGANISM: Homo sapiens

<400> SEQUENCE: 455

Phe Ala His Thr Val Val Thr Ser Arg
1               5

<210> SEQ ID NO 456
<211> LENGTH: 8
<212> TYPE: PRT
<213> ORGANISM: Homo sapiens

<400> SEQUENCE: 456

Ile Leu Asp Asp Leu Ser Pro Arg
1               5

<210> SEQ ID NO 457
<211> LENGTH: 8
<212> TYPE: PRT

<213> ORGANISM: Homo sapiens

<400> SEQUENCE: 457

Asn Val Val Phe Val Ile Asp Lys
1               5

<210> SEQ ID NO 458
<211> LENGTH: 6
<212> TYPE: PRT
<213> ORGANISM: Homo sapiens

<400> SEQUENCE: 458

Ser Ala Gly Leu Val Lys
1               5

<210> SEQ ID NO 459
<211> LENGTH: 7
<212> TYPE: PRT
<213> ORGANISM: Homo sapiens

<400> SEQUENCE: 459

Leu His Asp Ser Asn Ser Lys
1               5

<210> SEQ ID NO 460
<211> LENGTH: 11
<212> TYPE: PRT
<213> ORGANISM: Homo sapiens

<400> SEQUENCE: 460

Tyr Ser Pro Gly Gly Thr Pro Thr Ala Ile Lys
1               5                   10

<210> SEQ ID NO 461
<211> LENGTH: 13
<212> TYPE: PRT
<213> ORGANISM: Homo sapiens

<400> SEQUENCE: 461

Ala Ala Thr Gly Glu Cys Thr Ala Thr Val Gly Lys Arg
1               5                   10

<210> SEQ ID NO 462
<211> LENGTH: 8
<212> TYPE: PRT
<213> ORGANISM: Homo sapiens

<400> SEQUENCE: 462

Ala Val Asp Ala Ala Leu Lys Lys
1               5

<210> SEQ ID NO 463
<211> LENGTH: 19
<212> TYPE: PRT
<213> ORGANISM: Homo sapiens

<400> SEQUENCE: 463

Asp Ile Pro Thr Asn Ser Pro Glu Leu Glu Glu Thr Leu Thr His Thr
1               5                   10                  15

Ile Thr Lys

<210> SEQ ID NO 464
<211> LENGTH: 9
<212> TYPE: PRT

-continued

<213> ORGANISM: Homo sapiens

<400> SEQUENCE: 464

Lys Tyr Phe Ile Asp Phe Val Ala Arg
1               5

<210> SEQ ID NO 465
<211> LENGTH: 9
<212> TYPE: PRT
<213> ORGANISM: Homo sapiens

<400> SEQUENCE: 465

Gln Val Val Ala Gly Leu Asn Phe Arg
1               5

<210> SEQ ID NO 466
<211> LENGTH: 12
<212> TYPE: PRT
<213> ORGANISM: Homo sapiens

<400> SEQUENCE: 466

Ser Val Ser Glu Ile Asn Pro Thr Thr Gln Met Lys
1               5                   10

<210> SEQ ID NO 467
<211> LENGTH: 8
<212> TYPE: PRT
<213> ORGANISM: Homo sapiens

<400> SEQUENCE: 467

Tyr Phe Ile Asp Phe Val Ala Arg
1               5

<210> SEQ ID NO 468
<211> LENGTH: 19
<212> TYPE: PRT
<213> ORGANISM: Homo sapiens

<400> SEQUENCE: 468

Gly Ser Leu Gly Gly Gly Phe Ser Ser Gly Gly Phe Ser Gly Gly Ser
1               5                   10                  15

Phe Ser Arg

<210> SEQ ID NO 469
<211> LENGTH: 19
<212> TYPE: PRT
<213> ORGANISM: Homo sapiens

<400> SEQUENCE: 469

Ser Lys Glu Leu Thr Thr Glu Ile Asp Asn Asn Ile Glu Gln Ile Ser
1               5                   10                  15

Ser Tyr Lys

<210> SEQ ID NO 470
<211> LENGTH: 9
<212> TYPE: PRT
<213> ORGANISM: Homo sapiens

<400> SEQUENCE: 470

Val Thr Met Gln Asn Leu Asn Asp Arg
1               5

<210> SEQ ID NO 471

-continued

```
<211> LENGTH: 21
<212> TYPE: PRT
<213> ORGANISM: Homo sapiens

<400> SEQUENCE: 471

Asn Leu Asp Leu Asp Ser Ile Ile Ala Glu Val Lys Ala Gln Tyr Glu
1               5                   10                  15

Glu Ile Ala Gln Arg
            20

<210> SEQ ID NO 472
<211> LENGTH: 12
<212> TYPE: PRT
<213> ORGANISM: Homo sapiens

<400> SEQUENCE: 472

Val Asp Leu Leu Asn Gln Glu Ile Glu Phe Leu Lys
1               5                   10

<210> SEQ ID NO 473
<211> LENGTH: 11
<212> TYPE: PRT
<213> ORGANISM: Homo sapiens

<400> SEQUENCE: 473

Ala Thr Ala Gln Met Leu Glu Val Met Phe Lys
1               5                   10

<210> SEQ ID NO 474
<211> LENGTH: 19
<212> TYPE: PRT
<213> ORGANISM: Homo sapiens

<400> SEQUENCE: 474

Gly Leu Gln Tyr Ala Ala Gln Glu Gly Leu Leu Ala Leu Gln Ser Glu
1               5                   10                  15

Leu Leu Arg

<210> SEQ ID NO 475
<211> LENGTH: 9
<212> TYPE: PRT
<213> ORGANISM: Homo sapiens

<400> SEQUENCE: 475

Ile Thr Gly Phe Leu Lys Pro Gly Lys
1               5

<210> SEQ ID NO 476
<211> LENGTH: 11
<212> TYPE: PRT
<213> ORGANISM: Homo sapiens

<400> SEQUENCE: 476

Ile Thr Leu Pro Asp Phe Thr Gly Asp Leu Arg
1               5                   10

<210> SEQ ID NO 477
<211> LENGTH: 8
<212> TYPE: PRT
<213> ORGANISM: Homo sapiens

<400> SEQUENCE: 477

Ser Phe Arg Pro Phe Val Pro Arg
1               5
```

```
<210> SEQ ID NO 478
<211> LENGTH: 18
<212> TYPE: PRT
<213> ORGANISM: Homo sapiens

<400> SEQUENCE: 478

Ser Pro Val Thr Leu Leu Ala Ala Val Met Ser Leu Pro Glu Glu His
1               5                   10                  15

Asn Lys

<210> SEQ ID NO 479
<211> LENGTH: 16
<212> TYPE: PRT
<213> ORGANISM: Homo sapiens

<400> SEQUENCE: 479

Phe Ser Leu Val Gly Ile Gly Gly Gln Asp Leu Asn Glu Gly Asn Arg
1               5                   10                  15

<210> SEQ ID NO 480
<211> LENGTH: 9
<212> TYPE: PRT
<213> ORGANISM: Homo sapiens

<400> SEQUENCE: 480

Ile Lys Val Pro Val Asp Trp Asn Arg
1               5

<210> SEQ ID NO 481
<211> LENGTH: 10
<212> TYPE: PRT
<213> ORGANISM: Homo sapiens

<400> SEQUENCE: 481

Gln Phe Val Thr Ala Thr Asp Val Val Arg
1               5                   10

<210> SEQ ID NO 482
<211> LENGTH: 9
<212> TYPE: PRT
<213> ORGANISM: Homo sapiens

<400> SEQUENCE: 482

Gly Leu Thr Ser Val Ile Asn Gln Lys
1               5

<210> SEQ ID NO 483
<211> LENGTH: 14
<212> TYPE: PRT
<213> ORGANISM: Homo sapiens

<400> SEQUENCE: 483

Ile Val Ala Asp Lys Asp Tyr Ser Val Thr Ala Asn Ser Lys
1               5                   10

<210> SEQ ID NO 484
<211> LENGTH: 7
<212> TYPE: PRT
<213> ORGANISM: Homo sapiens

<400> SEQUENCE: 484

Gln Phe Leu Ile Pro Pro Lys
1               5
```

<210> SEQ ID NO 485
<211> LENGTH: 10
<212> TYPE: PRT
<213> ORGANISM: Homo sapiens

<400> SEQUENCE: 485

Gly Thr Leu Ser Thr Thr Ile Thr Gly Arg
1               5                   10

<210> SEQ ID NO 486
<211> LENGTH: 10
<212> TYPE: PRT
<213> ORGANISM: Homo sapiens

<400> SEQUENCE: 486

Gly Thr Tyr Ser Thr Thr Val Thr Gly Arg
1               5                   10

<210> SEQ ID NO 487
<211> LENGTH: 10
<212> TYPE: PRT
<213> ORGANISM: Homo sapiens

<400> SEQUENCE: 487

Leu Gly His Leu Asp Leu Ser Gly Asn Arg
1               5                   10

<210> SEQ ID NO 488
<211> LENGTH: 8
<212> TYPE: PRT
<213> ORGANISM: Homo sapiens

<400> SEQUENCE: 488

Phe Asn Ala Leu Gln Tyr Leu Arg
1               5

<210> SEQ ID NO 489
<211> LENGTH: 11
<212> TYPE: PRT
<213> ORGANISM: Homo sapiens

<400> SEQUENCE: 489

Leu Lys Glu Asp Ala Val Ser Ala Ala Phe Lys
1               5                   10

<210> SEQ ID NO 490
<211> LENGTH: 18
<212> TYPE: PRT
<213> ORGANISM: Homo sapiens

<400> SEQUENCE: 490

Leu Pro Ser Gly Leu Pro Val Ser Leu Leu Thr Leu Tyr Leu Asp Asn
1               5                   10                  15

Asn Lys

<210> SEQ ID NO 491
<211> LENGTH: 21
<212> TYPE: PRT
<213> ORGANISM: Homo sapiens

<400> SEQUENCE: 491

Asn Ile Pro Thr Val Asn Glu Asn Leu Glu Asn Tyr Tyr Leu Glu Val
1               5                   10                  15

Asn Gln Leu Glu Lys
            20

<210> SEQ ID NO 492
<211> LENGTH: 10
<212> TYPE: PRT
<213> ORGANISM: Homo sapiens

<400> SEQUENCE: 492

Asn Asn Gln Ile Asp His Ile Asp Glu Lys
1               5                   10

<210> SEQ ID NO 493
<211> LENGTH: 11
<212> TYPE: PRT
<213> ORGANISM: Homo sapiens

<400> SEQUENCE: 493

Ser Leu Glu Asp Leu Gln Leu Thr His Asn Lys
1               5                   10

<210> SEQ ID NO 494
<211> LENGTH: 14
<212> TYPE: PRT
<213> ORGANISM: Homo sapiens

<400> SEQUENCE: 494

Ser Leu Glu Tyr Leu Asp Leu Ser Phe Asn Gln Ile Ala Arg
1               5                   10

<210> SEQ ID NO 495
<211> LENGTH: 10
<212> TYPE: PRT
<213> ORGANISM: Homo sapiens

<400> SEQUENCE: 495

Ser Val Pro Met Val Pro Pro Gly Ile Lys
1               5                   10

<210> SEQ ID NO 496
<211> LENGTH: 10
<212> TYPE: PRT
<213> ORGANISM: Homo sapiens

<400> SEQUENCE: 496

Thr Leu Ser Asp Val Leu Gln Tyr Val Lys
1               5                   10

<210> SEQ ID NO 497
<211> LENGTH: 9
<212> TYPE: PRT
<213> ORGANISM: Homo sapiens

<400> SEQUENCE: 497

Phe Gln Ala Ser Val Ala Thr Pro Arg
1               5

<210> SEQ ID NO 498
<211> LENGTH: 7
<212> TYPE: PRT
<213> ORGANISM: Homo sapiens

<400> SEQUENCE: 498

Ile Phe Leu Cys Gln Gly Lys

```
<210> SEQ ID NO 499
<211> LENGTH: 13
<212> TYPE: PRT
<213> ORGANISM: Homo sapiens

<400> SEQUENCE: 499

Leu Asp Pro Ala Gly Ser Phe Val Pro Thr Asn Thr Lys
1               5                   10

<210> SEQ ID NO 500
<211> LENGTH: 12
<212> TYPE: PRT
<213> ORGANISM: Homo sapiens

<400> SEQUENCE: 500

Ser Phe His Ala Ala Ala Tyr Val Pro Ala Gly Arg
1               5                   10

<210> SEQ ID NO 501
<211> LENGTH: 10
<212> TYPE: PRT
<213> ORGANISM: Homo sapiens

<400> SEQUENCE: 501

Tyr Tyr Ala Phe Asp Leu Ile Ala Gln Arg
1               5                   10

<210> SEQ ID NO 502
<211> LENGTH: 9
<212> TYPE: PRT
<213> ORGANISM: Homo sapiens

<400> SEQUENCE: 502

Ile Gly Phe Pro Trp Ser Glu Ile Arg
1               5

<210> SEQ ID NO 503
<211> LENGTH: 7
<212> TYPE: PRT
<213> ORGANISM: Homo sapiens

<400> SEQUENCE: 503

Arg Leu Glu Pro Thr Ile Lys
1               5

<210> SEQ ID NO 504
<211> LENGTH: 8
<212> TYPE: PRT
<213> ORGANISM: Homo sapiens

<400> SEQUENCE: 504

Lys Glu Cys Glu Lys Glu Asn Lys
1               5

<210> SEQ ID NO 505
<211> LENGTH: 11
<212> TYPE: PRT
<213> ORGANISM: Homo sapiens

<400> SEQUENCE: 505

Asp Ser Thr Gly Thr Tyr Thr Cys Val Ala Arg
1               5                   10
```

```
<210> SEQ ID NO 506
<211> LENGTH: 13
<212> TYPE: PRT
<213> ORGANISM: Homo sapiens

<400> SEQUENCE: 506

Ile Lys Pro Ala Thr Trp Glu Thr Gly Ile Ser Met Arg
1               5                   10

<210> SEQ ID NO 507
<211> LENGTH: 7
<212> TYPE: PRT
<213> ORGANISM: Homo sapiens

<400> SEQUENCE: 507

Val Ser Asn Leu Glu Glu Arg
1               5

<210> SEQ ID NO 508
<211> LENGTH: 15
<212> TYPE: PRT
<213> ORGANISM: Homo sapiens

<400> SEQUENCE: 508

Tyr Val Gly Gly Gln Glu His Phe Ala His Leu Leu Ile Leu Arg
1               5                   10                  15

<210> SEQ ID NO 509
<211> LENGTH: 16
<212> TYPE: PRT
<213> ORGANISM: Homo sapiens

<400> SEQUENCE: 509

Val Met Val Thr Asp Phe Glu Asn Val Pro Glu Glu Asp Gly Thr Arg
1               5                   10                  15

<210> SEQ ID NO 510
<211> LENGTH: 10
<212> TYPE: PRT
<213> ORGANISM: Homo sapiens

<400> SEQUENCE: 510

Leu Phe Leu Ser Tyr Asp Tyr Ala Val Lys
1               5                   10

<210> SEQ ID NO 511
<211> LENGTH: 11
<212> TYPE: PRT
<213> ORGANISM: Homo sapiens

<400> SEQUENCE: 511

Glu Leu Ser Asp Phe Ile Ser Tyr Leu Gln Arg
1               5                   10

<210> SEQ ID NO 512
<211> LENGTH: 24
<212> TYPE: PRT
<213> ORGANISM: Homo sapiens

<400> SEQUENCE: 512

Thr Phe Ser His Glu Leu Ser Asp Phe Gly Leu Glu Ser Thr Ala Gly
1               5                   10                  15

Glu Ile Pro Val Val Ala Ile Arg
            20
```

<210> SEQ ID NO 513
<211> LENGTH: 10
<212> TYPE: PRT
<213> ORGANISM: Homo sapiens

<400> SEQUENCE: 513

Tyr Gly Val Ser Gly Tyr Pro Thr Leu Lys
1               5                   10

<210> SEQ ID NO 514
<211> LENGTH: 8
<212> TYPE: PRT
<213> ORGANISM: Homo sapiens

<400> SEQUENCE: 514

His Trp Leu Val Thr Asp Ile Lys
1               5

<210> SEQ ID NO 515
<211> LENGTH: 14
<212> TYPE: PRT
<213> ORGANISM: Homo sapiens

<400> SEQUENCE: 515

Asp Ser Leu Leu Gln Asp Gly Glu Phe Ser Met Asp Leu Arg
1               5                   10

<210> SEQ ID NO 516
<211> LENGTH: 14
<212> TYPE: PRT
<213> ORGANISM: Homo sapiens

<400> SEQUENCE: 516

Ala Gly Leu Leu Arg Pro Asp Tyr Ala Leu Leu Gly His Arg
1               5                   10

<210> SEQ ID NO 517
<211> LENGTH: 32
<212> TYPE: PRT
<213> ORGANISM: Homo sapiens

<400> SEQUENCE: 517

Glu Gly Lys Glu Tyr Gly Val Val Leu Ala Pro Asp Gly Ser Thr Val
1               5                   10                  15

Ala Val Glu Pro Leu Leu Ala Gly Leu Glu Ala Gly Leu Gln Gly Arg
            20                  25                  30

<210> SEQ ID NO 518
<211> LENGTH: 31
<212> TYPE: PRT
<213> ORGANISM: Homo sapiens

<400> SEQUENCE: 518

Arg Val Ile Asn Leu Pro Leu Asp Ser Met Ala Ala Pro Trp Glu Thr
1               5                   10                  15

Gly Asp Thr Phe Pro Asp Val Val Ala Ile Ala Pro Asp Val Arg
            20                  25                  30

<210> SEQ ID NO 519
<211> LENGTH: 8
<212> TYPE: PRT
<213> ORGANISM: Homo sapiens

```
<400> SEQUENCE: 519

Thr Phe Thr Leu Leu Asp Pro Lys
1               5

<210> SEQ ID NO 520
<211> LENGTH: 7
<212> TYPE: PRT
<213> ORGANISM: Homo sapiens

<400> SEQUENCE: 520

Trp Gly Ala Ala Pro Tyr Arg
1               5

<210> SEQ ID NO 521
<211> LENGTH: 14
<212> TYPE: PRT
<213> ORGANISM: Homo sapiens

<400> SEQUENCE: 521

Ala Gln Val Ser Pro Thr Ala Ser Asp Met Leu His Met Arg
1               5                   10

<210> SEQ ID NO 522
<211> LENGTH: 10
<212> TYPE: PRT
<213> ORGANISM: Homo sapiens

<400> SEQUENCE: 522

Leu Met Val Glu Leu His Asn Leu Tyr Arg
1               5                   10

<210> SEQ ID NO 523
<211> LENGTH: 26
<212> TYPE: PRT
<213> ORGANISM: Homo sapiens

<400> SEQUENCE: 523

Asn Arg Gln Glu Gly Leu Met Ile Ala Ser Ser Leu Leu Asn Glu Gly
1               5                   10                  15

Tyr Leu Gln Pro Ala Gly Asp Met Ser Lys
            20                  25

<210> SEQ ID NO 524
<211> LENGTH: 10
<212> TYPE: PRT
<213> ORGANISM: Homo sapiens

<400> SEQUENCE: 524

Val Ile Met Asp Tyr Glu Ser Leu Glu Lys
1               5                   10

<210> SEQ ID NO 525
<211> LENGTH: 7
<212> TYPE: PRT
<213> ORGANISM: Homo sapiens

<400> SEQUENCE: 525

Glu Ile Thr Ile His Thr Lys
1               5

<210> SEQ ID NO 526
<211> LENGTH: 23
<212> TYPE: PRT
<213> ORGANISM: Homo sapiens
```

<400> SEQUENCE: 526

Met Asp Asp Val Phe Leu Arg Cys Ile Glu Ser Asn Met Leu Thr
1               5                   10                  15

Asp Met Thr Leu Gln Gly Ile
            20

<210> SEQ ID NO 527
<211> LENGTH: 16
<212> TYPE: PRT
<213> ORGANISM: Homo sapiens

<400> SEQUENCE: 527

Asp Gly His Phe Thr Leu Phe Ala Pro Thr Asn Glu Ala Phe Glu Lys
1               5                   10                  15

<210> SEQ ID NO 528
<211> LENGTH: 6
<212> TYPE: PRT
<213> ORGANISM: Homo sapiens

<400> SEQUENCE: 528

Arg Arg Trp Ser Thr Arg
1               5

<210> SEQ ID NO 529
<211> LENGTH: 9
<212> TYPE: PRT
<213> ORGANISM: Homo sapiens

<400> SEQUENCE: 529

Asp Ser Asp Leu Tyr Ala Glu Leu Arg
1               5

<210> SEQ ID NO 530
<211> LENGTH: 9
<212> TYPE: PRT
<213> ORGANISM: Homo sapiens

<400> SEQUENCE: 530

Ile Gly Lys Pro Ala Pro Asp Phe Lys
1               5

<210> SEQ ID NO 531
<211> LENGTH: 11
<212> TYPE: PRT
<213> ORGANISM: Homo sapiens

<400> SEQUENCE: 531

Gln Ile Thr Val Asn Asp Leu Pro Val Gly Arg
1               5                   10

<210> SEQ ID NO 532
<211> LENGTH: 13
<212> TYPE: PRT
<213> ORGANISM: Homo sapiens

<400> SEQUENCE: 532

Arg Ala Pro Asp Leu Gln Asp Leu Pro Trp Gln Val Lys
1               5                   10

<210> SEQ ID NO 533
<211> LENGTH: 10
<212> TYPE: PRT

<213> ORGANISM: Homo sapiens

<400> SEQUENCE: 533

Phe Gly Thr Ile Asn Ile Val His Pro Lys
1               5                   10

<210> SEQ ID NO 534
<211> LENGTH: 15
<212> TYPE: PRT
<213> ORGANISM: Homo sapiens

<400> SEQUENCE: 534

Asn Gly Tyr Glu Leu Ser Pro Thr Ala Ala Asn Phe Thr Arg
1               5                   10                  15

<210> SEQ ID NO 535
<211> LENGTH: 23
<212> TYPE: PRT
<213> ORGANISM: Homo sapiens

<400> SEQUENCE: 535

Glu Thr Pro Pro Leu Glu Asp Leu Ala Ala Asn Gln Ser Glu Asp Pro
1               5                   10                  15

Arg Asn Gln Arg Leu Ser Lys
            20

<210> SEQ ID NO 536
<211> LENGTH: 16
<212> TYPE: PRT
<213> ORGANISM: Homo sapiens

<400> SEQUENCE: 536

Ala Pro Glu Ala Gln Val Ser Val Gln Pro Asn Phe Gln Gln Asp Lys
1               5                   10                  15

<210> SEQ ID NO 537
<211> LENGTH: 13
<212> TYPE: PRT
<213> ORGANISM: Homo sapiens

<400> SEQUENCE: 537

Val Leu Ala Lys Pro Gln Asn Thr Ala Glu Val Gln Lys
1               5                   10

<210> SEQ ID NO 538
<211> LENGTH: 17
<212> TYPE: PRT
<213> ORGANISM: Homo sapiens

<400> SEQUENCE: 538

Ala Phe Gln Pro Phe Phe Val Glu Leu Thr Met Pro Tyr Ser Val Ile
1               5                   10                  15

Arg

<210> SEQ ID NO 539
<211> LENGTH: 9
<212> TYPE: PRT
<213> ORGANISM: Homo sapiens

<400> SEQUENCE: 539

Ala Thr Val Leu Asn Tyr Leu Pro Lys
1               5

```
<210> SEQ ID NO 540
<211> LENGTH: 15
<212> TYPE: PRT
<213> ORGANISM: Homo sapiens

<400> SEQUENCE: 540

Gln Gly Ile Pro Phe Phe Ala Gln Val Leu Leu Val Asp Gly Lys
1               5                   10                  15

<210> SEQ ID NO 541
<211> LENGTH: 10
<212> TYPE: PRT
<213> ORGANISM: Homo sapiens

<400> SEQUENCE: 541

Val Val Val Gln Thr Glu Ser Gly Gly Arg
1               5                   10

<210> SEQ ID NO 542
<211> LENGTH: 10
<212> TYPE: PRT
<213> ORGANISM: Homo sapiens

<400> SEQUENCE: 542

Val Leu Asn Thr Glu Ala Asn Val Val Arg
1               5                   10

<210> SEQ ID NO 543
<211> LENGTH: 10
<212> TYPE: PRT
<213> ORGANISM: Homo sapiens

<400> SEQUENCE: 543

Phe Ser Gly Thr Trp Tyr Ala Met Ala Lys
1               5                   10

<210> SEQ ID NO 544
<211> LENGTH: 11
<212> TYPE: PRT
<213> ORGANISM: Homo sapiens

<400> SEQUENCE: 544

Leu Ile Val His Asn Gly Tyr Cys Asp Gly Arg
1               5                   10

<210> SEQ ID NO 545
<211> LENGTH: 12
<212> TYPE: PRT
<213> ORGANISM: Homo sapiens

<400> SEQUENCE: 545

Met Lys Tyr Trp Gly Val Ala Ser Phe Leu Gln Lys
1               5                   10

<210> SEQ ID NO 546
<211> LENGTH: 10
<212> TYPE: PRT
<213> ORGANISM: Homo sapiens

<400> SEQUENCE: 546

Thr Ser Gly Ile Thr Cys Ile Lys Pro Arg
1               5                   10

<210> SEQ ID NO 547
<211> LENGTH: 11
```

<212> TYPE: PRT
<213> ORGANISM: Homo sapiens

<400> SEQUENCE: 547

Lys Val Lys Glu Glu Ala Ser Ser Pro Leu Lys
1               5                   10

<210> SEQ ID NO 548
<211> LENGTH: 9
<212> TYPE: PRT
<213> ORGANISM: Homo sapiens

<400> SEQUENCE: 548

Glu Ala Asn Tyr Ile Gly Ser Asp Lys
1               5

<210> SEQ ID NO 549
<211> LENGTH: 9
<212> TYPE: PRT
<213> ORGANISM: Homo sapiens

<400> SEQUENCE: 549

Glu Ala Asn Tyr Ile Gly Ser Asp Lys
1               5

<210> SEQ ID NO 550
<211> LENGTH: 14
<212> TYPE: PRT
<213> ORGANISM: Homo sapiens

<400> SEQUENCE: 550

Glu Ala Asn Tyr Ile Gly Ser Asp Lys Tyr Phe His Ala Arg
1               5                   10

<210> SEQ ID NO 551
<211> LENGTH: 14
<212> TYPE: PRT
<213> ORGANISM: Homo sapiens

<400> SEQUENCE: 551

Glu Ala Asn Tyr Ile Gly Ser Asp Lys Tyr Phe His Ala Arg
1               5                   10

<210> SEQ ID NO 552
<211> LENGTH: 20
<212> TYPE: PRT
<213> ORGANISM: Homo sapiens

<400> SEQUENCE: 552

Phe Phe Gly His Gly Ala Glu Asp Ser Leu Ala Asp Gln Ala Ala Asn
1               5                   10                  15

Glu Trp Gly Arg
            20

<210> SEQ ID NO 553
<211> LENGTH: 13
<212> TYPE: PRT
<213> ORGANISM: Homo sapiens

<400> SEQUENCE: 553

Phe Phe Ser Phe Leu Gly Glu Ala Phe Asp Gly Ala Arg
1               5                   10

<210> SEQ ID NO 554

```
<211> LENGTH: 13
<212> TYPE: PRT
<213> ORGANISM: Homo sapiens

<400> SEQUENCE: 554

Phe Phe Ser Phe Leu Gly Glu Ala Phe Asp Gly Ala Arg
1               5                   10

<210> SEQ ID NO 555
<211> LENGTH: 16
<212> TYPE: PRT
<213> ORGANISM: Homo sapiens

<400> SEQUENCE: 555

Arg Gly Pro Gly Gly Val Trp Ala Ala Glu Ala Ile Ser Asp Ala Arg
1               5                   10                  15

<210> SEQ ID NO 556
<211> LENGTH: 15
<212> TYPE: PRT
<213> ORGANISM: Homo sapiens

<400> SEQUENCE: 556

Arg Ser Phe Phe Ser Phe Leu Gly Glu Ala Phe Asp Gly Ala Arg
1               5                   10                  15

<210> SEQ ID NO 557
<211> LENGTH: 15
<212> TYPE: PRT
<213> ORGANISM: Homo sapiens

<400> SEQUENCE: 557

Arg Ser Phe Phe Ser Phe Leu Gly Glu Ala Phe Asp Gly Ala Arg
1               5                   10                  15

<210> SEQ ID NO 558
<211> LENGTH: 14
<212> TYPE: PRT
<213> ORGANISM: Homo sapiens

<400> SEQUENCE: 558

Ser Phe Phe Ser Phe Leu Gly Glu Ala Phe Asp Gly Ala Arg
1               5                   10

<210> SEQ ID NO 559
<211> LENGTH: 14
<212> TYPE: PRT
<213> ORGANISM: Homo sapiens

<400> SEQUENCE: 559

Ser Phe Phe Ser Phe Leu Gly Glu Ala Phe Asp Gly Ala Arg
1               5                   10

<210> SEQ ID NO 560
<211> LENGTH: 17
<212> TYPE: PRT
<213> ORGANISM: Homo sapiens

<400> SEQUENCE: 560

Ser Gly Lys Asp Pro Asn His Phe Arg Pro Ala Gly Leu Pro Glu Lys
1               5                   10                  15

Tyr

<210> SEQ ID NO 561
```

```
<211> LENGTH: 11
<212> TYPE: PRT
<213> ORGANISM: Homo sapiens

<400> SEQUENCE: 561

Glu Ala Leu Gln Gly Val Gly Asp Met Gly Arg
1               5                   10

<210> SEQ ID NO 562
<211> LENGTH: 23
<212> TYPE: PRT
<213> ORGANISM: Homo sapiens

<400> SEQUENCE: 562

Val Tyr Leu Gln Gly Leu Ile Asp Tyr Tyr Leu Phe Gly Asn Ser Ser
1               5                   10                  15

Thr Val Leu Glu Asp Ser Lys
            20

<210> SEQ ID NO 563
<211> LENGTH: 7
<212> TYPE: PRT
<213> ORGANISM: Homo sapiens

<400> SEQUENCE: 563

Leu Asp Gly Ser Asp Asn Arg
1               5

<210> SEQ ID NO 564
<211> LENGTH: 16
<212> TYPE: PRT
<213> ORGANISM: Homo sapiens

<400> SEQUENCE: 564

His Asn Val Met Ile Ser Thr Glu Trp Ala Ala Pro Asn Val Leu Arg
1               5                   10                  15

<210> SEQ ID NO 565
<211> LENGTH: 15
<212> TYPE: PRT
<213> ORGANISM: Homo sapiens

<400> SEQUENCE: 565

Leu Gln Asp Val Phe Leu Leu Pro Asp Pro Ser Gly Gln Trp Arg
1               5                   10                  15

<210> SEQ ID NO 566
<211> LENGTH: 10
<212> TYPE: PRT
<213> ORGANISM: Homo sapiens

<400> SEQUENCE: 566

Leu Pro Thr Asp Ser Glu Leu Ala Pro Arg
1               5                   10

<210> SEQ ID NO 567
<211> LENGTH: 10
<212> TYPE: PRT
<213> ORGANISM: Homo sapiens

<400> SEQUENCE: 567

Gly Lys Trp Glu Arg Pro Phe Glu Val Lys
1               5                   10
```

```
<210> SEQ ID NO 568
<211> LENGTH: 15
<212> TYPE: PRT
<213> ORGANISM: Homo sapiens

<400> SEQUENCE: 568

Gly Thr Glu Ala Ala Gly Ala Met Phe Leu Glu Ala Ile Pro Met
1               5                   10                  15

<210> SEQ ID NO 569
<211> LENGTH: 15
<212> TYPE: PRT
<213> ORGANISM: Homo sapiens

<400> SEQUENCE: 569

Gly Thr Glu Ala Ala Gly Ala Met Phe Leu Glu Ala Ile Pro Met
1               5                   10                  15

<210> SEQ ID NO 570
<211> LENGTH: 10
<212> TYPE: PRT
<213> ORGANISM: Homo sapiens

<400> SEQUENCE: 570

Lys Leu Ser Ser Trp Val Leu Leu Met Lys
1               5                   10

<210> SEQ ID NO 571
<211> LENGTH: 10
<212> TYPE: PRT
<213> ORGANISM: Homo sapiens

<400> SEQUENCE: 571

Lys Leu Ser Ser Trp Val Leu Leu Met Lys
1               5                   10

<210> SEQ ID NO 572
<211> LENGTH: 14
<212> TYPE: PRT
<213> ORGANISM: Homo sapiens

<400> SEQUENCE: 572

Lys Gln Ile Asn Asp Tyr Val Glu Lys Gly Thr Gln Gly Lys
1               5                   10

<210> SEQ ID NO 573
<211> LENGTH: 10
<212> TYPE: PRT
<213> ORGANISM: Homo sapiens

<400> SEQUENCE: 573

Leu Ala Glu Phe Ala Phe Ser Leu Tyr Arg
1               5                   10

<210> SEQ ID NO 574
<211> LENGTH: 27
<212> TYPE: PRT
<213> ORGANISM: Homo sapiens

<400> SEQUENCE: 574

Leu Tyr His Ser Glu Ala Phe Thr Val Asn Phe Gly Asp Thr Glu Glu
1               5                   10                  15

Ala Lys Lys Gln Ile Asn Asp Tyr Val Glu Lys
            20                  25
```

```
<210> SEQ ID NO 575
<211> LENGTH: 12
<212> TYPE: PRT
<213> ORGANISM: Homo sapiens

<400> SEQUENCE: 575

Pro Phe Val Phe Leu Met Ile Glu Gln Asn Thr Lys
1               5                   10

<210> SEQ ID NO 576
<211> LENGTH: 12
<212> TYPE: PRT
<213> ORGANISM: Homo sapiens

<400> SEQUENCE: 576

Thr Val Asn Phe Gly Asp Thr Glu Glu Ala Lys Lys
1               5                   10

<210> SEQ ID NO 577
<211> LENGTH: 8
<212> TYPE: PRT
<213> ORGANISM: Homo sapiens

<400> SEQUENCE: 577

Asn Met Glu Val Phe Phe Pro Lys
1               5

<210> SEQ ID NO 578
<211> LENGTH: 14
<212> TYPE: PRT
<213> ORGANISM: Homo sapiens

<400> SEQUENCE: 578

Phe Glu Glu Gly Thr Glu Ala Ser Ala Ala Thr Ala Val Lys
1               5                   10

<210> SEQ ID NO 579
<211> LENGTH: 15
<212> TYPE: PRT
<213> ORGANISM: Homo sapiens

<400> SEQUENCE: 579

Ile Ile Val Pro Thr Asp Thr Gln Asn Ile Phe Phe Met Ser Lys
1               5                   10                  15

<210> SEQ ID NO 580
<211> LENGTH: 11
<212> TYPE: PRT
<213> ORGANISM: Homo sapiens

<400> SEQUENCE: 580

Pro Phe Asp Pro Gln Asp Thr His Gln Ser Arg
1               5                   10

<210> SEQ ID NO 581
<211> LENGTH: 18
<212> TYPE: PRT
<213> ORGANISM: Homo sapiens

<400> SEQUENCE: 581

Trp Val Met Val Pro Met Met Ser Leu His His Leu Thr Ile Pro Tyr
1               5                   10                  15

Phe Arg
```

<210> SEQ ID NO 582
<211> LENGTH: 21
<212> TYPE: PRT
<213> ORGANISM: Homo sapiens

<400> SEQUENCE: 582

Ala Thr Leu Asp Val Asp Glu Ala Gly Thr Glu Ala Ala Ala Ala Thr
1               5                   10                  15

Ser Phe Ala Ile Lys
            20

<210> SEQ ID NO 583
<211> LENGTH: 12
<212> TYPE: PRT
<213> ORGANISM: Homo sapiens

<400> SEQUENCE: 583

Phe Tyr Tyr Leu Ile Ala Ser Glu Thr Pro Gly Lys
1               5                   10

<210> SEQ ID NO 584
<211> LENGTH: 9
<212> TYPE: PRT
<213> ORGANISM: Homo sapiens

<400> SEQUENCE: 584

Leu Gly Phe Thr Asp Leu Phe Ser Lys
1               5

<210> SEQ ID NO 585
<211> LENGTH: 9
<212> TYPE: PRT
<213> ORGANISM: Homo sapiens

<400> SEQUENCE: 585

Trp Ala Asp Leu Ser Gly Ile Thr Lys
1               5

<210> SEQ ID NO 586
<211> LENGTH: 7
<212> TYPE: PRT
<213> ORGANISM: Homo sapiens

<400> SEQUENCE: 586

Phe Ala Phe Asn Leu Tyr Arg
1               5

<210> SEQ ID NO 587
<211> LENGTH: 34
<212> TYPE: PRT
<213> ORGANISM: Homo sapiens

<400> SEQUENCE: 587

Phe Ala Thr Thr Phe Tyr Gln His Leu Ala Asp Ser Lys Asn Asp Asn
1               5                   10                  15

Asp Asn Ile Phe Leu Ser Pro Leu Ser Ile Ser Thr Ala Phe Ala Met
            20                  25                  30

Thr Lys

<210> SEQ ID NO 588
<211> LENGTH: 34
<212> TYPE: PRT
<213> ORGANISM: Homo sapiens

<400> SEQUENCE: 588

Phe Ala Thr Thr Phe Tyr Gln His Leu Ala Asp Ser Lys Asn Asp Asn
1               5                   10                  15

Asp Asn Ile Phe Leu Ser Pro Leu Ser Ile Ser Thr Ala Phe Ala Met
            20                  25                  30

Thr Lys

<210> SEQ ID NO 589
<211> LENGTH: 6
<212> TYPE: PRT
<213> ORGANISM: Homo sapiens

<400> SEQUENCE: 589

Leu Val Ser Ala Asn Arg
1               5

<210> SEQ ID NO 590
<211> LENGTH: 6
<212> TYPE: PRT
<213> ORGANISM: Homo sapiens

<400> SEQUENCE: 590

Leu Val Ser Ala Asn Arg
1               5

<210> SEQ ID NO 591
<211> LENGTH: 7
<212> TYPE: PRT
<213> ORGANISM: Homo sapiens

<400> SEQUENCE: 591

Arg Val Trp Glu Leu Ser Lys
1               5

<210> SEQ ID NO 592
<211> LENGTH: 7
<212> TYPE: PRT
<213> ORGANISM: Homo sapiens

<400> SEQUENCE: 592

Arg Val Trp Glu Leu Ser Lys
1               5

<210> SEQ ID NO 593
<211> LENGTH: 28
<212> TYPE: PRT
<213> ORGANISM: Homo sapiens

<400> SEQUENCE: 593

Val Ala Glu Gly Thr Gln Val Leu Glu Leu Pro Phe Lys Gly Asp Asp
1               5                   10                  15

Ile Thr Met Val Leu Ile Leu Pro Lys Pro Glu Lys
            20                  25

<210> SEQ ID NO 594
<211> LENGTH: 7
<212> TYPE: PRT
<213> ORGANISM: Homo sapiens

<400> SEQUENCE: 594

Phe Ala Phe Asn Leu Tyr Arg
1               5

```
<210> SEQ ID NO 595
<211> LENGTH: 9
<212> TYPE: PRT
<213> ORGANISM: Homo sapiens

<400> SEQUENCE: 595

Ser Val Asn Asp Leu Tyr Ile Gln Lys
1               5

<210> SEQ ID NO 596
<211> LENGTH: 12
<212> TYPE: PRT
<213> ORGANISM: Homo sapiens

<400> SEQUENCE: 596

Leu Gln Ser Leu Phe Asp Ser Pro Asp Phe Ser Lys
1               5                   10

<210> SEQ ID NO 597
<211> LENGTH: 10
<212> TYPE: PRT
<213> ORGANISM: Homo sapiens

<400> SEQUENCE: 597

Thr Val Gln Ala Val Leu Thr Val Pro Lys
1               5                   10

<210> SEQ ID NO 598
<211> LENGTH: 11
<212> TYPE: PRT
<213> ORGANISM: Homo sapiens

<400> SEQUENCE: 598

Thr Val Arg Val Pro Met Met Ser Asp Pro Lys
1               5                   10

<210> SEQ ID NO 599
<211> LENGTH: 7
<212> TYPE: PRT
<213> ORGANISM: Homo sapiens

<400> SEQUENCE: 599

Asp Phe Leu Gln Ser Leu Lys
1               5

<210> SEQ ID NO 600
<211> LENGTH: 10
<212> TYPE: PRT
<213> ORGANISM: Homo sapiens

<400> SEQUENCE: 600

Gly Asp Lys Leu Phe Gly Pro Asp Leu Lys
1               5                   10

<210> SEQ ID NO 601
<211> LENGTH: 27
<212> TYPE: PRT
<213> ORGANISM: Homo sapiens

<400> SEQUENCE: 601

Ile Gln Glu Phe Leu Ser Gly Leu Pro Glu Asp Thr Val Leu Leu Leu
1               5                   10                  15

Leu Asn Ala Ile His Phe Gln Gly Phe Trp Arg
```

20                  25

<210> SEQ ID NO 602
<211> LENGTH: 19
<212> TYPE: PRT
<213> ORGANISM: Homo sapiens

<400> SEQUENCE: 602

Met Glu Pro Phe His Phe Lys Asn Ser Val Ile Lys Val Pro Met Met
1               5                   10                  15

Asn Ser Lys

<210> SEQ ID NO 603
<211> LENGTH: 11
<212> TYPE: PRT
<213> ORGANISM: Homo sapiens

<400> SEQUENCE: 603

Pro Val Ala His Phe Ile Asp Gln Thr Leu Lys
1               5                   10

<210> SEQ ID NO 604
<211> LENGTH: 8
<212> TYPE: PRT
<213> ORGANISM: Homo sapiens

<400> SEQUENCE: 604

Val Ala Thr Thr Val Ile Ser Lys
1               5

<210> SEQ ID NO 605
<211> LENGTH: 14
<212> TYPE: PRT
<213> ORGANISM: Homo sapiens

<400> SEQUENCE: 605

Glu Ser Asn Thr Val Phe Ser Phe Leu Gly Leu Lys Pro Arg
1               5                   10

<210> SEQ ID NO 606
<211> LENGTH: 10
<212> TYPE: PRT
<213> ORGANISM: Homo sapiens

<400> SEQUENCE: 606

Val Tyr Ser Thr Ser Val Thr Gly Ser Arg
1               5                   10

<210> SEQ ID NO 607
<211> LENGTH: 14
<212> TYPE: PRT
<213> ORGANISM: Homo sapiens

<400> SEQUENCE: 607

Ile Ala Leu Gly Gly Leu Leu Phe Pro Ala Ser Asn Leu Arg
1               5                   10

<210> SEQ ID NO 608
<211> LENGTH: 8
<212> TYPE: PRT
<213> ORGANISM: Homo sapiens

<400> SEQUENCE: 608

Thr Ser Ser Ser Phe Glu Val Arg

```
1               5

<210> SEQ ID NO 609
<211> LENGTH: 24
<212> TYPE: PRT
<213> ORGANISM: Homo sapiens

<400> SEQUENCE: 609

Val Val Leu Ser Ser Gly Ser Gly Pro Gly Leu Asp Leu Pro Leu Val
1               5                   10                  15

Leu Gly Leu Pro Leu Gln Leu Lys
            20

<210> SEQ ID NO 610
<211> LENGTH: 6
<212> TYPE: PRT
<213> ORGANISM: Homo sapiens

<400> SEQUENCE: 610

Ala Ser Ile Ile Thr Lys
1               5

<210> SEQ ID NO 611
<211> LENGTH: 6
<212> TYPE: PRT
<213> ORGANISM: Homo sapiens

<400> SEQUENCE: 611

Leu Leu Asn Leu Gly Arg
1               5

<210> SEQ ID NO 612
<211> LENGTH: 9
<212> TYPE: PRT
<213> ORGANISM: Homo sapiens

<400> SEQUENCE: 612

Met Ser Phe Leu Gly Ile Leu Cys Lys
1               5

<210> SEQ ID NO 613
<211> LENGTH: 12
<212> TYPE: PRT
<213> ORGANISM: Homo sapiens

<400> SEQUENCE: 613

Arg Ser Arg Asn Thr Ala Val Glu Gln Arg Leu Arg
1               5                   10

<210> SEQ ID NO 614
<211> LENGTH: 17
<212> TYPE: PRT
<213> ORGANISM: Homo sapiens

<400> SEQUENCE: 614

Asp Val Gly Arg Pro Gln Pro Gly Arg Glu Asn Phe Gln Asn Trp Leu
1               5                   10                  15

Lys

<210> SEQ ID NO 615
<211> LENGTH: 11
<212> TYPE: PRT
<213> ORGANISM: Homo sapiens
```

```
<400> SEQUENCE: 615

Val Ser Leu Arg Arg Ala Leu Leu Glu Gln Lys
1               5                   10

<210> SEQ ID NO 616
<211> LENGTH: 13
<212> TYPE: PRT
<213> ORGANISM: Homo sapiens

<400> SEQUENCE: 616

Lys Leu Met Met Ile Leu Ala Met Asn Glu Lys Asp Lys
1               5                   10

<210> SEQ ID NO 617
<211> LENGTH: 11
<212> TYPE: PRT
<213> ORGANISM: Homo sapiens

<400> SEQUENCE: 617

His Gln Thr Val Pro Gln Asn Thr Gly Gly Lys
1               5                   10

<210> SEQ ID NO 618
<211> LENGTH: 20
<212> TYPE: PRT
<213> ORGANISM: Homo sapiens

<400> SEQUENCE: 618

Ser Asp Asn Cys Glu Asp Thr Pro Glu Ala Gly Tyr Phe Ala Val Ala
1               5                   10                  15

Val Val Lys Lys
            20

<210> SEQ ID NO 619
<211> LENGTH: 8
<212> TYPE: PRT
<213> ORGANISM: Homo sapiens

<400> SEQUENCE: 619

Tyr Leu Gly Glu Glu Tyr Val Lys
1               5

<210> SEQ ID NO 620
<211> LENGTH: 7
<212> TYPE: PRT
<213> ORGANISM: Homo sapiens

<400> SEQUENCE: 620

Asp Leu Ala Ser Ile Ala Arg
1               5

<210> SEQ ID NO 621
<211> LENGTH: 12
<212> TYPE: PRT
<213> ORGANISM: Homo sapiens

<400> SEQUENCE: 621

Phe Val Phe Gly Thr Thr Pro Glu Asp Ile Leu Arg
1               5                   10

<210> SEQ ID NO 622
<211> LENGTH: 9
<212> TYPE: PRT
<213> ORGANISM: Homo sapiens
```

<400> SEQUENCE: 622

Gly Thr Leu Leu Ala Leu Glu Arg Lys
1               5

<210> SEQ ID NO 623
<211> LENGTH: 7
<212> TYPE: PRT
<213> ORGANISM: Homo sapiens

<400> SEQUENCE: 623

His Leu Ala Cys Leu Pro Arg
1               5

<210> SEQ ID NO 624
<211> LENGTH: 14
<212> TYPE: PRT
<213> ORGANISM: Homo sapiens

<400> SEQUENCE: 624

Met Phe Gly Ile Asp Arg Asp Ala Ile Ala Gln Ala Val Arg
1               5                   10

<210> SEQ ID NO 625
<211> LENGTH: 12
<212> TYPE: PRT
<213> ORGANISM: Homo sapiens

<400> SEQUENCE: 625

Ala Leu Ser Thr Asp Pro Ala Ala Pro Asn Leu Lys
1               5                   10

<210> SEQ ID NO 626
<211> LENGTH: 12
<212> TYPE: PRT
<213> ORGANISM: Homo sapiens

<400> SEQUENCE: 626

Ala Val Ala Ser Ala Ala Ala Ala Leu Val Leu Lys
1               5                   10

<210> SEQ ID NO 627
<211> LENGTH: 22
<212> TYPE: PRT
<213> ORGANISM: Homo sapiens

<400> SEQUENCE: 627

Leu Ala Ser Glu Ala Lys Pro Ala Val Ala Ala Glu Asn Glu Glu
1               5                   10                  15

Ile Gly Ser His Ile Lys
            20

<210> SEQ ID NO 628
<211> LENGTH: 12
<212> TYPE: PRT
<213> ORGANISM: Homo sapiens

<400> SEQUENCE: 628

Val Leu Val Gln Asn Ala Ala Gly Ser Gln Glu Lys
1               5                   10

<210> SEQ ID NO 629
<211> LENGTH: 11
<212> TYPE: PRT

```
<213> ORGANISM: Homo sapiens

<400> SEQUENCE: 629

Val Met Val Thr Asn Val Thr Ser Leu Leu Lys
1               5                   10

<210> SEQ ID NO 630
<211> LENGTH: 15
<212> TYPE: PRT
<213> ORGANISM: Homo sapiens

<400> SEQUENCE: 630

Lys Gln Ser Glu Pro Leu Glu Ile Thr Leu Leu Ala Pro Glu Arg
1               5                   10                  15

<210> SEQ ID NO 631
<211> LENGTH: 14
<212> TYPE: PRT
<213> ORGANISM: Homo sapiens

<400> SEQUENCE: 631

Ile Gln Leu Val Glu Glu Leu Asp Arg Ala Gln Glu Arg
1               5                   10

<210> SEQ ID NO 632
<211> LENGTH: 13
<212> TYPE: PRT
<213> ORGANISM: Homo sapiens

<400> SEQUENCE: 632

Ala Ala Asp Asp Thr Trp Glu Pro Phe Ala Ser Gly Lys
1               5                   10

<210> SEQ ID NO 633
<211> LENGTH: 12
<212> TYPE: PRT
<213> ORGANISM: Homo sapiens

<400> SEQUENCE: 633

Ala Asp Asp Thr Trp Glu Pro Phe Ala Ser Gly Lys
1               5                   10

<210> SEQ ID NO 634
<211> LENGTH: 12
<212> TYPE: PRT
<213> ORGANISM: Homo sapiens

<400> SEQUENCE: 634

Lys Pro Leu Leu Glu Ser Gly Thr Leu Gly Thr Lys
1               5                   10

<210> SEQ ID NO 635
<211> LENGTH: 22
<212> TYPE: PRT
<213> ORGANISM: Homo sapiens

<400> SEQUENCE: 635

Thr Asp Gln Val Ile Gln Ser Leu Ile Ala Leu Val Asn Asp Pro Gln
1               5                   10                  15

Pro Glu His Pro Leu Arg
            20

<210> SEQ ID NO 636
<211> LENGTH: 10
```

```
<212> TYPE: PRT
<213> ORGANISM: Homo sapiens

<400> SEQUENCE: 636

Tyr Leu Gln Gly Ser Ser Val Gln Leu Arg
1               5                   10

<210> SEQ ID NO 637
<211> LENGTH: 14
<212> TYPE: PRT
<213> ORGANISM: Homo sapiens

<400> SEQUENCE: 637

Ala Gln Gln Val Ser Gln Gly Leu Asp Val Leu Thr Ala Lys
1               5                   10

<210> SEQ ID NO 638
<211> LENGTH: 10
<212> TYPE: PRT
<213> ORGANISM: Homo sapiens

<400> SEQUENCE: 638

Met Ser Ala Glu Ile Asn Glu Ile Ile Arg
1               5                   10

<210> SEQ ID NO 639
<211> LENGTH: 7
<212> TYPE: PRT
<213> ORGANISM: Homo sapiens

<400> SEQUENCE: 639

Ala Phe His Tyr Asp Met Lys
1               5

<210> SEQ ID NO 640
<211> LENGTH: 10
<212> TYPE: PRT
<213> ORGANISM: Homo sapiens

<400> SEQUENCE: 640

Gly Gln Tyr Cys Tyr Glu Leu Asp Glu Lys
1               5                   10

<210> SEQ ID NO 641
<211> LENGTH: 18
<212> TYPE: PRT
<213> ORGANISM: Homo sapiens

<400> SEQUENCE: 641

Leu Ile Arg Asp Val Trp Gly Ile Glu Gly Pro Ile Asp Ala Ala Phe
1               5                   10                  15

Thr Arg

<210> SEQ ID NO 642
<211> LENGTH: 11
<212> TYPE: PRT
<213> ORGANISM: Homo sapiens

<400> SEQUENCE: 642

His Ile Val Thr Phe Asp Gly Gln Asn Phe Lys
1               5                   10

<210> SEQ ID NO 643
<211> LENGTH: 15
```

```
<212> TYPE: PRT
<213> ORGANISM: Homo sapiens

<400> SEQUENCE: 643

Val Ile Val Ile Pro Val Gly Ile Gly Pro His Ala Asn Leu Lys
1               5                   10                  15

<210> SEQ ID NO 644
<211> LENGTH: 8
<212> TYPE: PRT
<213> ORGANISM: Homo sapiens

<400> SEQUENCE: 644

Tyr Ile Ile Leu Leu Leu Gly Lys
1               5

<210> SEQ ID NO 645
<211> LENGTH: 9
<212> TYPE: PRT
<213> ORGANISM: Homo sapiens

<400> SEQUENCE: 645

Tyr Asp Asp Met Ala Ala Ala Met Lys
1               5

<210> SEQ ID NO 646
<211> LENGTH: 9
<212> TYPE: PRT
<213> ORGANISM: Homo sapiens

<400> SEQUENCE: 646

Tyr Asp Asp Met Ala Ala Ala Met Lys
1               5
```

BIOMARKERS FOR LYMPHOMA

CROSS-REFERENCE TO RELATED APPLICATIONS

This application claims priority to U.S. Provisional APPLICATION Ser. No. 61/565,036, filed Nov. 30, 2011, titled "BIOMARKERS FOR HODGKIN'S LYMPHOMA", hereby incorporated by reference in its entirety.

STATEMENT REGARDING FEDERALLY SPONSORED RESEARCH OR DEVELOPMENT

The invention was made with Government support under Contract DE-AC05-76RLO1830, awarded by the U.S. Department of Energy. The Government has certain rights in the invention.

TECHNICAL FIELD

This invention relates to biomarkers for lymphoma. More specifically, this invention relates to plasma biomarkers for detecting Hodgkin's lymphoma or non-Hodgkin's lymphoma.

BACKGROUND OF THE INVENTION

In the presence of human immunodeficiency virus (HIV) infection, non-Hodgkin's lymphoma (NHL) and Kaposi sarcoma (KS) were the first malignancies used to define acquired immune deficiency syndrome (AIDS). People with HIV infection are also at increased risk of a number of other cancers. As people with HIV infection live longer due to highly active antiretroviral therapy (HAART), the incidence of these non-AIDS-defining cancers has increased among HIV-infected individuals. One of the most common of these malignancies is Hodgkin's lymphoma (HL), and it has been estimated that people with HIV/AIDS have a 5.6- to 14.7-fold increased risk of developing HL compared to the general population.

HL is a solid tumor that is comprised of no more than 2% of the cancerous B lymphocytes. Instead, these lymphocytes secrete a wide range of cytokines that attract numerous normal leukocytes that then comprise the large majority of the tumor. Thus, HL is largely seen as an uncontrolled inflammatory disease. In people with immunosuppression, HL is believed to result from the Epstein-Barr virus (EBV). EBV is present in nearly all adults, but typically only causes HL when the immune system is suppressed, such as with HIV infection.

The increase in non-AIDS-defining cancers has created a greater need for the early detection of these malignancies in this susceptible population. It seems likely that HIV-infected individuals would benefit from a routine, non-invasive screen for HL, but no such screen exists. Rather, HL patients are identified after they become symptomatic. Chemotherapy and radiation therapy have been shown to be very effective at causing HL remission, but morbidity and mortality associated with these treatments is substantial. Early-stage HL is generally treated less intensively, suggesting that early detection of HL would result in less treatment-related toxicity. Cancer treatment strategies for HIV-infected individuals with HL are the same as for non-AIDS subject, but HIV-infected patients require additional vigorous supportive care (HAART, antifungals, neutrophil-simulating growth factors).

What is needed is a blood-based test to detect lymphoma earlier, when the tumor burden is much smaller, which would allow for less severe therapy and reduce long-term mortality and morbidity associated with current treatments.

SUMMARY OF THE INVENTION

In one embodiment of the present invention, a biomarker for detecting lymphoma in a person is disclosed. The biomarkers include at least one protein listed in Table S3.

The lymphoma may be Hodgkin's lymphoma or non-Hodgkin's lymphoma. The at least one protein is found in plasma, and the person is a high-risk subject.

In another embodiment of the present invention, a method of detecting lymphoma in a person is disclosed. The method includes obtaining a plasma sample from the person. The method further includes measuring the level of at least one protein listed in Table S3 in the plasma sample. The method also includes comparing the level of the at least one protein in the plasma sample with the level in a normal or healthy subject; and diagnosing the lymphoma based upon the level of the at least one protein in the plasma sample in comparison to the normal level. In one embodiment, the obtaining a plasma sample from the person further comprises providing a reagent that reacts with proteins in the plasma sample to detect the presence of lymphoma. The reagent may be an antibody.

In another embodiment of the present invention, a test kit for diagnosing lymphoma in a person is disclosed. The test kit includes an antibody-based assay that measures a plurality of plasma biomarkers selected from the group consisting of the biomarkers of Table S3; and instructions for conducting the antibody-based assay.

In another embodiment of the present invention, a diagnostic system for detecting the presence of lymphoma in a person is disclosed. The system includes a plurality of protein assays measuring a plurality of plasma biomarkers. The plasma biomarkers are selected from the biomarkers of Table S3. Concentration levels or peak intensity values of at least one of the plasma biomarkers is modified by the presence of the lymphoma in the person. The system also includes a detector for detecting the plasma biomarkers.

In one embodiment, the detector is a mass spectrometer. In another embodiment, the detector includes at least one labeled antibody specific for a biomarker of Table S3.

DETAILED DESCRIPTION OF THE PREFERRED EMBODIMENTS

The present invention is directed to methods, diagnostic systems, kits, and biomarkers for detecting lymphoma in a patient. These biomarkers may form the basis for a blood-based test for early detection of lymphoma and may be used clinically.

To identify candidate biomarkers for Hodgkin's Lymphoma (HL) detection, plasma samples from HIV-infected patients were analyzed, with or without HL, using accurate mass tag and time (AMT) tag proteomics, and thereby identified a set of 60 proteins. As a group, these proteins are associated with both cancer and inflammation and therefore are promising candidate biomarkers for early detection of HL.

Materials and Methods

Ethics Statement.

The study protocol was approved by the George Washington University Medical Center Institutional Review Board. Written informed consent was obtained from all study participants. Additional approval from the PNNL Institutional Review Board, which included a review of the George Washington University Medical Center IRB approval, was obtained before samples were transferred to PNNL.

Human Subjects and Sample Processing.

Frozen, human plasma samples were provided by the AIDS and Cancer Specimen Resource (San Francisco, Calif.). The control subjects (HIV-infected without HL) were chosen to approximately match the cases (HIV-infected with HL) based on gender and age (Table 1). In most cases, plasma samples were collected from HIV-infected subjects with HL that had not received HL chemotherapy within at least 30 days (n=12). Information on chemotherapy was unknown for some cases (n=9) and one sample was known to have been collected within 30 days of chemotherapy. For all processing and analytical steps, samples were blocked based on HL status and randomized. The 12 most abundant plasma proteins were depleted using the Proteome Purify™ 12 immunodepletion resin (R&D Systems), according to the manufacturer's protocol. The remaining plasma proteins were precipitated using ice-cold trichloroacetic acid at a final concentration of 10%, followed by overnight incubation at 4° C. and centrifugation at 14,000×g for 5 minutes. The pellet was washed with cold acetone and dried at room temperature for 5 minutes prior to suspension in 25 µL of 100 mM ammonium bicarbonate, 8 M urea, 2 M thiourea and 5 mM dithiothreitol, and heating to 60° C. for 30 min. The samples were then diluted 4-fold with 100 mM ammonium bicarbonate and $CaCl_2$ was added to 1 mM. Methylated, sequencing-grade trypsin (Promega, Madison, Wis.) was added at a substrate-to-enzyme ratio of 50:1 (mass:mass) and incubated at 37° C. for 15 h. Peptides were then purified by binding to a 1 mL SPE $C_{18}$ column (Supelco, Bellefonte, Pa.) and eluting with 1 mL of methanol. After concentration in a SpeedVac, the samples were dissolved in 25 mM ammonium bicarbonate and frozen at −20° C. until analysis.

TABLE 1

Subject characteristics.

|  | HIV+ | HIV+/HL+ |
|---|---|---|
| Number | 14 | 22 |
| Gender (M/F) | 10/4 | 20/2 |
| Age (min-max) | 53.9 ± 5.9[a] (42-63) | 49.2 ± 8.8 (34-66) |
| CD4 count[b] | 404 ± 380 | 203 ± 224 |
| CD4 count < 200[c] | 4 (29%) | 12 (55%) |
| HAART[d] (yes, no, unknown) | 12, 1, 1 | 11, 4, 7 |
| Lymph node involvement | NA[e] | 6 |

[a]Mean ± standard deviation.
[b]Units are CD4-positive cell counts per µL blood.
[c]CD4 counts of less than 200/µL has been used to define the presence of AIDS in HIV positive subjects.
[d]Indicates current usage of HAART antiretroviral therapy at the time of the blood draw. "Unknown" indicates that HAART usage at the time of the blood draw is unknown. Prior usage is unknown for all subjects.
[e]NA, not applicable.

Liquid Chromatography-Mass Spectrometry.

Peptide samples were analyzed using a custom-built, automated, high-pressure nanocapillary liquid chromatography (HPLC) system coupled on-line to a LTQ-Orbitrap mass spectrometer (Thermo Fisher Scientific). The reversed-phase capillary column was prepared by slurry packing 3-µm Jupiter C18 bonded particles (Phenomenex, Torrence, Calif.) into a 65-cm-long, 75-µm-inner diameter fused silica capillary (Polymicron Technologies, Phoenix, Ariz.). The mobile phase consisted of 0.2% acetic acid and 0.05% trifluoroacetate in water (A) and 0.1% trifluoroacetate in 90% acetonitrile, 10% water (B). After loading 5 µL (2.5 µg total) of peptides onto the column, the mobile phase was held at 100% A for 50 min. Exponential gradient elution was performed by increasing the mobile phase composition from 0 to 55% B over 115 min. The HPLC column was coupled to the mass spectrometer by an in-house manufactured electrospray ionization interface. The heated capillary inlet temperature and electrospray voltage were 200° C. and 2.2 kV, respectively. Data were acquired for 100 min, beginning 65 min after sample injection (15 min into start of buffer B gradient). Orbitrap spectra (AGC $5 \times 10^5$) were collected from 400-2000 m/z at a resolution of 100,000.

The mass spectra were analyzed using the AMT tag approach. The peak lists for each analysis were matched against a mass tag database containing 30,573 tryptic peptides that were previously identified from LC-MS/MS analyses of human plasma. An estimate of the false-positive rate for peptide identifications in our analysis, which was <6%, was obtained by searching the sequence-reversed database.

Statistics.

There were 76 mass spectrometry runs included in the proteomics data, including at least two analyses for each of the 36 samples. A total of 6460 unique peptides were initially identified. The data-analysis process first removed peptides for which there were insufficient identifications to perform a statistical analysis, which reduced the peptide number to 3814. Next, the peptide abundance measurements were normalized via regression based on all the peptide signals for that mass spectrometer run and then averaged across replicate runs for each sample. The averaged signal intensities were normalized for each sample based on the median absolute deviation of the signal intensity for all peptides identified in each sample. Finally, the data were subjected to two statistical tests to determine peptides having differential abundance due to either signal intensities or presence-absence. A non-parametric Mann-Whitney test was performed using MatLab 2009 to compare signal intensities. Differences in detection incidence was determined using a modified Chi-square test, called a G-test. Using either test, 647 peptides were identified with a p-value of 0.05 or less.

Normalized peptide abundance values were used for protein inference; the peptide abundance measurements were weighted and combined to calculate the relative protein abundances in the two groups using RRollup within DAnTEm. Only proteins represented by two or more unique peptides were analyzed. Peptide redundancy was reduced with Protein Prophet and by manually selecting characterized proteins over predicted or hypothetical proteins.

Ingenuity Pathway Analysis.

Differentially regulated proteins were analyzed for common biological functions using Ingenuity Pathway Analysis (IPA; Ingenuity Systems, Mountain View, Calif.) software. To infer significant biological functions, all proteins that were significantly different between groups and their corresponding ratiometric values (HL+/HL−; minimum of 1.5-fold change) were analyzed by IPA. The significance values for biological function were determined using the right-tailed Fisher's Exact Test.

Results and Discussion

To identify potential circulating biomarkers for HL in a susceptible population, we used the AMT tag LC-MS approach to compare the plasma proteomes from 36 HIV-infected patients with or without HL. The HIV-infected patients without HL served as the control group to identify protein changes associated with HL. The relatively highthroughput characteristics of this approach enabled duplicate analyses of each of the 36 plasma samples, thereby improving data quality. The subject characteristics are described in Table 1. The proteomics analysis identified 3814 peptides across all of the samples, which corresponded to 629 proteins. Of these 3814 peptides, 647 were significantly different between the two disease states, which corresponded to 152 proteins (Tables S1 and S2). Sixty of these proteins met our criteria of being both significantly different between the two groups and having at least 1.5-fold difference in the normalized signal (Table S3). This protein list included well-known acute-phase inflammatory proteins, including C-reactive protein and serum amyloid proteins. To better identify common biological functions within these 60 proteins, Ingenuity Pathway Analysis (IPA) was utilized. In general, proteins that were associated with immune responses and cancer were highly represented in the list of significantly altered biological functions. Many of the proteins we identified are known to be secreted by white blood cells, such as those that infiltrate HL tumors, or by the liver, an important component of the reticuloendothelial system (Table S3). Similarly, the use of IPA to identify common biological functions across the 60 proteins identified "inflammatory response" and "cancer" (Table 2), suggesting that these proteins have a biological relationship with HL. Since only 1% to 2% of the mass of an HL tumor is composed of the cancerous lymphocytes, it may be that the proteins we identified did not originate from these relatively rare cells. Rather, these proteins may be the product of a systemic inflammatory response associated with HL or due to noncancerous leukocytes that form ~99% of the tumor mass.

TABLE 2

Top BioFunctions and associated proteins, as defined by Ingenuity Pathway Analysis.

| Name | p-value range[a] | Associated proteins[b] |
|---|---|---|
| Inflammatory Response | $3.0 \times 10^{-10}$- $1.1 \times 10^{-02}$ | AHSG, AMBP, APOE, ARHGDIB, B2M, C4A/C4B, C8A, CD14, CFD, CRP, GSN, LUM, MBL2, MCAM, MASP1, MSN, PPBP, PNP, PTGDS, PVR, SAA1, SEMA7A, TIMP1 |
| Cancer | $9.2 \times 10^{-09}$- $1.1 \times 10^{-02}$ | AHSG, AMBP, APOC1, APOE, ARHGDIB, AZGP1, B2M, C4A/C4B, CD14, CFD, COL6A3, CRP, CST3, EFEMP1, GSN, |

TABLE 2-continued

Top BioFunctions and associated proteins, as defined by Ingenuity Pathway Analysis.

| Name | p-value range[a] | Associated proteins[b] |
|---|---|---|
| | | IGFBP2, KRT10, MCAM, MASP1, PNP, PTGDS, SAA1, SELENBP1, TIMP1, YWHAG |

[a]The p-values reflect the range of all the subcategories that the Ingenuity Pathway Analysis included under the header of Inflammatory Response or Cancer. That is, these two BioFunctions have 39 or 35 subcategories, respectively, and each of these subcategories show significant differences, within the range of p-values shown, between the HIV+ (without HL) and HIV+/HL+ groups.
[b]Abbreviations are defined in Table S3.

At least three of the proteins we identified have been previously reported to be increased in HL subjects compared to healthy controls, including C-reactive protein, beta-2-microglobulin and lactate dehydrogenase. These prior studies examined HL in the general population, and did not focus on HIV-positive subjects. In addition, these studies measured these proteins by immunoassay, providing analytical verification as well. In the current study, the presence of HIV in the study population could be a confounding factor. For example, the HL subjects appeared to have slightly more advanced cases of HIV, on the average, as suggested by a trend (p=0.07, t-test) towards lower CD4-positive cell counts (Table 1), a result which is consistent with slightly more advanced immunosuppression. Even so, since three of the proteins we identified are increased in HL subjects without HIV, it seems clear that the results for these proteins, at least, are not confounded by differential states of HIV infection. Overall, the present study independently validates three plasma biomarkers for HL and identifies an additional 57 novel plasma proteins that appear to be promising candidate biomarkers based on their relationships with cancer and inflammation. These candidate biomarkers remain to be validated in regards to their association with HL.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

TABLE S1

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| — | P25 | IPI:IPI00386965.1 | FVTKAEEK | 0.22 | 0.21 | 1.04 |
| — | CDNA FLJ33508 fis, clone BRAMY2005094 | IPI:IPI00166374.1 | YNDYLITIK | | 0.23 | |
| A1BG | Alpha-1B-glycoprotein | IPI:IPI00022895.7 | SLPAPWLSMAPVSWITPGLK | 0.45 | 0.59 | 0.77 |
| A2M | Alpha-2-macroglobulin | IPI:IPI00478003.1 | AFQPFFVELTMPYSVIR | 7.72 | 0.32 | 24.32 |
| A2M | Alpha-2-macroglobulin | IPI:IPI00478003.1 | ASVSVLGDILGSAMQN | 0.36 | 0.61 | 0.59 |
| A2M | Alpha-2-macroglobulin | IPI:IPI00478003.1 | ATVLNYLPK | 7.93 | 0.43 | 18.58 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| A2M | Alpha-2-macroglobulin | IPI:IPI00478003.1 | AVDQSVLLMKPDAELSASSVYNLLPEK | 4.59 | | |
| A2M | Alpha-2-macroglobulin | IPI:IPI00478003.1 | AYAFALAGNQDKR | 0.15 | | |
| A2M | Alpha-2-macroglobulin | IPI:IPI00478003.1 | DMYSFLEDMGLK | 6.62 | | |
| A2M | Alpha-2-macroglobulin | IPI:IPI00478003.1 | DTVIKPLLVEPEGLEK | 9.70 | | |
| A2M | Alpha-2-macroglobulin | IPI:IPI00478003.1 | GGVEDEVTLSAYITIALLEIPLTVTHPVVR | 3.16 | | |
| A2M | Alpha-2-macroglobulin | IPI:IPI00478003.1 | GHFSISIPVK | 6.81 | | |
| A2M | Alpha-2-macroglobulin | IPI:IPI00478003.1 | GPTQEFK | 2.20 | | |
| A2M | Alpha-2-macroglobulin | IPI:IPI00478003.1 | HYDGSYSTFGER | 5.25 | | |
| A2M | Alpha-2-macroglobulin | IPI:IPI00478003.1 | LLIYAVLPTGDVIGDSAK | 9.45 | 0.31 | 30.49 |
| A2M | Alpha-2-macroglobulin | IPI:IPI00478003.1 | LLLQQVSLPELPGEYSMK | 10.03 | 0.29 | 34.54 |
| A2M | Alpha-2-macroglobulin | IPI:IPI00478003.1 | LPPNVVEESAR | 6.87 | | |
| A2M | Alpha-2-macroglobulin | IPI:IPI00478003.1 | QGIPFFGQVR | 4.59 | | |
| A2M | Alpha-2-macroglobulin | IPI:IPI00478003.1 | QTVSWAVTPK | 8.37 | | |
| A2M | Alpha-2-macroglobulin | IPI:IPI00478003.1 | SDIAPVAR | 3.78 | 1.61 | 2.35 |
| A2M | Alpha-2-macroglobulin | IPI:IPI00478003.1 | SIYKPGQTVK | 5.37 | | |
| A2M | Alpha-2-macroglobulin | IPI:IPI00478003.1 | SVSGKPQYMVLVPSLLHTET | 12.16 | | |
| A2M | Alpha-2-macroglobulin | IPI:IPI00478003.1 | TGTHGLLVK | 8.95 | | |
| A2M | Alpha-2-macroglobulin | IPI:IPI00478003.1 | VIKPLLVEPEGLEK | 0.84 | 0.99 | 0.85 |
| A2M | Alpha-2-macroglobulin | IPI:IPI00478003.1 | VSVQLEASPAFLAVPVEK | 7.90 | | |
| ACTA1 | Actin, alpha skeletal muscle | IPI:IPI00021428.1 | AGFAGDDAPR | 13.47 | 20.00 | 0.67 |
| ACTA1 | Actin, alpha skeletal muscle | IPI:IPI00021428.1 | DLTDYLMK | 18.97 | 28.69 | 0.66 |
| ACTA1 | Actin, alpha skeletal muscle | IPI:IPI00021428.1 | DSYVGDEAQSKR | 0.79 | 0.60 | 1.32 |
| ACTA1 | Actin, alpha skeletal muscle | IPI:IPI00021428.1 | EITALAPSTMK | 26.67 | 40.43 | 0.66 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| ACTA1 | Actin, alpha skeletal muscle | IPI:IPI00021428.1 | HQGVMVGMGQK | 10.17 | 10.44 | 0.97 |
| ACTA1 | Actin, alpha skeletal muscle | IPI:IPI00021428.1 | SYELPDGQVITIGNER | 26.79 | 39.27 | 0.68 |
| ACTA1 | Actin, alpha skeletal muscle | IPI:IPI00021428.1 | YPIEHGIITNWDDMEKIWHHTFYNELR | 0.86 | | |
| ACTB | Actin, cytoplasmic 1 | IPI:IPI00021439.1 | AGFAGDDAPR | 13.47 | 20.00 | 0.67 |
| ACTB | Actin, cytoplasmic 1 | IPI:IPI00021439.1 | DLTDYLMK | 18.97 | 28.69 | 0.66 |
| ACTB | Actin, cytoplasmic 1 | IPI:IPI00021439.1 | DSYVGDEAQSKR | 0.79 | 0.60 | 1.32 |
| ACTB | Actin, cytoplasmic 1 | IPI:IPI00021439.1 | EITALAPSTMK | 26.67 | 40.43 | 0.66 |
| ACTB | Actin, cytoplasmic 1 | IPI:IPI00021439.1 | HQGVMVGMGQK | 10.17 | 10.44 | 0.97 |
| ACTB | Actin, cytoplasmic 1 | IPI:IPI00021439.1 | SYELPDGQVITIGNER | 26.79 | 39.27 | 0.68 |
| ACTB | Actin, cytoplasmic 1 | IPI:IPI00021439.1 | TTGIVMDSGDGVTHTVPIYEGYALPHAILR | 36.07 | 48.57 | 0.74 |
| ACTN1 | Alpha-actinin-1 | IPI:IPI00013508.5 | LAILGIHNEVSK | 1.17 | 0.70 | 1.68 |
| ACTN1 | Alpha-actinin-1 | IPI:IPI00013508.5 | VGWEQLLTTIAR | 1.50 | 1.32 | 1.13 |
| ADAMTSL2 | ADAMTS-like protein 2 | IPI:IPI00644346.2 | NFNIAGTVVK | 0.68 | 0.55 | 1.23 |
| AGT | Angiotensinogen | IPI:IPI00032220.3 | STLAFNTYVHFQGK | 1.61 | | |
| AGT | Angiotensinogen | IPI:IPI00032220.3 | VGEVLNSIFFELEADER | | 0.26 | |
| AHSG | Alpha-2-HS-glycoprotein | IPI:IPI00022431.1 | FSVVYAK | 80.04 | 123.13 | 0.65 |
| ALB | Serum albumin | IPI:IPI00745872.2 | AEFAEVSK | 3.86 | 0.16 | 23.74 |
| ALB | Serum albumin | IPI:IPI00745872.2 | AVMDDFAAFVEK | 26.36 | | |
| ALB | Serum albumin | IPI:IPI00745872.2 | DVFLGMFLYEYAR | 6.14 | | |
| ALB | Serum albumin | IPI:IPI00745872.2 | FKDLGEENFK | 19.32 | | |
| ALB | Serum albumin | IPI:IPI00745872.2 | FQNALLVR | 18.06 | 0.09 | 209.25 |
| ALB | Serum albumin | IPI:IPI00745872.2 | KQTALVELVK | 6.23 | | |
| ALB | Serum albumin | IPI:IPI00745872.2 | KYLYEIAR | 2.08 | 2.41 | 0.86 |
| ALB | Serum albumin | IPI:IPI00745872.2 | LVAASQAALGL | 6.02 | | |
| ALB | Serum albumin | IPI:IPI00745872.2 | LVNEVTEFAK | 25.15 | | |
| ALB | Serum albumin | IPI:IPI00745872.2 | LVTDLTK | 5.31 | | |
| ALB | Serum albumin | IPI:IPI00745872.2 | QNCELFEQLGEYK | | 1.14 | |
| ALB | Serum albumin | IPI:IPI00745872.2 | RHPYFYAPELLFFAK | 4.53 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| ALB | Serum albumin | IPI:IPI00745872.2 | TYETTLEK | 5.97 | | |
| ALB | Serum albumin | IPI:IPI00745872.2 | VFDEFKPLVEEPQNLIK | 19.11 | | |
| ALB | Serum albumin | IPI:IPI00745872.2 | VPQVSTPTLVEVSR | 1.26 | | |
| ALB | Serum albumin | IPI:IPI00745872.2 | YLYEIAR | 7.48 | | |
| ALDH3A1 | Aldehyde dehydrogenase, dimeric NADP-preferring | IPI:IPI00296183.7 | FMNSGQTCVAPDYILCDPSIQNQIVEKLKK | 0.46 | | |
| AMBP | AMBP protein | IPI:IPI00022426.1 | AFIQLWAFDAVK | 26.03 | 45.43 | 0.57 |
| AMBP | AMBP protein | IPI:IPI00022426.1 | TVAACNLPIVR | 2.78 | 7.69 | 0.36 |
| ANKRD6 | Isoform 2 of Ankyrin repeat domain-containing protein 6 | IPI:IPI00218274.1 | KRERLK | | 0.06 | |
| ANPEP | Aminopeptidase N | IPI:IPI00221224.6 | ALEQALEK | 0.21 | 0.53 | 0.40 |
| APOA1 | Apolipoprotein A-I | IPI:IPI00021841.1 | AKPALEDLR | 40.63 | 61.64 | 0.66 |
| APOA1 | Apolipoprotein A-I | IPI:IPI00021841.1 | FLSALEEYTK | 0.67 | 0.46 | 1.46 |
| APOA1 | Apolipoprotein A-I | IPI:IPI00021841.1 | LHELQEKLSPLGEEMRDR | 0.99 | 1.38 | 0.72 |
| APOA1 | Apolipoprotein A-I | IPI:IPI00021841.1 | QKVEPLR | 5.27 | 4.80 | 1.10 |
| APOA1 | Apolipoprotein A-I | IPI:IPI00021841.1 | QKVEPLRAELQEGAR | 4.64 | 5.86 | 0.79 |
| APOA1 | Apolipoprotein A-I | IPI:IPI00021841.1 | VEPLRAELQEGAR | 4.87 | 5.23 | 0.93 |
| APOA1 | Apolipoprotein A-I | IPI:IPI00021841.1 | VQPYLDDFQKK | 13.44 | 32.60 | 0.41 |
| APOA1 | Apolipoprotein A-I | IPI:IPI00021841.1 | VSFLSALEEYTK | 49.59 | 71.41 | 0.69 |
| APOA4 | Apolipoprotein A-IV | IPI:IPI00304273.2 | DSEKLKEEIGK | | 0.17 | |
| APOA4 | Apolipoprotein A-IV | IPI:IPI00304273.2 | ISASAEELRQR | 0.29 | 0.81 | 0.35 |
| APOA4 | Apolipoprotein A-IV | IPI:IPI00304273.2 | QLTPYAQR | 2.50 | 2.92 | 0.86 |
| APOA4 | Apolipoprotein A-IV | IPI:IPI00304273.2 | RRVEPYGENFNK | | 0.22 | |
| APOA4 | Apolipoprotein A-IV | IPI:IPI00304273.2 | VEPYGENFNK | 0.48 | 0.47 | 1.01 |
| APOB | Apolipoprotein B-100 | IPI:IPI00022229.1 | ALYWVNGQVPDGVSK | 0.79 | 0.47 | 1.69 |
| APOB | Apolipoprotein B-100 | IPI:IPI00022229.1 | DKIGVELTGR | 5.81 | | |
| APOB | Apolipoprotein B-100 | IPI:IPI00022229.1 | EEEAASGLLTSLKDNVPK | 0.38 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| APOB | Apolipoprotein B-100 | IPI:IPI00022229.1 | ENFAGEATLQR | 18.65 | 17.01 | 1.10 |
| APOB | Apolipoprotein B-100 | IPI:IPI00022229.1 | ESVKFSSK | 0.14 | | |
| APOB | Apolipoprotein B-100 | IPI:IPI00022229.1 | HIYAISSAALSASYK | 1.39 | 0.64 | 2.17 |
| APOB | Apolipoprotein B-100 | IPI:IPI00022229.1 | NIQEYLSILTDPDGKGKEK | 1.29 | 6.98 | 0.19 |
| APOB | Apolipoprotein B-100 | IPI:IPI00022229.1 | QIDDIDVR | 8.19 | 10.09 | 0.81 |
| APOB | Apolipoprotein B-100 | IPI:IPI00022229.1 | SKEVPEAR | 0.18 | 0.17 | 1.07 |
| APOB | Apolipoprotein B-100 | IPI:IPI00022229.1 | SKPTVSSSMEFK | | 0.16 | |
| APOB | Apolipoprotein B-100 | IPI:IPI00022229.1 | TEHGSEMLFFGNAIEGK | 0.13 | 0.46 | 0.27 |
| APOB | Apolipoprotein B-100 | IPI:IPI00022229.1 | TLQGIPQMIGEVIRK | 1.09 | 0.81 | 1.35 |
| APOB | Apolipoprotein B-100 | IPI:IPI00022229.1 | VLVDHFGYTKDDKHEQDMVNGIMLSVEK | 0.80 | 0.31 | 2.56 |
| APOB | Apolipoprotein B-100 | IPI:IPI00022229.1 | VRESDEETQIK | 0.07 | 0.19 | 0.36 |
| APOB | Apolipoprotein B-100 | IPI:IPI00022229.1 | YEVDQQIQVLMDK | | 0.16 | |
| APOB | Apolipoprotein B-100 | IPI:IPI00022229.1 | YKNFATSNK | 1.22 | 1.01 | 1.20 |
| APOB | Apolipoprotein B-100 | IPI:IPI00022229.1 | YLRTEHGSEMLFFGNAIEGK | | 0.92 | |
| APOC1 | Apolipoprotein C-I | IPI:IPI00021855.1 | EWFSETFQK | 3.00 | 0.10 | 30.94 |
| APOC1 | Apolipoprotein C-I | IPI:IPI00021855.1 | LKEFGNTLEDK | 7.68 | 0.30 | 25.40 |
| APOC1 | Apolipoprotein C-I | IPI:IPI00021855.1 | MREWFSETFQK | 3.08 | 0.38 | 8.18 |
| APOC1 | Apolipoprotein C-I | IPI:IPI00021855.1 | TPDVSSALDKLKEFGNTLEDK | 1.13 | | |
| APOC2 | Apolipoprotein C-II | IPI:IPI00021856.3 | TAAQNLYEK | 5.43 | 2.86 | 1.90 |
| APOC3 | Apolipoprotein C-III | IPI:IPI00021857.1 | SEAEDASLLSFMQGYMK | 1.02 | | |
| APOE | Apolipoprotein E | IPI:IPI00021842.1 | FWDYLR | 3.08 | 0.96 | 3.22 |
| APOE | Apolipoprotein E | IPI:IPI00021842.1 | GEVQAMLGQSTEELR | 8.71 | 3.56 | 2.45 |
| APOE | Apolipoprotein E | IPI:IPI00021842.1 | LEEQAQQIR | 0.55 | 0.12 | 4.78 |
| APOE | Apolipoprotein E | IPI:IPI00021842.1 | LKSWFEPLVEDMQR | 0.77 | 0.44 | 1.76 |
| APOE | Apolipoprotein E | IPI:IPI00021842.1 | MEEMGSR | 0.29 | 0.11 | 2.70 |
| APOE | Apolipoprotein E | IPI:IPI00021842.1 | QWAGLVEK | 2.11 | 0.77 | 2.74 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| APOE | Apolipoprotein E | IPI:IPI00021842.1 | RLAVYQAGAR | 0.21 | | |
| APOE | Apolipoprotein E | IPI:IPI00021842.1 | WVQTLSEQVQEELLSSQVTQELR | 6.49 | 2.16 | 3.01 |
| APOF | apolipoprotein F | IPI:IPI00299435.3 | SGVQQLIQYYQDQK | 1.79 | | |
| APOH | Beta-2-glycoprotein 1 | IPI:IPI00298828.3 | ATVVYQGER | 31.67 | 42.04 | 0.75 |
| APOH | Beta-2-glycoprotein 1 | IPI:IPI00298828.3 | EHSSLAFWK | 27.55 | 40.14 | 0.69 |
| APOH | Beta-2-glycoprotein 1 | IPI:IPI00298828.3 | TCPKPDDLPFSTVVPLK | 0.34 | 0.75 | 0.45 |
| APOL1 | 42 kDa protein | IPI:IPI0852826.2 | NWFLKEFPR | 1.00 | 0.38 | 2.59 |
| APOM | Apolipoprotein M | IPI:IPI00030739.1 | AFLLTPR | 2.31 | 1.34 | 1.72 |
| APOM | Apolipoprotein M | IPI:IPI00030739.1 | FLLYNR | 2.37 | 1.73 | 1.37 |
| APOM | Apolipoprotein M | IPI:IPI00030739.1 | KWIYHLTEGSTDLR | 0.24 | | |
| ARHGDIB | Rho GDP-dissociation inhibitor 2 | IPI:IPI00003817.3 | ETIVLKEGSEYR | | 4.62 | |
| ARHGDIB | Rho GDP-dissociation inhibitor 2 | IPI:IPI00003817.3 | TLLGDGPVVTDPK | 0.33 | | |
| ARNTL | Isoform MOP3 of Aryl hydrocarbon receptor nuclear translocator-like protein 1 | IPI:IPI00217736.1 | EMTGSGRR | | 0.21 | |
| ASL | Argininosuccinate lyase | IPI:IPI00220267.7 | ALLQAQQA | 0.39 | 0.61 | 0.64 |
| AZGP1 | alpha-2-glycoprotein 1, zinc | IPI:IPI00166729.4 | AGEVQEPELR | 11.94 | 16.22 | 0.74 |
| AZGP1 | alpha-2-glycoprotein 1, zinc | IPI:IPI00166729.4 | HVEDVPAFQALGSLNDLQFFR | 19.92 | 31.15 | 0.64 |
| AZGP1 | alpha-2-glycoprotein 1, zinc | IPI:IPI00166729.4 | IDVHWTR | 15.39 | 23.89 | 0.64 |
| AZGP1 | alpha-2-glycoprotein 1, zinc | IPI:IPI00166729.4 | YSLTYIYTGLSK | 22.15 | 34.77 | 0.64 |
| B2M | Beta-2-microglobulin | IPI:IPI00868938.1 | IEKVEHSDLSFSK | | 2.38 | |
| B2M | Beta-2-microglobulin | IPI:IPI00868938.1 | IQVYSR | 0.75 | 3.60 | 0.21 |
| BCHE | Cholinesterase | IPI:IPI00025864.5 | DNNSIITR | 7.68 | 9.51 | 0.81 |
| BCHE | Cholinesterase | IPI:IPI00025864.5 | WNNYMMDWK | | 0.35 | |
| BHMT | Betaine--homocysteine S-methyltransferase 1 | IPI:IPI00004101.4 | AGPWTPEAAVEHPEAVR | 1.72 | | |
| BLVRB | Flavin reductase | IPI:IPI00783862.2 | HDLGHFMLR | 0.28 | | |
| BRUNOL4 | LYST-interacting protein LIP9 (Fragment) | IPI:IPI00386504.1 | MAALNMIWAGSRTYDPNLR | 0.51 | | |
| BRWD1 | Isoform B of Bromodomain and WD repeat-containing protein 1 | IPI:IPI00250716.1 | ASAVAR | 19.37 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
| --- | --- | --- | --- | --- | --- | --- |
| BTD | biotinidase | IPI:IPI00218413.2 | QEALELMNQNLDIYEQQVMTAAQK | 0.33 | 0.56 | 0.59 |
| C1QA | Complement C1q subcomponent subunit A | IPI:IPI00022392.1 | SLGFCDTTNK | 1.32 | 1.28 | 1.03 |
| C1QB | complement component 1, q subcomponent, B chain | IPI:IPI00477992.1 | DQTIRFDHVITNMNNNYEPR | | 0.66 | |
| C1R | Complement C1r subcomponent | IPI:IPI00296165.5 | YTTEIIK | 4.66 | 6.69 | 0.70 |
| C1R; C17orf1 | Complement C1r subcomponent | IPI:IPI00296165.5 | EFMSQGNK | 0.59 | 0.85 | 0.69 |
| C1RL | Complement C1r-like protein | IPI:IPI00009793.3 | GSEAINAPGDNPAK | 0.42 | 0.43 | 0.98 |
| C1RL | Complement C1r-like protein | IPI:IPI00009793.3 | LGNFPWQAFTSIHGR | 0.13 | | |
| C1S | Complement C1s subcomponent | IPI:IPI00017696.1 | EVKVEKPTADAEAYVFTPNMICAGGEKG | 6.25 | 9.93 | 0.63 |
| C1S | Complement C1s subcomponent | IPI:IPI00017696.1 | IIGGSDADIK | 2.17 | | |
| C1S | Complement C1s subcomponent | IPI:IPI00017696.1 | TNFDNDIALVR | 5.26 | 6.98 | 0.75 |
| C1S | Complement C1s subcomponent | IPI:IPI00017696.1 | VKNYVDWIMK | 0.50 | 1.73 | 0.29 |
| C2 | Complement C2 (Fragment) | IPI:IPI00303963.1 | SSGQWQTPGATR | 0.45 | 0.63 | 0.71 |
| C2 | Complement C2 (Fragment) | IPI:IPI00303963.1 | TPWHVTIKPK | 0.31 | | |
| C3 | Complement C3 (Fragment) | IPI:IPI00783987.2 | APSTWLTAYVVK | 45.19 | 52.79 | 0.86 |
| C3 | Complement C3 (Fragment) | IPI:IPI00783987.2 | DQLTCNKFDLK | 0.28 | 0.49 | 0.58 |
| C3 | Complement C3 (Fragment) | IPI:IPI00783987.2 | DSCVGSLVVK | 5.38 | 7.71 | 0.70 |
| C3 | Complement C3 (Fragment) | IPI:IPI00783987.2 | EALKLEEK | 39.64 | 49.25 | 0.80 |
| C3 | Complement C3 (Fragment) | IPI:IPI00783987.2 | ETKENEGFTVTAEGK | 0.12 | 0.08 | 1.55 |
| C3 | Complement C3 (Fragment) | IPI:IPI00783987.2 | EYVLPSFEVIVEPTEKFYYIYNEK | | 7.25 | |
| C3 | Complement C3 (Fragment) | IPI:IPI00783987.2 | GQGTLSVVTMYHAK | 71.12 | 89.56 | 0.79 |
| C3 | Complement C3 (Fragment) | IPI:IPI00783987.2 | IEGDHGAR | 0.31 | 0.69 | 0.45 |
| C3 | Complement C3 (Fragment) | IPI:IPI00783987.2 | ILLQGTPVAQMTEDAVDAERLK | 6.56 | 31.38 | 0.21 |
| C3 | Complement C3 (Fragment) | IPI:IPI00783987.2 | PESWLWNVEDLKEPPK | 0.14 | | |
| C3 | Complement C3 (Fragment) | IPI:IPI00783987.2 | PPADLSDQVPDTESETR | 0.18 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| C3 | Complement C3 (Fragment) | IPI:IPI00783987.2 | PYVIVPLKTGLQEVEVK | 0.68 | 1.71 | 0.40 |
| C3 | Complement C3 (Fragment) | IPI:IPI00783987.2 | SGSDEVQVGQQR | 39.75 | 46.61 | 0.85 |
| C3 | Complement C3 (Fragment) | IPI:IPI00783987.2 | SINTHPSQKPLSITVR | 0.20 | | |
| C3 | Complement C3 (Fragment) | IPI:IPI00783987.2 | VLLDGVQNPR | 83.31 | 104.55 | 0.80 |
| C3 | Complement C3 (Fragment) | IPI:IPI00783987.2 | VVLVSLQSGYLFIQTDK | 4.92 | 5.73 | 0.86 |
| C4A | Complement component 4A | IPI:IPI00643525.1 | GQIVFMNREPK | 11.87 | 5.23 | 2.27 |
| C4A | Complement component 4A | IPI:IPI00643525.1 | GSGATFSHYYYMILSR | 0.52 | | |
| C4A | Complement component 4A | IPI:IPI00643525.1 | HLVPGAPFLLQALVR | 15.53 | 5.25 | 2.95 |
| C4A | Complement component 4A | IPI:IPI00643525.1 | LGQYASPTAKR | 0.17 | 0.26 | 0.64 |
| C4A | Complement component 4A | IPI:IPI00643525.1 | LNMGITDLQGLR | 72.56 | 46.19 | 1.57 |
| C4A | Complement component 4A | IPI:IPI00643525.1 | LVNGQSHISLSK | 0.48 | 0.55 | 0.87 |
| C4A | Complement component 4A | IPI:IPI00643525.1 | PNMIPDGDFNSYVR | 0.43 | | |
| C4A | Complement component 4A | IPI:IPI00643525.1 | SMQGGLVGNDETVALTAFVTIALHHGLAVFQDEGAEPLKQR | 0.40 | 0.13 | 3.05 |
| C4A | Complement component 4A | IPI:IPI00643525.1 | SPSVVHLGVPLSVGVQLQDVPR | 0.45 | 0.70 | 0.64 |
| C4A | Complement component 4A | IPI:IPI00643525.1 | TITVMVENSHGLR | | 0.29 | |
| C4B | C4B1 | IPI:IPI00418163.3 | GQIVFMNREPK | 11.87 | 5.23 | 2.27 |
| C4B | C4B1 | IPI:IPI00418163.3 | GSGATFSHYYYMILSR | 0.52 | | |
| C4B | C4B1 | IPI:IPI00418163.3 | HLVPGAPFLLQALVR | 15.53 | 5.25 | 2.95 |
| C4B | C4B1 | IPI:IPI00418163.3 | LGQYASPTAKR | 0.17 | 0.26 | 0.64 |
| C4B | C4B1 | IPI:IPI00418163.3 | LNMGITDLQGLR | 72.56 | 46.19 | 1.57 |
| C4B | C4B1 | IPI:IPI00418163.3 | LQETSNWLLSQQQADGSFQDLSPVIHR | 30.40 | 17.38 | 1.75 |
| C4B | C4B1 | IPI:IPI00418163.3 | LVNGQSHISLSK | 0.48 | 0.55 | 0.87 |
| C4B | C4B1 | IPI:IPI00418163.3 | PNMIPDGDFNSYVR | 0.43 | | |
| C4B | C4B1 | IPI:IPI00418163.3 | PVAFSVVPTAATAVSLK | 1.05 | 7.66 | 0.14 |
| C4B | C4B1 | IPI:IPI00418163.3 | SMQGGLVGNDETVALTAFVTIALHHGLAVFQDEGAEPLKQR | 0.40 | 0.13 | 3.05 |
| C4B | C4B1 | IPI:IPI00418163.3 | SPSVVHLGVPLSVGVQLQDVPR | 0.45 | 0.70 | 0.64 |
| C4B | C4B1 | IPI:IPI00418163.3 | TITVMVENSHGLR | | 0.29 | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| C4BPA | C4b-binding protein alpha chain | IPI:IPI00021727.1 | GVGWSHPLPQCEIVK | | 0.29 | |
| C5 | Complement C5 | IPI:IPI00032291.2 | ATLLDIYK | 5.86 | 7.64 | 0.77 |
| C5 | Complement C5 | IPI:IPI00032291.2 | DSLDQLVGGVPVTLNAQTIDVNQETSDLDPSK | 3.49 | 4.51 | 0.77 |
| C5 | Complement C5 | IPI:IPI00032291.2 | EALQIK | 0.40 | 0.45 | 0.89 |
| C5 | Complement C5 | IPI:IPI00032291.2 | ETVLTFIDPEGSEVDMVEEIDHIGIISFPDFK | 8.40 | 10.50 | 0.80 |
| C5 | Complement C5 | IPI:IPI00032291.2 | IDTQDIEASHYR | 4.23 | 6.45 | 0.66 |
| C5 | Complement C5 | IPI:IPI00032291.2 | KIEEIAAK | 3.68 | 5.19 | 0.71 |
| C5 | Complement C5 | IPI:IPI00032291.2 | LKEGMLSIMSYR | 2.26 | 3.67 | 0.62 |
| C5 | Complement C5 | IPI:IPI00032291.2 | LQGTLPVEAR | 14.02 | 18.08 | 0.78 |
| C5 | Complement C5 | IPI:IPI00032291.2 | MVETTAYALLTSLNLKDINYVNPVIK | 0.47 | 4.22 | 0.11 |
| C5 | Complement C5 | IPI:IPI00032291.2 | NFEITIK | 4.50 | 6.52 | 0.69 |
| C5 | Complement C5 | IPI:IPI00032291.2 | QLPGGQNPVSYVYLEVVSK | 1.15 | 1.61 | 0.72 |
| C5 | Complement C5 | IPI:IPI00032291.2 | QYLIMGK | 2.80 | 3.67 | 0.76 |
| C5 | Complement C5 | IPI:IPI00032291.2 | TDAPDLPEENQAR | 2.67 | 4.11 | 0.65 |
| C5 | Complement C5 | IPI:IPI00032291.2 | TLLPVSKPEIR | 17.92 | 23.93 | 0.75 |
| C5 | Complement C5 | IPI:IPI00032291.2 | VFQFLEK | 10.48 | 15.04 | 0.70 |
| C5 | Complement C5 | IPI:IPI00032291.2 | VQVKDSLDQLVGGVPVTLNAQTIDVNQETSDLDPSK | | 1.18 | |
| C5 | Complement C5 | IPI:IPI00032291.2 | VVPEGVKR | 2.62 | 3.94 | 0.67 |
| C5 | Complement C5 | IPI:IPI00032291.2 | WLSEEQR | 3.06 | 4.30 | 0.71 |
| C5 | Complement C5 | IPI:IPI00032291.2 | YGMWTIK | 3.29 | 4.61 | 0.71 |
| C5 | Complement C5 | IPI:IPI00032291.2 | YNFSFR | 3.90 | 5.57 | 0.70 |
| C6 | Complement component 6 | IPI:IPI00009920.2 | IGESIELTCPK | 7.46 | 6.33 | 1.18 |
| C6 | Complement component 6 | IPI:IPI00009920.2 | LSEKHEGSFIQGAEK | 0.56 | 0.81 | 0.70 |
| C7 | Complement component C7 | IPI:IPI00296608.6 | AASGTQNNVLRGEPFIR | | 0.18 | |
| C7 | Complement component C7 | IPI:IPI00296608.6 | GGGAGFISGLSYLELDNPAGNK | 1.10 | 1.41 | 0.78 |
| C7 | Complement component C7 | IPI:IPI00296608.6 | VLFYVDSEKLK | 0.49 | 0.90 | 0.55 |
| C8A | Complement component C8 alpha chain | IPI:IPI00011252.1 | SLLQPNK | 6.84 | 9.99 | 0.68 |
| C8A | Complement component C8 alpha chain | IPI:IPI00011252.1 | YNPVVIDFEMQPIHEVLR | 1.61 | 1.47 | 1.09 |
| C8B | Complement component C8 beta chain | IPI:IPI00294395.1 | GGASEHITTLAYQELPTADLMQEWGDAVQYNPAIIK | 2.13 | 1.76 | 1.21 |
| C9 | Complement component C9 | IPI:IPI00022395.1 | KGVELK | 0.12 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| C9 | Complement component C9 | IPI:IPI00022395.1 | TEHYEEQIEAFK | 11.87 | 9.19 | 1.29 |
| CA1 | Carbonic anhydrase 1 | IPI:IPI00215983.3 | GGPFSDSYR | 0.94 | | |
| CA1 | Carbonic anhydrase 1 | IPI:IPI00215983.3 | HDTSLKPISVSYNPATAK | 2.31 | | |
| CA1 | Carbonic anhydrase 1 | IPI:IPI00215983.3 | SLLSNVEGDNAVPMQHNNRPTQPLK | 2.88 | | |
| CACNA2D1 | Dihydropyridine receptor alpha 2 subunit | IPI:IPI00470535.1 | TPNKIDLYDVR | 1.41 | 0.51 | 2.74 |
| CCDC89 | Coiled-coil domain-containing protein 89 | IPI:IPI00167663.1 | ERELNGK | 10.66 | 14.27 | 0.75 |
| CD14 | Monocyte differentiation antigen CD14 | IPI:IPI00029260.2 | AFPALTSLDLSDNPGLGER | 0.53 | 0.46 | 1.14 |
| CD14 | Monocyte differentiation antigen CD14 | IPI:IPI00029260.2 | ATVNPSAPR | 0.36 | 0.21 | 1.73 |
| CD14 | Monocyte differentiation antigen CD14 | IPI:IPI00029260.2 | FPAIQNLALR | 0.37 | 0.34 | 1.11 |
| CD14 | Monocyte differentiation antigen CD14 | IPI:IPI00029260.2 | ITGTMPPLPLEATGLALSSLR | 0.65 | 0.29 | 2.29 |
| CD14 | Monocyte differentiation antigen CD14 | IPI:IPI00029260.2 | LTVGAAQVPAQLLVGALR | 0.38 | 0.31 | 1.25 |
| CD14 | Monocyte differentiation antigen CD14 | IPI:IPI00029260.2 | SWLAELQQWLKPGLK | 0.33 | | |
| CDH5 | Cadherin-5 | IPI:IPI00012792.1 | VHDVNDNWPVFTHR | 0.52 | | |
| CDKL1 | cyclin-dependent kinase-like 1 | IPI:IPI00023527.5 | SDVDQLYLIR | | 0.37 | |
| CECR1 | Cat eye syndrome critical region protein 1 | IPI:IPI00303071.4 | WILLEDYRK | | 0.35 | |
| CEP110 | Centrosomal protein 110 kDa | IPI:IPI00376383.2 | AELEKER | 0.06 | 0.12 | 0.52 |
| CES1 | Isoform 1 of Liver carboxylesterase 1 | IPI:IPI00010180.4 | QEFGWLIPMQLMSYPLSEGQLDQK | 0.66 | | |
| CFB | Isoform 1 of Complement factor B (Fragment) | IPI:IPI00019591.1 | LEDSVTYHCSR | 0.38 | 0.38 | 0.98 |
| CFB | Isoform 1 of Complement factor B (Fragment) | IPI:IPI00019591.1 | LQDEDLGFL | 17.49 | 20.39 | 0.86 |
| CFB | Isoform 1 of Complement factor B (Fragment) | IPI:IPI00019591.1 | QLNEINYEDHKLK | 0.35 | 2.99 | 0.12 |
| CFD | Complement factor D preproprotein | IPI:IPI00165972.3 | LYDVLR | | 0.48 | |
| CFH | Isoform 1 of Complement factor H | IPI:IPI00029739.5 | IDVHLVPDR | 33.22 | 40.39 | 0.82 |
| CFI | Complement factor I | IPI:IPI00291867.3 | IVIEYVDR | 7.42 | 9.34 | 0.79 |
| CFI | Complement factor I | IPI:IPI00291867.3 | TMFICK | 0.50 | | |
| CFI | Complement factor I | IPI:IPI00291867.3 | VANYFDWISYHVGR | 0.21 | 0.36 | 0.57 |
| CFL1 | Cofilin-1 | IPI:IPI00012011.6 | EILVGDVGQTVDDPYATFVK | 0.21 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| CHIT1 | Isoform 3 of Chitotriosidase-1 | IPI:IPI00375364.1 | FTTLVQDLANAFQQEAQTSGK | 3.66 | 1.77 | 2.07 |
| CLEC3B | Tetranectin | IPI:IPI00009028.1 | KDVVNTK | 0.03 | 0.08 | 0.42 |
| CLEC3B | Tetranectin | IPI:IPI00009028.1 | LDTLAQEVALLK | 3.37 | 5.17 | 0.65 |
| CLEC3B | Tetranectin | IPI:IPI00009028.1 | MFEELK | 0.19 | 0.23 | 0.85 |
| CLEC3B | Tetranectin | IPI:IPI00009028.1 | SRLDTLAQEVALLK | 0.66 | 1.07 | 0.61 |
| CNDP1 | Beta-Ala-His dipeptidase | IPI:IPI00064667.4 | DGSTIPIAK | 0.41 | 0.27 | 1.52 |
| CNDP1 | Beta-Ala-His dipeptidase | IPI:IPI00064667.4 | HLEDVFSKR | | 0.16 | |
| CNDP1 | Beta-Ala-His dipeptidase | IPI:IPI00064667.4 | MFQEIVHK | | 0.20 | |
| CNTN1 | Isoform 1 of Contactin-1 | IPI:IPI00029751.1 | YVHKDETMSPSTAFQVK | 0.30 | | |
| COL1A2 | Collagen alpha-2(I) chain | IPI:IPI00304962.3 | DYEVDATLK | 0.19 | 0.30 | 0.63 |
| COL6A3 | alpha 3 type VI collagen isoform 1 | IPI:IPI00022200.2 | SDDEVDDPAVELK | 0.17 | 46.32 | 0.00 |
| CP | Ceruloplasmin | IPI:IPI00017601.1 | EVGPTNADPVCLAK | 8.29 | 11.01 | 0.75 |
| CP | Ceruloplasmin | IPI:IPI00017601.1 | KLISVDTEHSNIYLQNGPDR | 9.19 | 8.60 | 1.07 |
| CP | Ceruloplasmin | IPI:IPI00017601.1 | PDQVDKEDEDFQESNK | 0.26 | 0.44 | 0.59 |
| CP | Ceruloplasmin | IPI:IPI00017601.1 | PVWLGFLGPIIK | 0.31 | 0.37 | 0.85 |
| CPB2 | Isoform 1 of Carboxypeptidase B2 | IPI:IPI00329775.7 | YSFTIELR | 0.63 | 0.34 | 1.83 |
| CPN1 | Carboxypeptidase N catalytic chain | IPI:IPI00010295.1 | IVQLIQDTR | 2.44 | 3.28 | 0.74 |
| CPN1 | Carboxypeptidase N catalytic chain | IPI:IPI00010295.1 | TASTPTPDDKLFQK | 0.38 | 0.42 | 0.90 |
| CPN2 | similar to Carboxypeptidase N subunit 2 | IPI:IPI00738433.1 | AGGSWDLAVQER | 0.99 | 1.29 | 0.77 |
| CPN2 | similar to Carboxypeptidase N subunit 2 | IPI:IPI00738433.1 | LSNNALSGLPQGVFGK | 2.44 | 3.86 | 0.63 |
| CR2 | Isoform B of Complement receptor type 2 | IPI:IPI00216985.1 | CVIAGQGVAWTK | 0.80 | | |
| CRP | C-reactive protein | IPI:IPI00022389.1 | AFVFPK | 7.08 | 4.75 | 1.49 |
| CRP | C-reactive protein | IPI:IPI00022389.1 | APLTKPLK | 15.53 | 5.33 | 2.92 |
| CRP | C-reactive protein | IPI:IPI00022389.1 | ESDTSYVSLK | 27.67 | 7.66 | 3.61 |
| CRP | C-reactive protein | IPI:IPI00022389.1 | GYSIFSYATK | 23.94 | 12.45 | 1.92 |
| CRP | C-reactive protein | IPI:IPI00022389.1 | KAFVFPK | 24.11 | 5.76 | 4.19 |
| CRP | C-reactive protein | IPI:IPI00022389.1 | QDNEILIFWSK | 3.60 | 3.94 | 0.91 |
| CRP | C-reactive protein | IPI:IPI00022389.1 | RQDNEILIFWSK | 24.62 | 17.36 | 1.42 |
| CRP | C-reactive protein | IPI:IPI00022389.1 | YEVQGEVFTKPQLWP | 19.78 | 11.80 | 1.68 |
| CRYZ | Quinone oxidoreductase | IPI:IPI00000792.1 | VFEFGGPEVLK | 0.56 | | |
| CST3 | Cystatin-C | IPI:IPI00032293.1 | ASNDMYHSR | | 0.25 | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| CST3 | Cystatin-C | IPI:IPI00032293.1 | LVGGPMDASVEEEGVRR | | 1.32 | |
| CTSA | cathepsin A | IPI:IPI00640525.2 | YGDSGEQIAGFVK | | 0.33 | |
| CTSB | Cathepsin B | IPI:IPI00295741.4 | SGVYQHVTGEMMGGHAIR | 1.34 | 2.07 | 0.65 |
| CUL4A | Isoform 1 of Cullin-4A | IPI:IPI00419273.5 | RIESLIDR | 4.35 | 6.76 | 0.64 |
| DKK3 | Dickkopf-related protein 3 | IPI:IPI00002714.1 | LLDLITWELEPDGALDR | | 13.43 | |
| DSTN | Destrin | IPI:IPI00473014.5 | MIYASSK | 0.54 | 0.25 | 2.21 |
| ECM1 | Extracellular matrix protein 1 | IPI:IPI00645849.1 | NLPATDPLQR | 0.51 | 0.77 | 0.67 |
| EFEMP1 | Isoform 1 of EGF-containing fibulin-like extracellular matrix protein 1 | IPI:IPI00029658.1 | QTSPVSAMLVLVK | 0.15 | 0.46 | 0.34 |
| ERAP1 | Isoform 2 of Endoplasmic reticulum aminopeptidase 1 | IPI:IPI00165949.2 | DMNEVETQFK | | 0.18 | |
| ERC1 | Isoform 2 of ELKS/RAB6-interacting/CAST family member 1 | IPI:IPI00171230.6 | QTLNARDESIKK | | 0.28 | |
| F10 | Coagulation factor X | IPI:IPI00019576.1 | APACLPERDWAESTLMTQK | 0.62 | | |
| F10 | Coagulation factor X | IPI:IPI00019576.1 | MLEVPYVDR | 0.57 | 1.48 | 0.39 |
| F11 | Isoform 1 of Coagulation factor XI | IPI:IPI00008556.1 | ERPGVYTNVVEYVDWILEK | | 0.14 | |
| F11 | Isoform 1 of Coagulation factor XI | IPI:IPI00008556.1 | MAESGYDIALLK | 0.21 | 0.45 | 0.48 |
| F2 | Prothrombin (Fragment) | IPI:IPI00019568.1 | GQPSVLQVVNLPIVERPVCK | 0.42 | 0.68 | 0.62 |
| F2 | Prothrombin (Fragment) | IPI:IPI00019568.1 | IVEGSDAEIGMSPWQVMLFR | 12.26 | 18.80 | 0.65 |
| F2 | Prothrombin (Fragment) | IPI:IPI00019568.1 | SGIECQLWR | 0.24 | 0.57 | 0.42 |
| F2 | Prothrombin (Fragment) | IPI:IPI00019568.1 | SLEDKTERELLESYIDGR | | 3.18 | |
| F2 | Prothrombin (Fragment) | IPI:IPI00019568.1 | TATSEYQTFFNPR | 25.22 | 36.62 | 0.69 |
| F2 | Prothrombin (Fragment) | IPI:IPI00019568.1 | VIDQFGE | 19.63 | 27.80 | 0.71 |
| F5 | Coagulation factor V | IPI:IPI00022937.4 | ASEFLGYWEPR | | 0.10 | |
| FAM71A | Protein FAM71A | IPI:IPI00217863.2 | YAPIFESDFIQITK | 0.39 | 0.35 | 1.12 |
| FBXO32 | F-box only protein 32 | IPI:IPI00056487.1 | LDFSTAILDSR | | 0.16 | |
| FCGBP | IgGFc-binding protein | IPI:IPI00242956.4 | LLFDGDAHLLMSIPSPFR | | 0.21 | |
| FCGR3A | Low affinity immunoglobulin gamma Fc region receptor III-A | IPI:IPI00218834.9 | AVVFLEPQWYR | 0.41 | | |
| FCN3 | Isoform 1 of Ficolin-3 | IPI:IPI00293925.2 | FSEGTAGDSLSLHSGR | | 0.13 | |
| FGA | Isoform 1 of Fibrinogen alpha chain | IPI:IPI00021885.1 | MELERPGGNEITR | 14.64 | 0.77 | 19.07 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| FGA | Isoform 1 of Fibrinogen alpha chain | IPI:IPI00021885.1 | MELERPGGNEITR | 0.46 | 0.14 | 3.35 |
| FGA | Isoform 1 of Fibrinogen alpha chain | IPI:IPI00021885.1 | NPSSAGSWNSGSSGPGSTGNR | 2.82 | | |
| FGA | Isoform 1 of Fibrinogen alpha chain | IPI:IPI00021885.1 | SRIEVLKR | 0.30 | | |
| FGB | Fibrinogen beta chain | IPI:IPI00298497.3 | MGPTELLIEMEDWKGDK | | 0.40 | |
| FGG | Gamma-B of Fibrinogen gamma chain | IPI:IPI00021891.5 | HLISTQSAIPYALR | | 0.19 | |
| FGG | Gamma-B of Fibrinogen gamma chain | IPI:IPI00021891.5 | HLSPTGTTEFWLGNEK | | 0.22 | |
| FGG | Gamma-B of Fibrinogen gamma chain | IPI:IPI00021891.5 | KMLEEIMK | 0.37 | | |
| FGG | Gamma-B of Fibrinogen gamma chain | IPI:IPI00021891.5 | MIDAATLK | 1.23 | | |
| FGG | Gamma-B of Fibrinogen gamma chain | IPI:IPI00021891.5 | MIDAATLK | 2.25 | 0.76 | 2.97 |
| FLJ22662 | hypothetical protein LOC79887 | IPI:IPI00016255.4 | KDPYSR | | 0.33 | |
| FLJ45139 | CDNA FLJ45139 fis, clone BRAWH3039623 | IPI:IPI00418931.1 | TVSIPR | 62.56 | 77.85 | 0.80 |
| FLNA | filamin A, alpha isoform 1 | IPI:IPI00302592.2 | AFGPGLQGGSAGSPAR | 1.81 | 1.08 | 1.67 |
| FLNA | filamin A, alpha isoform 1 | IPI:IPI00302592.2 | AYGPGIEPTGNMVK | 3.41 | 0.56 | 6.13 |
| FLNA | filamin A, alpha isoform 1 | IPI:IPI00302592.2 | GKLDVQFSGLTK | 0.80 | 0.40 | 1.98 |
| FLNA | filamin A, alpha isoform 1 | IPI:IPI00302592.2 | IANLQTDLSDGLR | 2.05 | 1.14 | 1.80 |
| FLNA | filamin A, alpha isoform 1 | IPI:IPI00302592.2 | IQQNTFTR | 0.72 | 0.56 | 1.30 |
| FLNA | filamin A, alpha isoform 1 | IPI:IPI00302592.2 | LIALLEVLSQK | 1.88 | 1.57 | 1.20 |
| FLNA | filamin A, alpha isoform 1 | IPI:IPI00302592.2 | LPQLPITNFSR | 2.00 | 1.55 | 1.29 |
| FLNA | filamin A, alpha isoform 1 | IPI:IPI00302592.2 | TGVAVNKPAEFTVDAK | 1.17 | 0.45 | 2.57 |
| FLNA | filamin A, alpha isoform 1 | IPI:IPI00302592.2 | VDVGKDQEFTVK | 0.83 | 0.46 | 1.80 |
| FLNA | filamin A, alpha isoform 1 | IPI:IPI00302592.2 | VTAQGPGLEPSGNIANK | 2.24 | 1.02 | 2.20 |
| FLNA | filamin A, alpha isoform 1 | IPI:IPI00302592.2 | VTVLFAGQHIAK | 0.95 | 0.65 | 1.46 |
| FLNB | Isoform 1 of Filamin-B | IPI:IPI00289334.1 | IQQNTFTR | 0.72 | 0.56 | 1.30 |
| FLNB | Isoform 1 of Filamin-B | IPI:IPI00289334.1 | LIALLEVLSQK | 1.88 | 1.57 | 1.20 |
| FN1 | Isoform 1 of Fibronectin | IPI:IPI00022418.1 | GATYNIIVEALK | 0.41 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| FN1 | Isoform 1 of Fibronectin | IPI:IPI00022418.1 | ITGYIIK | 0.58 | | |
| FN1 | Isoform 1 of Fibronectin | IPI:IPI00022418.1 | SYTITGLQPGTDYK | 0.38 | | |
| FN1 | Isoform 1 of Fibronectin | IPI:IPI00022418.1 | VGDTYERPK | 0.13 | | |
| FN1 | Isoform 1 of Fibronectin | IPI:IPI00022418.1 | VTWAPPPSIDLTNFLVR | 0.49 | | |
| FN1 | Isoform 1 of Fibronectin | IPI:IPI00022418.1 | YEKPGSPPR | 0.21 | 0.04 | 5.18 |
| FTL | Ferritin light chain | IPI:IPI00738499.2 | LGGPEAGLGEYLFER | 2.66 | | |
| GAPDH | Glyceraldehyde-3-phosphate dehydrogenase | IPI:IPI00219018.7 | GALQNIIPASTGAAK | 2.28 | 1.61 | 1.42 |
| GAPDH | Glyceraldehyde-3-phosphate dehydrogenase | IPI:IPI00219018.7 | VDIVAINDPFIDLNYMVYMFQYDSTHGK | 0.81 | 1.39 | 0.58 |
| GAPDH | Glyceraldehyde-3-phosphate dehydrogenase | IPI:IPI00219018.7 | VVDLMAHMASKE | 1.18 | 0.57 | 2.08 |
| GC | Vitamin D-binding protein | IPI:IPI00555812.4 | DKYTFELSR | 0.63 | 0.17 | 3.70 |
| GC | Vitamin D-binding protein | IPI:IPI00555812.4 | ELSSFIDK | 15.57 | 10.11 | 1.54 |
| GC | Vitamin D-binding protein | IPI:IPI00555812.4 | SINSPPLYCDSEIDAELKNIL | | 0.13 | |
| GGH | Gamma-glutamyl hydrolase | IPI:IPI00023728.1 | MFQNFPTELLLSLAVEPLTANFHK | 0.18 | | |
| GGH | Gamma-glutamyl hydrolase | IPI:IPI00023728.1 | TAFYLAEFFVNEAR | 0.20 | | |
| GLRX | Glutaredoxin-1 | IPI:IPI00219025.3 | LKQIGALQ | 85.27 | 121.89 | 0.70 |
| GOLGA4 | Isoform 1 of Golgin subfamily A member 4 | IPI:IPI00013272.1 | EFNTQLAQKE | 0.20 | | |
| GP1BA | platelet glycoprotein Ib alpha polypeptide | IPI:IPI00748955.2 | LTSLPLGALR | 0.87 | 0.91 | 0.95 |
| GP1BA | platelet glycoprotein Ib alpha polypeptide | IPI:IPI00748955.2 | TLPPGLLTPTPK | 0.46 | 0.30 | 1.56 |
| GPLD1 | Isoform 1 of Phosphatidylinositol-glycan-specific phospholipase D | IPI:IPI00299503.2 | FGGVLHLSDLDDDGLDEIIMAAPLR | 0.22 | 0.56 | 0.40 |
| GPLD1 | Isoform 1 of Phosphatidylinositol-glycan-specific phospholipase D | IPI:IPI00299503.2 | ILEGFQPSGR | 0.32 | 0.57 | 0.56 |
| GPT | Alanine amino-transferase 1 | IPI:IPI00217458.3 | LLVAGEGHTR | 0.11 | | |
| GRM5 | glutamate receptor, metabotropic 5 | IPI:IPI00789949.1 | KRDQTLMLSFMR | 0.96 | 1.62 | 0.59 |
| GSG1L | GSG1-like isoform 1 | IPI:IPI00152159.3 | SFIDLAPASEK | 0.73 | 0.58 | 1.26 |
| GSN | Gelsolin | IPI:IPI00026314.1 | AGALNSNDAFVLK | 12.54 | 24.33 | 0.52 |
| GSN | Gelsolin | IPI:IPI00026314.1 | AGKEPGLQIWR | 5.68 | 12.22 | 0.47 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| GSN | Gelsolin | IPI:IPI00026314.1 | AQPVQVAEGSEPDGFWEALGGK | 2.43 | 5.88 | 0.41 |
| GSN | Gelsolin | IPI:IPI00026314.1 | AVEVLPK | 1.49 | 2.94 | 0.51 |
| GSN | Gelsolin | IPI:IPI00026314.1 | DSQEEEKTEALTSAK | 0.76 | 1.43 | 0.54 |
| GSN | Gelsolin | IPI:IPI00026314.1 | EGGQTAPASTR | 0.23 | 0.36 | 0.64 |
| GSN | Gelsolin | IPI:IPI00026314.1 | EVQGFESATFLGYFK | 5.76 | 11.95 | 0.48 |
| GSN | Gelsolin | IPI:IPI00026314.1 | GASQAGAPQGR | 1.32 | 2.71 | 0.49 |
| GSN | Gelsolin | IPI:IPI00026314.1 | GGVASGFK | 0.31 | 0.61 | 0.51 |
| GSN | Gelsolin | IPI:IPI00026314.1 | HVVPNEVVVQR | 9.30 | 19.43 | 0.48 |
| GSN | Gelsolin | IPI:IPI00026314.1 | IEGSNKVPVDPATYGQFYGGDSYIILYNYR | 2.55 | 4.09 | 0.63 |
| GSN | Gelsolin | IPI:IPI00026314.1 | MDAHPPR | 1.71 | 3.33 | 0.51 |
| GSN | Gelsolin | IPI:IPI00026314.1 | PALPAGTEDTAKEDAANR | 0.16 | 0.28 | 0.57 |
| GSN | Gelsolin | IPI:IPI00026314.1 | QTQVSVLPEGGETPLFK | 9.00 | 19.74 | 0.46 |
| GSN | Gelsolin | IPI:IPI00026314.1 | RYIETDPANR | 0.21 | 0.37 | 0.56 |
| GSN | Gelsolin | IPI:IPI00026314.1 | TASDFITK | 6.07 | 12.18 | 0.50 |
| GSN | Gelsolin | IPI:IPI00026314.1 | TGAQELLR | 8.51 | 17.56 | 0.48 |
| GSN | Gelsolin | IPI:IPI00026314.1 | TPITVVK | 0.66 | 1.32 | 0.50 |
| GSN | Gelsolin | IPI:IPI00026314.1 | TPSAAYLWVGTGASEAEK | 2.75 | 5.59 | 0.49 |
| GSN | Gelsolin | IPI:IPI00026314.1 | TPSAAYLWVGTGASEAEKTGAQELLR | 1.04 | 3.40 | 0.31 |
| GSN | Gelsolin | IPI:IPI00026314.1 | VPEARPNSMVVEHPEFLK | 5.34 | 12.46 | 0.43 |
| GSN | Gelsolin | IPI:IPI00026314.1 | VPFDAATLHTSTAMAAQHGMDDDGTGQK | 7.35 | 15.87 | 0.46 |
| GSN | Gelsolin | IPI:IPI00026314.1 | YIETDPANR | 1.99 | 4.32 | 0.46 |
| GULP1 | Isoform 1 of PTB domain-containing engulfment adapter protein 1 | IPI:IPI00790010.1 | IQDLETENMELK | 1.14 | | |
| HBA2; HBA1 | Hemoglobin subunit alpha | IPI:IPI00410714.5 | MFLSFPTTK | 10.38 | 26.76 | 0.39 |
| HELLS | Isoform 1 of Lymphoid-specific helicase | IPI:IPI00010590.2 | NKDSNSIIK | 0.17 | | |
| HGFAC | Hepatocyte growth factor activator | IPI:IPI00029193.1 | EALVPLVADHK | 0.41 | 0.52 | 0.77 |
| HOM-TES-1 | hypothetical protein LOC25900 isoform 4 | IPI:IPI00022868.3 | MKVDMDICR | 0.44 | 0.43 | 1.04 |
| HP | Haptoglobin | IPI:IPI00641737.1 | HYEGSTVPEK | 3.73 | 1.42 | 2.62 |
| HP | Haptoglobin | IPI:IPI00641737.1 | LRTEGDGVYTLNDK | 10.04 | 0.37 | 27.05 |
| HP | Haptoglobin | IPI:IPI00641737.1 | PECEAVCGKPK | | 0.09 | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| HPR | Isoform 1 of Haptoglobin-related protein | IPI:IPI00477597.1 | LRTEGDGVYTLNDK | 10.04 | 0.37 | 27.05 |
| HPR | Isoform 1 of Haptoglobin-related protein | IPI:IPI00477597.1 | PECEAVCGKPK | | 0.09 | |
| HPX | Hemopexin | IPI:IPI00022488.1 | EVGTPHGIILDSVDAAFICPGSSR | 0.90 | 1.92 | 0.47 |
| HPX | Hemopexin | IPI:IPI00022488.1 | VDGALCMEK | 3.41 | 3.81 | 0.90 |
| HPX | Hemopexin | IPI:IPI00022488.1 | YYCFQGNQFLR | 3.47 | 5.76 | 0.60 |
| HRG | Histidine-rich glycoprotein | IPI:IPI00022371.1 | DVEALDLESPK | | 0.24 | |
| HSPA8 | Heat shock 70 kDa protein 8 isoform 2 variant (Fragment) | IPI:IPI00795040.1 | DAGTIAGLNVLR | 0.33 | | |
| HSPA8 | Heat shock 70 kDa protein 8 isoform 2 variant (Fragment) | IPI:IPI00795040.1 | NQVAMNPTNTVFDAKR | 0.30 | | |
| ICAM1 | Intercellular adhesion molecule 1 | IPI:IPI00008494.4 | LLGIETPLPK | 0.80 | | |
| ICAM1 | Intercellular adhesion molecule 1 | IPI:IPI00008494.4 | VELAPLPSWQPVGK | 0.57 | | |
| IGF1 | Insulin-like growth factor IA | IPI:IPI00001610.1 | RLEMYCAPLKPAK | | 0.37 | |
| IGFALS | Insulin-like growth factor-binding protein complex acid labile chain | IPI:IPI00020996.3 | LAYLQPALFSGLAELR | 3.49 | 3.14 | 1.11 |
| IGFALS | Insulin-like growth factor-binding protein complex acid labile chain | IPI:IPI00020996.3 | NLIAAVAPGAFLGLK | 2.08 | 2.02 | 1.03 |
| IGFBP2 | Insulin-like growth factor-binding protein 2 | IPI:IPI00297284.1 | GGKHHLGLEEPK | | 0.17 | |
| IGFBP6 | Insulin-like growth factor-binding protein 6 | IPI:IPI00029235.1 | HLDSVLQQLQTEVYR | | 0.28 | |
| IGHM | IGHM protein | IPI:IPI00477090.6 | LICQATGFSPR | | 0.25 | |
| IGL@ | IGL@ protein | IPI:IPI00154742.6 | ATLVCLISDFYPGAVTVAWK | 1.60 | 0.45 | 3.58 |
| IGLV7-43 | Ig lambda chain V region 4A | IPI:IPI00022890.1 | FSGSLLGGK | 0.38 | | |
| ITGA2B | integrin alpha 2b preproprotein | IPI:IPI00218629.2 | NVGSQTLQTFK | | 0.25 | |
| ITIH1 | Inter-alpha-trypsin inhibitor heavy chain H1 | IPI:IPI00292530.1 | DTAVDGVFIR | | 0.13 | |
| ITIH1 | Inter-alpha-trypsin inhibitor heavy chain H1 | IPI:IPI00292530.1 | ELAAQTIKK | 8.21 | 14.31 | 0.57 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| ITIH1 | Inter-alpha-trypsin inhibitor heavy chain H1 | IPI:IPI00292530.1 | EVAFDLEIPK | 28.72 | 46.70 | 0.62 |
| ITIH1 | Inter-alpha-trypsin inhibitor heavy chain H1 | IPI:IPI00292530.1 | FAHYVVTSQVVNTANEAR | 10.92 | 17.76 | 0.61 |
| ITIH1 | Inter-alpha-trypsin inhibitor heavy chain H1 | IPI:IPI00292530.1 | GHMLENHVER | 6.40 | 11.30 | 0.57 |
| ITIH1 | Inter-alpha-trypsin inhibitor heavy chain H1 | IPI:IPI00292530.1 | GIEILNQVQESLPELSNHASI LIMLTDGDPTEGVTDR | 3.42 | 4.93 | 0.69 |
| ITIH1 | Inter-alpha-trypsin inhibitor heavy chain H1 | IPI:IPI00292530.1 | GMADQDGLKPTIDKPSEDSP PLEMLGPR | 27.16 | 43.87 | 0.62 |
| ITIH1 | Inter-alpha-trypsin inhibitor heavy chain H1 | IPI:IPI00292530.1 | GSLVQASEANLQAAQDFVR | 15.68 | 24.71 | 0.63 |
| ITIH1 | Inter-alpha-trypsin inhibitor heavy chain H1 | IPI:IPI00292530.1 | IADNKQSSFK | 0.86 | 1.16 | 0.74 |
| ITIH1 | Inter-alpha-trypsin inhibitor heavy chain H1 | IPI:IPI00292530.1 | ILGDMQPGDYFDLVLFGTR | 22.32 | 47.17 | 0.47 |
| ITIH1 | Inter-alpha-trypsin inhibitor heavy chain H1 | IPI:IPI00292530.1 | KAAISGENAGLVR | 7.53 | 12.44 | 0.61 |
| ITIH1 | Inter-alpha-trypsin inhibitor heavy chain H1 | IPI:IPI00292530.1 | MSLDYGFVTPLTSMSIR | 10.01 | 17.68 | 0.57 |
| ITIH1 | Inter-alpha-trypsin inhibitor heavy chain H1 | IPI:IPI00292530.1 | MSLDYGFVTPLTSMSIR | | 0.28 | |
| ITIH1 | Inter-alpha-trypsin inhibitor heavy chain H1 | IPI:IPI00292530.1 | NHMQYEIVIK | 11.50 | 17.77 | 0.65 |
| ITIH1 | Inter-alpha-trypsin inhibitor heavy chain H1 | IPI:IPI00292530.1 | QAVDTAVDGVFIR | 10.25 | 16.99 | 0.60 |
| ITIH1 | Inter-alpha-trypsin inhibitor heavy chain H1 | IPI:IPI00292530.1 | QYYEGSEIVVAGR | 2.23 | 1.21 | 1.84 |
| ITIH1 | Inter-alpha-trypsin inhibitor heavy chain H1 | IPI:IPI00292530.1 | RQAVDTAVDGVFIR | 0.50 | 0.58 | 0.86 |
| ITIH1 | Inter-alpha-trypsin inhibitor heavy chain H1 | IPI:IPI00292530.1 | VTFQLTYEEVLKR | 5.67 | 7.77 | 0.73 |
| ITIH1 | Inter-alpha-trypsin inhibitor heavy chain H1 | IPI:IPI00292530.1 | VTYDVSR | 6.57 | 10.00 | 0.66 |
| ITIH2 | Inter-alpha-trypsin inhibitor heavy chain H2 | IPI:IPI00305461.2 | AIFILNEANNLGLLDPNSVSL IILVSDGDPTVGELK | 4.89 | 8.31 | 0.59 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| ITIH2 | Inter-alpha-trypsin inhibitor heavy chain H2 | IPI:IPI00305461.2 | DKHADPDFTR | 3.35 | 5.99 | 0.56 |
| ITIH2 | Inter-alpha-trypsin inhibitor heavy chain H2 | IPI:IPI00305461.2 | ENIQDNISLFSLGMGFDVDYDFLKR | 2.43 | 4.88 | 0.50 |
| ITIH2 | Inter-alpha-trypsin inhibitor heavy chain H2 | IPI:IPI00305461.2 | FDPAKLDQIESVITATSANTQLVLETLAQMDDLQDFLSK | 6.94 | 12.15 | 0.57 |
| ITIH2 | Inter-alpha-trypsin inhibitor heavy chain H2 | IPI:IPI00305461.2 | FDPAKLDQIESVITATSANTQLVLETLAQMDDLQDFLSK | 6.94 | 12.15 | 0.57 |
| ITIH2 | Inter-alpha-trypsin inhibitor heavy chain H2 | IPI:IPI00305461.2 | FDPAKLDQIESVITATSANTQLVLETLAQMDDLQDFLSK | | 0.09 | |
| ITIH2 | Inter-alpha-trypsin inhibitor heavy chain H2 | IPI:IPI00305461.2 | FLHVPDTFEGHFDGVPVISK | 42.05 | 67.72 | 0.62 |
| ITIH2 | Inter-alpha-trypsin inhibitor heavy chain H2 | IPI:IPI00305461.2 | FYNQVSTPLLR | 31.04 | 54.21 | 0.57 |
| ITIH2 | Inter-alpha-trypsin inhibitor heavy chain H2 | IPI:IPI00305461.2 | HADPDFTR | 8.05 | 12.82 | 0.63 |
| ITIH2 | Inter-alpha-trypsin inhibitor heavy chain H2 | IPI:IPI00305461.2 | IQPSGGTNINEALLR | 45.53 | 79.08 | 0.58 |
| ITIH2 | Inter-alpha-trypsin inhibitor heavy chain H2 | IPI:IPI00305461.2 | IYGNQDTSSQLK | 3.74 | 4.70 | 0.80 |
| ITIH2 | Inter-alpha-trypsin inhibitor heavy chain H2 | IPI:IPI00305461.2 | IYGNQDTSSQLKK | 8.17 | 13.87 | 0.59 |
| ITIH2 | Inter-alpha-trypsin inhibitor heavy chain H2 | IPI:IPI00305461.2 | IYLQPGR | 17.11 | 30.41 | 0.56 |
| ITIH2 | Inter-alpha-trypsin inhibitor heavy chain H2 | IPI:IPI00305461.2 | KLGSYEHR | 3.86 | 7.12 | 0.54 |
| ITIH2 | Inter-alpha-trypsin inhibitor heavy chain H2 | IPI:IPI00305461.2 | LDQIESVITATSANTQLVLETLAQMDDLQDFLSK | 4.61 | 4.60 | 1.00 |
| ITIH2 | Inter-alpha-trypsin inhibitor heavy chain H2 | IPI:IPI00305461.2 | LGSYEHR | 3.06 | 4.94 | 0.62 |
| ITIH2 | Inter-alpha-trypsin inhibitor heavy chain H2 | IPI:IPI00305461.2 | LSNENHGIAQR | 10.44 | 16.74 | 0.62 |
| ITIH2 | Inter-alpha-trypsin inhibitor heavy chain H2 | IPI:IPI00305461.2 | MATTMIQSK | 20.18 | 33.27 | 0.61 |
| ITIH2 | Inter-alpha-trypsin inhibitor heavy chain H2 | IPI:IPI00305461.2 | MKQTVEAMK | 4.20 | 7.89 | 0.53 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| ITIH2 | Inter-alpha-trypsin inhibitor heavy chain H2 | IPI:IPI00305461.2 | NDLISATK | 11.30 | 17.66 | 0.64 |
| ITIH2 | Inter-alpha-trypsin inhibitor heavy chain H2 | IPI:IPI00305461.2 | NVKENIQDNISLFSLGMGFDVDYDFLKR | | 0.18 | |
| ITIH2 | Inter-alpha-trypsin inhibitor heavy chain H2 | IPI:IPI00305461.2 | NVQFNYPHTSVTDVTQNNFHNYFGGSEIVVAGK | 6.10 | 9.78 | 0.62 |
| ITIH2 | Inter-alpha-trypsin inhibitor heavy chain H2 | IPI:IPI00305461.2 | PSGGTNINEALLR | 1.96 | 4.07 | 0.48 |
| ITIH2 | Inter-alpha-trypsin inhibitor heavy chain H2 | IPI:IPI00305461.2 | SSALDMENFR | 29.97 | 50.84 | 0.59 |
| ITIH2 | Inter-alpha-trypsin inhibitor heavy chain H2 | IPI:IPI00305461.2 | SSALDMENFR | 0.20 | 0.32 | 0.62 |
| ITIH2 | Inter-alpha-trypsin inhibitor heavy chain H2 | IPI:IPI00305461.2 | TAGLVR | 5.34 | 9.84 | 0.54 |
| ITIH2 | Inter-alpha-trypsin inhibitor heavy chain H2 | IPI:IPI00305461.2 | TEVNVLPGAK | 29.65 | 49.53 | 0.60 |
| ITIH2 | Inter-alpha-trypsin inhibitor heavy chain H2 | IPI:IPI00305461.2 | TILDDLRAEDHFSVIDFNQNIR | 29.54 | 49.72 | 0.59 |
| ITIH2 | Inter-alpha-trypsin inhibitor heavy chain H2 | IPI:IPI00305461.2 | TWRNDLISATK | 2.54 | 4.23 | 0.60 |
| ITIH2 | Inter-alpha-trypsin inhibitor heavy chain H2 | IPI:IPI00305461.2 | VQFELHYQEVK | 10.70 | 23.59 | 0.45 |
| ITIH2 | Inter-alpha-trypsin inhibitor heavy chain H2 | IPI:IPI00305461.2 | VQSTITSR | 15.02 | 25.32 | 0.59 |
| ITIH2 | Inter-alpha-trypsin inhibitor heavy chain H2 | IPI:IPI00305461.2 | VVNNSPQPQNVVFDVQIPK | 17.70 | 31.88 | 0.56 |
| ITIH3 | Isoform 1 of Inter-alpha-trypsin inhibitor heavy chain H3 | IPI:IPI00028413.8 | AREEHRIPER | 0.21 | 0.57 | 0.36 |
| ITIH3 | Isoform 1 of Inter-alpha-trypsin inhibitor heavy chain H3 | IPI:IPI00028413.8 | ESPGNVQIVNGYFVHFFAPQGLPVVPK | 0.48 | 0.56 | 0.86 |
| ITIH3 | Isoform 1 of Inter-alpha-trypsin inhibitor heavy chain H3 | IPI:IPI00028413.8 | MSAQTHGLLGQFFQPFDFK | 0.35 | | |
| ITIH3 | Isoform 1 of Inter-alpha-trypsin inhibitor heavy chain H3 | IPI:IPI00028413.8 | SMEDKGMTNINDGLLR | 0.15 | 0.78 | 0.19 |
| ITIH3 | Isoform 1 of Inter-alpha-trypsin inhibitor heavy chain H3 | IPI:IPI00028413.8 | TAGLVK | 4.87 | 7.26 | 0.67 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| ITIH3 | Isoform 1 of Inter-alpha-trypsin inhibitor heavy chain H3 | IPI:IPI00028413.8 | VSDIRPGSDPTKPDATLVVK | 0.66 | | |
| ITIH4 | Isoform 1 of Inter-alpha-trypsin inhibitor heavy chain H4 | IPI:IPI00294193.4 | FAHTVVTSR | 35.36 | 43.76 | 0.81 |
| ITIH4 | Isoform 1 of Inter-alpha-trypsin inhibitor heavy chain H4 | IPI:IPI00294193.4 | ILDDLSPR | 41.07 | 49.94 | 0.82 |
| ITIH4 | Isoform 1 of Inter-alpha-trypsin inhibitor heavy chain H4 | IPI:IPI00294193.4 | NVVFVIDK | 27.71 | 34.54 | 0.80 |
| ITIH4 | Isoform 1 of Inter-alpha-trypsin inhibitor heavy chain H4 | IPI:IPI00294193.4 | SAGLVK | 5.38 | 6.71 | 0.80 |
| KIAA0423 | Isoform 1 of Uncharacterized protein KIAA0423 | IPI:IPI00744872.2 | LHDSNSK | | 0.23 | |
| KLKB1 | Plasma kallikrein | IPI:IPI00654888.4 | YSPGGTPTAIK | 2.25 | 3.35 | 0.67 |
| KNG1 | Kininogen-1 | IPI:IPI00032328.2 | AATGECTATVGKR | 0.38 | 0.72 | 0.53 |
| KNG1 | Kininogen-1 | IPI:IPI00032328.2 | AVDAALKK | 18.44 | 29.10 | 0.63 |
| KNG1 | Kininogen-1 | IPI:IPI00032328.2 | DIPTNSPELEETLTHTITK | 47.87 | 61.90 | 0.77 |
| KNG1 | Kininogen-1 | IPI:IPI00032328.2 | KYFIDFVAR | 18.42 | 24.78 | 0.74 |
| KNG1 | Kininogen-1 | IPI:IPI00032328.2 | QVVAGLNFR | 23.86 | 34.40 | 0.69 |
| KNG1 | Isoform HMW of Kininogen-1 | IPI:IPI00032328.2 | SVSEINPTTQMK | 0.20 | 0.42 | 0.49 |
| KNG1 | Kininogen-1 | IPI:IPI00032328.2 | YFIDFVAR | 28.85 | 40.11 | 0.72 |
| KRT10 | Keratin, type I cytoskeletal 10 | IPI:IPI00009865.2 | GSLGGGFSSGGFSGGSFSR | 2.13 | | |
| KRT10 | Keratin, type I cytoskeletal 10 | IPI:IPI00009865.2 | SKELTTEIDNNIEQISSYK | 3.04 | 3.69 | 0.83 |
| KRT10 | Keratin, type I cytoskeletal 10 | IPI:IPI00009865.2 | VTMQNLNDR | 1.07 | 0.19 | 5.65 |
| KRT2 | Keratin, type II cytoskeletal 2 epidermal | IPI:IPI00021304.1 | NLDLDSIIAEVKAQYEEIAQR | 3.75 | | |
| KRT2 | Keratin, type II cytoskeletal 2 epidermal | IPI:IPI00021304.1 | VDLLNQEIEFLK | 1.00 | | |
| LBP | Lipopolysaccharide-binding protein | IPI:IPI00032311.4 | ATAQMLEVMFK | 0.88 | | |
| LBP | Lipopolysaccharide-binding protein | IPI:IPI00032311.4 | GLQYAAQEGLLALQSELLR | 0.36 | | |
| LBP | Lipopolysaccharide-binding protein | IPI:IPI00032311.4 | ITGFLKPGK | 0.61 | | |
| LBP | Lipopolysaccharide-binding protein | IPI:IPI00032311.4 | ITLPDFTGDLR | 1.32 | | |
| LBP | Lipopolysaccharide-binding protein | IPI:IPI00032311.4 | SFRPFVPR | 0.59 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
| --- | --- | --- | --- | --- | --- | --- |
| LBP | Lipopolysaccharide-binding protein | IPI:IPI00032311.4 | SPVTLLAAVMSLPEEHNK | 0.70 | | |
| LCP1 | Plastin-2 | IPI:IPI00010471.5 | FSLVGIGGQDLNEGNR | 0.43 | | |
| LCP1 | Plastin-2 | IPI:IPI00010471.5 | IKVPVDWNR | 0.27 | | |
| LCP1 | Plastin-2 | IPI:IPI00010471.5 | QFVTATDVVR | 0.49 | | |
| LDHB | L-lactate dehydrogenase B chain | IPI:IPI00219217.3 | GLTSVINQK | 0.47 | 0.29 | 1.64 |
| LDHB | L-lactate dehydrogenase B chain | IPI:IPI00219217.3 | IVADKDYSVTANSK | 0.16 | 0.06 | 2.44 |
| LIFR | Leukemia inhibitory factor receptor | IPI:IPI00444272.2 | QFLIPPK | 409.27 | 695.10 | 0.59 |
| LPA | Apolipoprotein | IPI:IPI00029168.1 | GTLSTTITGR | 0.37 | 0.36 | 1.01 |
| LPA | Apolipoprotein | IPI:IPI00029168.1 | GTYSTTVTGR | 1.57 | 5.41 | 0.29 |
| LRG1 | Leucine-rich alpha-2-glycoprotein | IPI:IPI00022417.4 | LGHLDLSGNR | 0.25 | 0.22 | 1.13 |
| LUM | Lumican | IPI:IPI00020986.2 | FNALQYLR | 2.01 | 4.54 | 0.44 |
| LUM | Lumican | IPI:IPI00020986.2 | LKEDAVSAAFK | 6.20 | 12.80 | 0.48 |
| LUM | Lumican | IPI:IPI00020986.2 | LPSGLPVSLLTLYLDNNK | 1.43 | 3.74 | 0.38 |
| LUM | Lumican | IPI:IPI00020986.2 | NIPTVNENLENYYLEVNQLEK | 0.94 | 2.93 | 0.32 |
| LUM | Lumican | IPI:IPI00020986.2 | NNQIDHIDEK | 0.22 | 0.61 | 0.37 |
| LUM | Lumican | IPI:IPI00020986.2 | SLEDLQLTHNK | 6.71 | 13.68 | 0.49 |
| LUM | Lumican | IPI:IPI00020986.2 | SLEYLDLSFNQIAR | 2.86 | 6.69 | 0.43 |
| LUM | Lumican | IPI:IPI00020986.2 | SVPMVPPGIK | 2.29 | 4.55 | 0.50 |
| MASP1 | mannan-binding lectin serine protease 1 isoform 2 | IPI:IPI00290283.6 | TLSDVLQYVK | 0.18 | 0.29 | 0.64 |
| MBL2 | Mannose-binding protein C | IPI:IPI00004373.1 | FQASVATPR | 4.84 | 2.46 | 1.97 |
| MCAM | Isoform 1 of Cell surface glycoprotein MUC18 | IPI:IPI00016334.2 | IFLCQGK | 2.53 | 1.50 | 1.68 |
| MED12L | Isoform 4 of Mediator of RNA polymerase II transcription subunit 12-like protein | IPI:IPI00044353.6 | LDPAGSFVPTNTK | | 0.41 | |
| MEGF8 | Isoform 1 of Multiple epidermal growth factor-like domains 8 | IPI:IPI00027310.4 | SFHAAAYVPAGR | 5.16 | 8.22 | 0.63 |
| MMP8 | Neutrophil collagenase | IPI:IPI00027846.1 | YYAFDLIAQR | | 0.45 | |
| MSN | Moesin | IPI:IPI00219365.3 | IGFPWSEIR | 0.27 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
| --- | --- | --- | --- | --- | --- | --- |
| MTMR15 | Isoform 1 of Coiled-coil domain-containing protein MTMR15 | IPI:IPI00007317.4 | RLEPTIK | 27.01 | 34.25 | 0.79 |
| MYCBP2 | Putative uncharacterized protein DKFZp586G0322 (Fragment) | IPI:IPI00383833.1 | KECEKENK | | 1.11 | |
| NRCAM | Isoform 1 of Neuronal cell adhesion molecule | IPI:IPI00333776.5 | DSTGTYTCVAR | 0.16 | | |
| NRP1 | Neuropilin 1 | IPI:IPI00398715.5 | IKPATWETGISMR | 0.33 | | |
| OLFM1 | Isoform 1 of Noelin | IPI:IPI00017841.2 | VSNLEER | 1.10 | 1.90 | 0.58 |
| ORM1 | Alpha-1-acid glycoprotein 1 | IPI:IPI00022429.3 | YVGGQEHFAHLLILR | 2.42 | 3.78 | 0.64 |
| PCSK9 | Isoform 1 of Proprotein convertase subtilisin/ kexin type 9 | IPI:IPI00387168.1 | VMVTDFENVPEEDGTR | 0.67 | 0.33 | 2.00 |
| PCYOX1 | Prenylcysteine oxidase 1 | IPI:IPI00384280.5 | LFLSYDYAVK | | 0.11 | |
| PDIA3 | Protein disulfide- isomerase A3 | IPI:IPI00025252.1 | ELSDFISYLQR | 0.23 | | |
| PDIA3 | Protein disulfide- isomerase A3 | IPI:IPI00025252.1 | TFSHELSDFGLESTAGEIPVV AIR | 0.23 | | |
| PDIA3 | Protein disulfide- isomerase A3 | IPI:IPI00025252.1 | YGVSGYPTLK | 0.33 | 0.45 | 0.72 |
| PEBP4 | PEBP family protein | IPI:IPI00163563.3 | HWLVTDIK | | 0.37 | |
| PFN1 | Profilin-1 | IPI:IPI00216691.5 | DSLLQDGEFSMDLR | 1.52 | 1.28 | 1.19 |
| PGLYRP2 | N-acetylmuramoyl-L- alanine amidase | IPI:IPI00163207.1 | AGLLRPDYALLGHR | 2.21 | 3.02 | 0.73 |
| PGLYRP2 | Isoform 1 of N- acetylmuramoyl-L-alanine amidase | IPI:IPI00163207.1 | EGKEYGVVLAPDGSTVAVE PLLAGLEAGLQGR | 1.60 | 3.38 | 0.47 |
| PGLYRP2 | Isoform 1 of N- acetylmuramoyl-L-alanine amidase | IPI:IPI00163207.1 | RVINLPLDSMAAPWETGDT FPDVVAIAPDVR | 0.81 | 0.86 | 0.94 |
| PGLYRP2 | Isoform 1 of N- acetylmuramoyl-L-alanine amidase | IPI:IPI00163207.1 | TFTLLDPK | 3.40 | 6.16 | 0.55 |
| PGLYRP2 | Isoform 1 of N- acetylmuramoyl-L-alanine amidase | IPI:IPI00163207.1 | WGAAPYR | 0.73 | 0.57 | 1.27 |
| PI16 | Isoform 1 of Peptidase inhibitor 16 | IPI:IPI00301143.5 | AQVSPTASDMLHMR | | 0.37 | |
| PI16 | Isoform 1 of Peptidase inhibitor 16 | IPI:IPI00301143.5 | LMVELHNLYR | 0.19 | 0.68 | 0.27 |
| PLEK | Pleckstrin | IPI:IPI00306311.8 | NRQEGLMIASSLLNEGYLQP AGDMSK | 0.32 | 0.53 | 0.60 |
| PNP | Purine nucleoside phosphorylase | IPI:IPI00871140.1 | VIMDYESLEK | 0.16 | | |
| PODXL | Podocalyxin-like protein 1 | IPI:IPI00299116.1 | EITIHTK | 0.47 | 0.82 | 0.57 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| POLR2A | DNA-directed RNA polymerase II subunit RPB1 | IPI:IPI00031627.3 | MDDDVFLRCIESNMLTDMTLQGI | 0.27 | | |
| POSTN | Isoform 1 of Periostin | IPI:IPI00007960.4 | DGHFTLFAPTNEAFEK | 3.19 | 5.78 | 0.55 |
| PPAN | Protein | IPI:IPI00853545.1 | RRWSTR | 0.17 | 0.36 | 0.46 |
| PPBP | Platelet basic protein | IPI:IPI00022445.1 | DSDLYAELR | 0.42 | 0.19 | 2.17 |
| PRDX2 | Peroxiredoxin-2 | IPI:IPI00027350.3 | IGKPAPDFK | 0.64 | | |
| PRDX2 | Peroxiredoxin-2 | IPI:IPI00027350.3 | QITVNDLPVGR | 0.47 | | |
| PROZ | Isoform 1 of Vitamin K-dependent protein Z | IPI:IPI00027843.1 | RAPDLQDLPWQVK | 0.21 | 0.33 | 0.63 |
| PSAT1 | Isoform 1 of Phosphoserine aminotransferase | IPI:IPI00001734.2 | FGTINIVHPK | | 0.30 | |
| PSMB2 | Proteasome subunit beta type-2 | IPI:IPI00028006.1 | NGYELSPTAAANFTR | | 0.15 | |
| PTCHD2 | Isoform 2 of Patched domain-containing protein 2 | IPI:IPI00002283.8 | ETPPLEDLAANQSEDPRNQRLSK | | 0.14 | |
| PTGDS | Prostaglandin-H2 D-isomerase | IPI:IPI00013179.1 | APEAQVSVQPNFQQDK | | 5.15 | |
| PVR | Isoform Beta of Poliovirus receptor | IPI:IPI00219425.3 | VLAKPQNTAEVQK | 0.09 | | |
| PZP | Pregnancy zone protein | IPI:IPI00025426.2 | AFQPFFVELTMPYSVIR | 7.72 | 0.32 | 24.32 |
| PZP | Pregnancy zone protein | IPI:IPI00025426.2 | ATVLNYLPK | 7.93 | 0.43 | 18.58 |
| PZP | Pregnancy zone protein | IPI:IPI00025426.2 | QGIPFFAQVLLVDGK | | 0.12 | |
| PZP | Pregnancy zone protein | IPI:IPI00025426.2 | VVVQTESGGR | | 0.08 | |
| QSOX1 | Isoform 1 of Sulfhydryl oxidase 1 | IPI:IPI00003590.2 | VLNTEANVVR | | 0.07 | |
| RBP4 | Plasma retinol-binding protein | IPI:IPI00022420.3 | FSGTWYAMAK | | 0.59 | |
| RBP4 | Plasma retinol-binding protein | IPI:IPI00022420.3 | LIVHNGYCDGR | | 0.29 | |
| RBP4 | Plasma retinol-binding protein | IPI:IPI00022420.3 | MKYWGVASFLQK | | 2.10 | |
| RELN | reelin isoform a | IPI:IPI00241562.4 | TSGITCIKPR | | 0.67 | |
| RERE | Isoform 1 of Arginine-glutamic acid dipeptide repeats protein | IPI:IPI00185027.4 | KVKEEASSPLK | | 0.12 | |
| SAA1; SAA2 | serum amyloid A2 | IPI:IPI00006146.4 | EANYIGSDK | 1.45 | 0.77 | 1.89 |
| SAA1; SAA2 | Serum amyloid A protein | IPI:IPI00552578.2 | EANYIGSDK | 1.45 | 0.77 | 1.89 |
| SAA1; SAA2 | serum amyloid A2 | IPI:IPI00006146.4 | EANYIGSDKYFHAR | 2.19 | 1.22 | 1.80 |
| SAA1; SAA2 | Serum amyloid A protein | IPI:IPI00552578.2 | EANYIGSDKYFHAR | 2.19 | 1.22 | 1.80 |
| SAA1; SAA2 | Serum amyloid A protein | IPI:IPI00552578.2 | FFGHGAEDSLADQAANEWGR | 4.65 | 1.07 | 4.34 |
| SAA1; SAA2 | serum amyloid A2 | IPI:IPI00006146.4 | FFSFLGEAFDGAR | 2.62 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| SAA1; SAA2 | Serum amyloid A protein | IPI:IPI00552578.2 | FFSFLGEAFDGAR | 2.62 | | |
| SAA1; SAA2 | Serum amyloid A protein | IPI:IPI00552578.2 | RGPGGVWAAEAISDAR | 4.82 | 4.49 | 1.07 |
| SAA1; SAA2 | serum amyloid A2 | IPI:IPI00006146.4 | RSFFSFLGEAFDGAR | 3.01 | 2.41 | 1.25 |
| SAA1; SAA2 | Serum amyloid A protein | IPI:IPI00552578.2 | RSFFSFLGEAFDGAR | 3.01 | 2.41 | 1.25 |
| SAA1; SAA2 | serum amyloid A2 | IPI:IPI00006146.4 | SFFSFLGEAFDGAR | 8.44 | 6.76 | 1.25 |
| SAA1; SAA2 | Serum amyloid A protein | IPI:IPI00552578.2 | SFFSFLGEAFDGAR | 8.44 | 6.76 | 1.25 |
| SAA1; SAA2 | Serum amyloid A protein | IPI:IPI00552578.2 | SGKDPNHFRPAGLPEKY | 5.36 | | |
| SAA4 | Serum amyloid A-4 protein | IPI:IPI00019399.1 | EALQGVGDMGR | 11.54 | 7.35 | 1.57 |
| SAA4 | Serum amyloid A-4 protein | IPI:IPI00019399.1 | VYLQGLIDYYLFGNSSTVLEDSK | 0.56 | 0.19 | 2.92 |
| SCML2 | Isoform 1 of Sex comb on midleg-like protein 2 | IPI:IPI00328688.3 | LDGSDNR | 0.32 | 0.69 | 0.46 |
| SELENBP1 | Selenium-binding protein 1 | IPI:IPI00012303.2 | HNVMISTEWAAPNVLR | 0.28 | 0.48 | 0.58 |
| SEMA7A | Semaphorin-7A | IPI:IPI00025257.1 | LQDVFLLPDPSGQWR | | 0.58 | |
| SEPP1 | Selenoprotein P | IPI:IPI00029061.2 | LPTDSELAPR | 1.51 | 2.10 | 0.72 |
| SERPINA1 | Isoform 1 of Alpha-1-antitrypsin | IPI:IPI00553177.1 | GKWERPFEVK | 56.93 | 25.11 | 2.27 |
| SERPINA1 | Isoform 1 of Alpha-1-antitrypsin | IPI:IPI00553177.1 | GTEAAGAMFLEAIPM | 17.00 | 7.28 | 2.33 |
| SERPINA1 | Isoform 1 of Alpha-1-antitrypsin | IPI:IPI00553177.1 | GTEAAGAMFLEAIPM | 0.42 | | |
| SERPINA1 | Isoform 1 of Alpha-1-antitrypsin | IPI:IPI00553177.1 | KLSSWVLLMK | 49.95 | 17.92 | 2.79 |
| SERPINA1 | Isoform 1 of Alpha-1-antitrypsin | IPI:IPI00553177.1 | KLSSWVLLMK | 2.15 | 0.89 | 2.42 |
| SERPINA1 | Isoform 1 of Alpha-1-antitrypsin | IPI:IPI00553177.1 | KQINDYVEKGTQGK | | 0.59 | |
| SERPINA1 | Isoform 1 of Alpha-1-antitrypsin | IPI:IPI00553177.1 | LAEFAFSLYR | 12.97 | 5.48 | 2.37 |
| SERPINA1 | Isoform 1 of Alpha-1-antitrypsin | IPI:IPI00553177.1 | LYHSEAFTVNFGDTEEAKKQINDYVEK | | 6.55 | |
| SERPINA1 | Isoform 1 of Alpha-1-antitrypsin | IPI:IPI00553177.1 | PFVFLMIEQNTK | 0.43 | | |
| SERPINA1 | Isoform 1 of Alpha-1-antitrypsin | IPI:IPI00553177.1 | TVNFGDTEEAKK | 1.01 | 1.16 | 0.86 |
| SERPINA10 | Protein Z-dependent protease inhibitor | IPI:IPI00007199.4 | NMEVFFPK | 0.27 | | |
| SERPINA3 | Alpha-1-antichymotrypsin | IPI:IPI00550991.3 | FEEGTEASAATAVK | 0.48 | | |
| SERPINA3 | Alpha-1-antichymotrypsin | IPI:IPI00550991.3 | IIVPTDTQNIFFMSK | 1.20 | 1.08 | 1.11 |
| SERPINA3 | Alpha-1-antichymotrypsin | IPI:IPI00550991.3 | PFDPQDTHQSR | 1.66 | 0.62 | 2.66 |
| SERPINA3 | Alpha-1-antichymotrypsin | IPI:IPI00550991.3 | WVMVPMMSLHHLTIPYFR | 0.44 | | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| SERPINA4 | Kallistatin | IPI:IPI00328609.3 | ATLDVDEAGTEAAAATSFAIK | 0.47 | 0.48 | 1.00 |
| SERPINA4 | Kallistatin | IPI:IPI00328609.3 | FYYLIASETPGK | 1.57 | 1.70 | 0.93 |
| SERPINA4 | Kallistatin | IPI:IPI00328609.3 | LGFTDLFSK | 3.25 | 5.05 | 0.64 |
| SERPINA4 | Kallistatin | IPI:IPI00328609.3 | WADLSGITK | 1.79 | 1.91 | 0.94 |
| SERPINA7 | Thyroxine-binding globulin | IPI:IPI00292946.1 | FAFNLYR | 7.38 | 10.02 | 0.74 |
| SERPINC1 | SERPINC1 protein | IPI:IPI00844156.2 | FATTFYQHLADSKNDNDNIFLSPLSISTAFAMTK | | 0.21 | |
| SERPINC1 | Antithrombin III variant | IPI:IPI00032179.2 | FATTFYQHLADSKNDNDNIFLSPLSISTAFAMTK | | 0.21 | |
| SERPINC1 | SERPINC1 protein | IPI:IPI00844156.2 | LVSANR | 5.73 | 8.06 | 0.71 |
| SERPINC1 | Antithrombin III variant | IPI:IPI00032179.2 | LVSANR | 5.73 | 8.06 | 0.71 |
| SERPINC1 | SERPINC1 protein | IPI:IPI00844156.2 | RVWELSK | 36.77 | 46.37 | 0.79 |
| SERPINC1 | Antithrombin III variant | IPI:IPI00032179.2 | RVWELSK | 36.77 | 46.37 | 0.79 |
| SERPINC1 | Antithrombin III variant | IPI:IPI00032179.2 | VAEGTQVLELPFKGDDITMVLILPKPEK | 0.59 | 1.01 | 0.58 |
| SERPIND1 | Serpin peptidase inhibitor, clade D (Heparin cofactor), member 1 | IPI:IPI00292950.4 | FAFNLYR | 7.38 | 10.02 | 0.74 |
| SERPIND1 | Serpin peptidase inhibitor, clade D (Heparin cofactor), member 1 | IPI:IPI00292950.4 | SVNDLYIQK | 9.13 | 12.01 | 0.76 |
| SERPINF1 | Pigment epithelium-derived factor | IPI:IPI00006114.4 | LQSLFDSPDFSK | 8.16 | 11.20 | 0.73 |
| SERPINF1 | Pigment epithelium-derived factor | IPI:IPI00006114.4 | TVQAVLTVPK | 5.46 | 7.34 | 0.74 |
| SERPINF1 | Pigment epithelium-derived factor | IPI:IPI00006114.4 | TVRVPMMSDPK | 0.27 | 0.48 | 0.57 |
| SERPINF2 | Alpha-2-antiplasmin | IPI:IPI00879231.1 | DFLQSLK | 0.81 | 1.36 | 0.60 |
| SERPINF2 | Alpha-2-antiplasmin | IPI:IPI00879231.1 | GDKLFGPDLK | 14.71 | 59.89 | 0.25 |
| SERPINF2 | Alpha-2-antiplasmin | IPI:IPI00879231.1 | IQEFLSGLPEDTVLLLNAIHFQGFWR | 1.79 | 2.33 | 0.77 |
| SERPING1 | Plasma protease C1 inhibitor | IPI:IPI00291866.5 | MEPFHFKNSVIKVPMMNSK | 0.32 | 0.62 | 0.52 |
| SERPING1 | Plasma protease C1 inhibitor | IPI:IPI00291866.5 | PVAHFIDQTLK | 0.70 | | |
| SERPING1 | Plasma protease C1 inhibitor | IPI:IPI00291866.5 | VATTVISK | 0.99 | 1.68 | 0.59 |
| SH3BGRL2 | SH3 domain-binding glutamic acid-rich-like protein 2 | IPI:IPI00412272.2 | ESNTVFSFLGLKPR | 0.89 | | |
| SH3BGRL3 | SH3 domain-binding glutamic acid-rich-like protein 3 | IPI:IPI00746352.1 | VYSTSVTGSR | 0.25 | 0.22 | 1.14 |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| SHBG | Isoform 1 of Sex hormone-binding globulin | IPI:IPI00023019.1 | IALGGLLFPASNLR | 0.81 | 1.62 | 0.50 |
| SHBG | Isoform 1 of Sex hormone-binding globulin | IPI:IPI00023019.1 | TSSSFEVR | 0.16 | 0.39 | 0.42 |
| SHBG | Isoform 1 of Sex hormone-binding globulin | IPI:IPI00023019.1 | VVLSSGSGPGLDLPLVLGLPLQLK | 0.41 | 0.97 | 0.42 |
| SLC14A2 | Urea transporter, kidney | IPI:IPI00177820.3 | ASIITK | 0.72 | 0.95 | 0.75 |
| SLC9A6 | Sodium/hydrogen exchanger 6 | IPI:IPI00022061.5 | LLNLGR | | 0.43 | |
| SMG7 | Breast cancer-associated antigen SGA-56M | IPI:IPI00871896.1 | MSFLGILCK | 0.16 | 0.14 | 1.17 |
| SVIL | Isoform 2 of Supervillin | IPI:IPI00018370.3 | RSRNTAVEQRLR | 0.50 | | |
| TAGLN2 | Transgelin-2 | IPI:IPI00550363.3 | DVGRPQPGRENFQNWLK | | 0.27 | |
| TAOK1 | Isoform 1 of Serine/threonine-protein kinase TAO1 | IPI:IPI00002232.2 | VSLRRALLEQK | 7.19 | 9.27 | 0.78 |
| TEGT | Bax inhibitor 1 | IPI:IPI00022748.4 | KLMMILAMNEKDK | | 0.25 | |
| TF | Serotransferrin | IPI:IPI00022463.1 | HQTVPQNTGGK | 1.02 | | |
| TF | Serotransferrin | IPI:IPI00022463.1 | SDNCEDTPEAGYFAVAVVKK | 1.38 | | |
| TF | Serotransferrin | IPI:IPI00022463.1 | YLGEEYVK | 4.05 | | |
| THBS1 | Thrombospondin-1 | IPI:IPI00296099.6 | DLASIAR | 0.57 | 5.76 | 0.10 |
| THBS1 | Thrombospondin-1 | IPI:IPI00296099.6 | FVFGTTPEDILR | 1.87 | 1.11 | 1.68 |
| THBS1 | Thrombospondin-1 | IPI:IPI00296099.6 | GTLLALERK | 0.58 | 0.95 | 0.61 |
| TIMP1 | Metalloproteinase inhibitor 1 | IPI:IPI00032292.1 | HLACLPR | 0.39 | 3.64 | 0.11 |
| TKT | Transketolase | IPI:IPI00643920.2 | MFGIDRDAIAQAVR | 0.73 | | |
| TLN1 | Talin-1 | IPI:IPI00298994.6 | ALSTDPAAPNLK | 2.29 | 0.50 | 4.58 |
| TLN1 | Talin-1 | IPI:IPI00298994.6 | AVASAAAALVLK | 0.91 | 0.36 | 2.56 |
| TLN1 | Talin-1 | IPI:IPI00298994.6 | LASEAKPAAVAAENEEIGSHIK | 0.91 | | |
| TLN1 | Talin-1 | IPI:IPI00298994.6 | VLVQNAAGSQEK | 0.64 | 0.29 | 2.24 |
| TLN1 | Talin-1 | IPI:IPI00298994.6 | VMVTNVTSLLK | 1.81 | 0.82 | 2.21 |
| TNC | Isoform 1 of Tenascin | IPI:IPI00031008.1 | KQSEPLEITLLAPER | 3.50 | 33.66 | 0.10 |
| TPM2 | Tropomyosin 2 | IPI:IPI00513698.1 | IQLVEEELDRAQER | 0.63 | 0.30 | 2.10 |
| TTR | Transthyretin | IPI:IPI00022432.1 | AADDTWEPFASGK | 84.06 | 151.87 | 0.55 |
| TTR | Transthyretin | IPI:IPI00022432.1 | ADDTWEPFASGK | 0.29 | 0.48 | 0.60 |
| UBA1 | Ubiquitin-like modifier-activating enzyme 1 | IPI:IPI00645078.1 | KPLLESGTLGTK | | 0.42 | |

TABLE S1-continued

Identified significant peptides

| GENE SYMBOL | Protein | Reference | Peptide | Ave HL positive (n = 22) | Ave HL negative (n = 14) | Ratio HL positive/ HL negative |
|---|---|---|---|---|---|---|
| UBE2L3 | Ubiquitin-conjugating enzyme E2 L3 | IPI:IPI00021347.1 | TDQVIQSLIALVNDPQPEHPLR | 34.09 | | |
| VASN | Vasorin | IPI:IPI00395488.2 | YLQGSSVQLR | | 0.21 | |
| VCL | Isoform 1 of Vinculin | IPI:IPI00291175.7 | AQQVSQGLDVLTAK | 0.81 | 0.38 | 2.14 |
| VCL | Isoform 1 of Vinculin | IPI:IPI00291175.7 | MSAEINEIIR | 0.33 | 0.55 | 0.60 |
| VNN1 | Pantetheinase | IPI:IPI00030871.2 | AFHYDMK | 0.63 | | |
| VTN | Vitronectin | IPI:IPI00298971.1 | GQYCYELDEK | | 0.32 | |
| VTN | Vitronectin | IPI:IPI00298971.1 | LIRDVWGIEGPIDAAFTR | | 0.74 | |
| VWF | von Willebrand factor | IPI:IPI00023014.1 | HIVTFDGQNFK | 1.08 | 0.70 | 1.55 |
| VWF | von Willebrand factor | IPI:IPI00023014.1 | VIVIPVGIGPHANLK | 0.92 | 0.62 | 1.50 |
| VWF | von Willebrand factor | IPI:IPI00023014.1 | YIILLLGK | 0.51 | | |
| YWHAB | Isoform Short of 14-3-3 protein beta/alpha | IPI:IPI00759832.1 | YDDMAAAMK | 0.25 | | |
| YWHAG | 14-3-3 protein gamma | IPI:IPI00220642.7 | YDDMAAAMK | 0.25 | | |

TABLE S2

Identified significant proteins

| GENE SYMBOL | Description | #peptides/ protein | Reference | Average HL positive | Average HL negative | Ratio HL positive/HL negative |
|---|---|---|---|---|---|---|
| A1BG | Alpha-1B-glycoprotein precursor | 27 | IPI: IPI00022895.7 | 23.54 | 24.48 | 0.96 |
| ACTA1 | Actin, alpha skeletal muscle | 19 | IPI: IPI00021428.1 | 3.34 | 6.23 | 0.54 |
| ACTB | Actin, cytoplasmic 1 | 25 | IPI: IPI00021439.1 | 4.79 | 4.32 | 1.11 |
| ACTN1 | Alpha-actinin-1 | 21 | IPI: IPI00013508.5 | 0.79 | 0.46 | 1.70 |
| AGT | Angiotensinogen precursor | 23 | IPI: IPI00032220.3 | 7.24 | 9.55 | 0.76 |
| AHSG | Alpha-2-HS-glycoprotein precursor | 11 | IPI: IPI00022431.1 | 27.46 | 16.07 | 1.71 |
| AMBP | AMBP protein precursor | 6 | IPI: IPI00022426.1 | 7.03 | 15.78 | 0.45 |
| ANPEP | Aminopeptidase N | 5 | IPI: IPI00221224.6 | 0.59 | 0.74 | 0.80 |
| APOA4 | Apolipoprotein A-IV precursor | 42 | IPI: IPI00304273.2 | 4.36 | 4.16 | 1.05 |
| APOB | Apolipoprotein B-100 precursor | 320 | IPI: IPI00022229.1 | 8.33 | 8.67 | 0.96 |
| APOC1 | Apolipoprotein C-I precursor | 6 | IPI: IPI00021855.1 | 1.75 | 0.35 | 5.04 |
| APOC2 | Apolipoprotein C-II precursor | 9 | IPI: IPI00021856.3 | 4.94 | 2.50 | 1.97 |
| APOC3 | Apolipoprotein C-III precursor | 9 | IPI: IPI00021857.1 | 3.58 | 2.86 | 1.25 |
| APOE | Apolipoprotein E precursor | 25 | IPI: IPI00021842.1 | 3.79 | 1.83 | 2.07 |
| APOF | apolipoprotein F precursor | 2 | IPI: IPI00299435.3 | 1.38 | 0.36 | 3.85 |
| APOH | Beta-2-glycoprotein 1 precursor | 7 | IPI: IPI00298828.3 | 17.52 | 14.91 | 1.18 |
| APOL1 | 42 kDa protein | 9 | IPI: IPI00852826.2 | 0.58 | 0.71 | 0.81 |
| APOM | Apolipoprotein M | 3 | IPI: IPI00030739.1 | 2.25 | 1.51 | 1.49 |
| ARHGDIB | Rho GDP-dissociation inhibitor 2 | 4 | IPI: IPI00003817.3 | 0.28 | 2.06 | 0.13 |
| ASL | Argininosuccinate lyase | 2 | IPI: IPI00220267.7 | 0.36 | 0.58 | 0.62 |
| AZGP1 | alpha-2-glycoprotein 1, zinc | 15 | IPI: IPI00166729.4 | 7.06 | 11.59 | 0.61 |
| B2M | Beta-2-microglobulin | 5 | IPI: IPI00868938.1 | 1.08 | 1.77 | 0.61 |
| BCHE | Cholinesterase precursor | 13 | IPI: IPI00025864.5 | 1.06 | 0.67 | 1.58 |
| BLVRB | Flavin reductase | 2 | IPI: IPI00783862.2 | 0.39 | 0.51 | 0.76 |
| BTD | biotinidase precursor | 8 | IPI: IPI00218413.2 | 0.67 | 0.88 | 0.77 |
| C1QA | Complement C1q subcomponent subunit A precursor | 3 | IPI: IPI00022392.1 | 1.03 | 1.17 | 0.88 |
| C1QB | complement component 1, q subcomponent, B chain precursor | 5 | IPI: IPI00477992.1 | 0.96 | 0.66 | 1.47 |
| C1R | Complement C1r subcomponent precursor | 13 | IPI: IPI00296165.5 | 1.02 | 0.90 | 1.13 |
| C1RL | Complement C1r-like protein | 9 | IPI: IPI00009793.3 | 0.32 | 0.40 | 0.80 |
| C1S | Complement C1s subcomponent precursor | 18 | IPI: IPI00017696.1 | 1.09 | 1.21 | 0.91 |
| C2 | Complement C2 precursor (Fragment) | 27 | IPI: IPI00303963.1 | 1.64 | 1.45 | 1.13 |
| C3 | Complement C3 precursor (Fragment) | 216 | IPI: IPI00783987.2 | 16.75 | 16.37 | 1.02 |
| C4A | Complement component 4A | 126 | IPI: IPI00643525.1 | 13.88 | 10.76 | 1.29 |
| C4B | C4B1 | 128 | IPI: IPI00418163.3 | 18.80 | 12.78 | 1.47 |

TABLE S2-continued

Identified significant proteins

| GENE SYMBOL | Description | #peptides/ protein | Reference | Average HL positive | Average HL negative | Ratio HL positive/HL negative |
|---|---|---|---|---|---|---|
| C4BPA | C4b-binding protein alpha chain precursor | 9 | IPI: IPI00021727.1 | 0.52 | 0.48 | 1.08 |
| C5 | Complement C5 precursor | 76 | IPI: IPI00032291.2 | 2.48 | 2.95 | 0.84 |
| C6 | Complement component 6 precursor | 25 | IPI: IPI00009920.2 | 1.08 | 1.29 | 0.84 |
| C7 | Complement component C7 precursor | 21 | IPI: IPI00296608.6 | 1.36 | 1.48 | 0.92 |
| C8A | Complement component C8 alpha chain precursor | 18 | IPI: IPI00011252.1 | 1.72 | 2.91 | 0.59 |
| C8B | Complement component C8 beta chain precursor | 18 | IPI: IPI00294395.1 | 2.12 | 1.95 | 1.09 |
| C9 | Complement component C9 precursor | 24 | IPI: IPI00022395.1 | 3.44 | 3.14 | 1.10 |
| CA1 | Carbonic anhydrase 1 | 6 | IPI: IPI00215983.3 | 1.32 | 1.21 | 1.09 |
| CD14 | Monocyte differentiation antigen CD14 precursor | 7 | IPI: IPI00029260.2 | 0.39 | 0.27 | 1.46 |
| CDH5 | Cadherin-5 precursor | 2 | IPI: IPI00012792.1 | 0.37 | 0.27 | 1.39 |
| CECR1 | Cat eye syndrome critical region protein 1 precursor | 2 | IPI: IPI00303071.4 | 5.31 | 0.63 | 8.40 |
| CFB | Isoform 1 of Complement factor B precursor (Fragment) | 43 | IPI: IPI00019591.1 | 10.49 | 9.81 | 1.07 |
| CFD | Complement factor D preproprotein | 4 | IPI: IPI00165972.3 | 0.28 | 1.40 | 0.20 |
| CFH | Isoform 1 of Complement factor H precursor | 28 | IPI: IPI00029739.5 | 4.04 | 4.34 | 0.93 |
| CFI | Complement factor I precursor | 13 | IPI: IPI00291867.3 | 2.04 | 2.55 | 0.80 |
| CFL1 | Cofilin-1 | 6 | IPI: IPI00012011.6 | 0.51 | 0.51 | 1.00 |
| CLEC3B | Tetranectin precursor | 6 | IPI: IPI00009028.1 | 1.26 | 1.01 | 1.26 |
| CNDP1 | Beta-Ala-His dipeptidase precursor | 21 | IPI: IPI00064667.4 | 0.44 | 0.44 | 1.00 |
| CNTN1 | Isoform 1 of Contactin-1 precursor | 2 | IPI: IPI00029751.1 | 1.15 | 0.49 | 2.36 |
| COL6A3 | alpha 3 type VI collagen isoform 1 precursor | 3 | IPI: IPI00022200.2 | 0.58 | 24.55 | 0.02 |
| CP | Ceruloplasmin precursor | 78 | IPI: IPI00017601.1 | 6.40 | 6.07 | 1.05 |
| CPB2 | Isoform 1 of Carboxypeptidase B2 precursor | 13 | IPI: IPI00329775.7 | 0.71 | 0.83 | 0.85 |
| CPN1 | Carboxypeptidase N catalytic chain precursor | 10 | IPI: IPI00010295.1 | 0.54 | 0.65 | 0.83 |
| CPN2 | similar to Carboxypeptidase N subunit 2 precursor | 14 | IPI: IPI00738433.1 | 1.43 | 1.60 | 0.89 |
| CRP | Isoform 1 of C-reactive protein precursor | 9 | IPI: IPI00022389.1 | 15.24 | 3.24 | 4.71 |
| CST3 | Cystatin-C precursor | 3 | IPI: IPI00032293.1 | 1.64 | 1.04 | 1.57 |
| ECM1 | Extracellular matrix protein 1 | 10 | IPI: IPI00645849.1 | 0.36 | 0.38 | 0.93 |
| EFEMP1 | Isoform 1 of EGF-containing fibulin-like extracellular matrix protein 1 precursor | 4 | IPI: IPI00029658.1 | 0.21 | 0.41 | 0.53 |
| F10 | Coagulation factor X precursor | 9 | IPI: IPI00019576.1 | 0.82 | 1.19 | 0.69 |
| F11 | Isoform 1 of Coagulation factor XI precursor | 8 | IPI: IPI00008556.1 | 0.24 | 0.26 | 0.93 |
| F2 | Prothrombin precursor (Fragment) | 20 | IPI: IPI00019568.1 | 6.98 | 6.10 | 1.14 |
| F5 | Coagulation factor V | 14 | IPI: IPI00022937.4 | 0.42 | 0.34 | 1.26 |
| FCGBP | IgGFc-binding protein precursor | 4 | IPI: IPI00242956.4 | 1.88 | 1.55 | 1.21 |
| FCN3 | Isoform 1 of Ficolin-3 precursor | 9 | IPI: IPI00293925.2 | 3.78 | 4.00 | 0.94 |
| FGA | Isoform 1 of Fibrinogen alpha chain precursor | 41 | IPI: IPI00021885.1 | 2.55 | 0.96 | 2.65 |
| FLNA | filamin A, alpha isoform 1 | 48 | IPI: IPI00302592.2 | 0.51 | 0.42 | 1.22 |
| FN1 | Isoform 1 of Fibronectin precursor | 19 | IPI: IPI00022418.1 | 0.37 | 0.40 | 0.93 |
| GAPDH | Glyceraldehyde-3-phosphate dehydrogenase | 7 | IPI: IPI00219018.7 | 0.93 | 1.06 | 0.88 |
| GC | Vitamin D-binding protein precursor | 32 | IPI: IPI00555812.4 | 13.45 | 10.90 | 1.23 |
| GGH | Gamma-glutamyl hydrolase precursor | 4 | IPI: IPI00023728.1 | 5.74 | 4.71 | 1.22 |
| GP1BA | platelet glycoprotein Ib alpha polypeptide precursor | 5 | IPI: IPI00748955.2 | 0.52 | 0.67 | 0.78 |
| GPLD1 | Isoform 1 of Phosphatidylinositol-glycan-specific phospholipase D precursor | 11 | IPI: IPI00299503.2 | 2.04 | 0.35 | 5.77 |
| GSN | Isoform 1 of Gelsolin precursor | 44 | IPI: IPI00026314.1 | 1.64 | 2.84 | 0.58 |
| HBA2 | Hemoglobin subunit alpha | 9 | IPI: IPI00410714.5 | 4.71 | 4.25 | 1.11 |
| HGFAC | Hepatocyte growth factor activator precursor | 5 | IPI: IPI00029193.1 | 0.42 | 0.42 | 1.01 |
| HPR | Isoform 1 of Haptoglobin-related protein precursor | 15 | IPI: IPI00477597.1 | 1.73 | 1.72 | 1.01 |
| HPX | Hemopexin precursor | 39 | IPI: IPI00022488.1 | 12.50 | 13.53 | 0.92 |
| HRG | Histidine-rich glycoprotein precursor | 21 | IPI: IPI00022371.1 | 7.89 | 9.94 | 0.79 |
| HSPA8 | Heat shock 70 kDa protein 8 isoform 2 variant (Fragment) | 7 | IPI: IPI00795040.1 | 0.50 | 0.52 | 0.98 |
| ICAM1 | Intercellular adhesion molecule 1 precursor | 3 | IPI: IPI00008494.4 | 0.80 | 0.62 | 1.28 |
| IGFALS | Insulin-like growth factor-binding protein complex acid labile chain precursor | 20 | IPI: IPI00020996.3 | 1.01 | 1.12 | 0.90 |
| IGFBP2 | Insulin-like growth factor-binding protein 2 precursor | 2 | IPI: IPI00297284.1 | 0.28 | 0.17 | 1.68 |
| IGFBP6 | Insulin-like growth factor-binding protein 6 precursor | 2 | IPI: IPI00029235.1 | 0.26 | 0.25 | 1.04 |
| ITIH1 | Inter-alpha-trypsin inhibitor heavy chain H1 precursor | 38 | IPI: IPI00292530.1 | 4.28 | 5.84 | 0.73 |
| ITIH2 | Inter-alpha-trypsin inhibitor heavy chain H2 precursor | 62 | IPI: IPI00305461.2 | 5.39 | 7.95 | 0.68 |

TABLE S2-continued

Identified significant proteins

| GENE SYMBOL | Description | #peptides/ protein | Reference | Average HL positive | Average HL negative | Ratio HL positive/HL negative |
|---|---|---|---|---|---|---|
| ITIH3 | Isoform 1 of Inter-alpha-trypsin inhibitor heavy chain H3 precursor | 28 | IPI: IPI00028413.8 | 1.91 | 2.41 | 0.79 |
| ITIH4 | Isoform 1 of Inter-alpha-trypsin inhibitor heavy chain H4 precursor | 53 | IPI: IPI00294193.4 | 8.60 | 8.89 | 0.97 |
| KLKB1 | Plasma kallikrein precursor | 16 | IPI: IPI00654888.4 | 1.73 | 1.99 | 0.87 |
| KNG1 | Kininogen-1 | 16 | IPI: IPI00032328.2 | 17.24 | 21.46 | 0.80 |
| KRT10 | Keratin, type I cytoskeletal 10 | 9 | IPI: IPI00009865.2 | 1.72 | 2.67 | 0.64 |
| KRT2 | Keratin, type II cytoskeletal 2 epidermal | 4 | IPI: IPI00021304.1 | 2.87 | 1.05 | 2.74 |
| LBP | Lipopolysaccharide-binding protein precursor | 8 | IPI: IPI00032311.4 | 0.54 | 0.42 | 1.29 |
| LCP1 | Plastin-2 | 7 | IPI: IPI00010471.5 | 0.31 | 0.25 | 1.24 |
| LDHB | L-lactate dehydrogenase B chain | 9 | IPI: IPI00219217.3 | 1.92 | 0.92 | 2.08 |
| LPA | Apolipoprotein | 11 | IPI: IPI00029168.1 | 0.44 | 0.61 | 0.72 |
| LRG1 | Leucine-rich alpha-2-glycoprotein precursor | 12 | IPI: IPI00022417.4 | 15.44 | 11.60 | 1.33 |
| LUM | Lumican precursor | 11 | IPI: IPI00020986.2 | 1.82 | 4.43 | 0.41 |
| MASP1 | mannan-binding lectin serine protease 1 isoform 2 precursor | 5 | IPI: IPI00290283.6 | 0.25 | 0.43 | 0.57 |
| MBL2 | Mannose-binding protein C precursor | 5 | IPI: IPI00004373.1 | 1.26 | 0.43 | 2.97 |
| MCAM | Isoform 1 of Cell surface glycoprotein MUC18 precursor | 2 | IPI: IPI00016334.2 | 2.49 | 1.39 | 1.79 |
| MSN | Moesin | 4 | IPI: IPI00219365.3 | 1.90 | 0.62 | 3.07 |
| MTMR15 | Isoform 1 of Coiled-coil domain-containing protein MTMR15 | 2 | IPI: IPI00007317.4 | 9.30 | 8.88 | 1.05 |
| PCYOX1 | Prenylcysteine oxidase 1 precursor | 2 | IPI: IPI00384280.5 | 0.19 | 0.21 | 0.90 |
| PDIA3 | Protein disulfide-isomerase A3 precursor | 4 | IPI: IPI00025252.1 | 0.27 | 0.40 | 0.68 |
| PFN1 | Profilin-1 | 9 | IPI: IPI00216691.5 | 1.12 | 1.38 | 0.81 |
| PGLYRP2 | Isoform 1 of N-acetylmuramoyl-L-alanine amidase precursor | 12 | IPI: IPI00163207.1 | 1.19 | 2.02 | 0.59 |
| PI16 | Isoform 1 of Peptidase inhibitor 16 precursor | 3 | IPI: IPI00301143.5 | 0.60 | 0.41 | 1.48 |
| PLEK | Pleckstrin | 5 | IPI: IPI00306311.8 | 0.53 | 0.52 | 1.01 |
| PNP | Purine nucleoside phosphorylase | 2 | IPI: IPI00871140.1 | 1.80 | 3.37 | 0.53 |
| PPBP | Platelet basic protein precursor | 5 | IPI: IPI00022445.1 | 0.62 | 0.38 | 1.63 |
| PRDX2 | Peroxiredoxin-2 | 4 | IPI: IPI00027350.3 | 0.54 | 0.71 | 0.77 |
| PROZ | Isoform 1 of Vitamin K-dependent protein Z precursor | 3 | IPI: IPI00027843.1 | 0.23 | 0.30 | 0.76 |
| PTGDS | Prostaglandin-H2 D-isomerase precursor | 3 | IPI: IPI00013179.1 | 0.28 | 4.34 | 0.06 |
| PVR | Isoform Beta of Poliovirus receptor precursor | 2 | IPI: IPI00219425.3 | 0.09 | 0.15 | 0.56 |
| PZP | Pregnancy zone protein precursor | 12 | IPI: IPI00025426.2 | 0.55 | 0.26 | 2.15 |
| QSOX1 | Isoform 1 of Sulfhydryl oxidase 1 precursor | 2 | IPI: IPI00003590.2 | 0.37 | 0.12 | 3.13 |
| RBP4 | Plasma retinol-binding protein precursor | 10 | IPI: IPI00022420.3 | 8.57 | 6.59 | 1.30 |
| RELN | reelin isoform a | 2 | IPI: IPI00241562.4 | 0.84 | 0.88 | 0.94 |
| SAA1 | serum amyloid A2 | 7 | IPI: IPI00006146.4 | 1.45 | 0.51 | 2.86 |
| SAA2 | Serum amyloid A protein precursor | 8 | IPI: IPI00552578.2 | 3.84 | 2.19 | 1.75 |
| SAA4 | Serum amyloid A-4 protein precursor | 8 | IPI: IPI00019399.1 | 1.20 | 0.93 | 1.29 |
| SELENBP1 | Selenium-binding protein 1 | 2 | IPI: IPI00012303.2 | 11.85 | 20.47 | 0.58 |
| SEMA7A | Semaphorin-7A precursor | 2 | IPI: IPI00025257.1 | 2.02 | 1.15 | 1.76 |
| SEPP1 | Selenoprotein P precursor | 3 | IPI: IPI00029061.2 | 0.56 | 0.83 | 0.67 |
| SERPINA10 | Protein Z-dependent protease inhibitor precursor | 9 | IPI: IPI00007199.4 | 0.33 | 0.29 | 1.14 |
| SERPINA3 | Alpha-1-antichymotrypsin precursor | 50 | IPI: IPI00550991.3 | 18.18 | 16.80 | 1.08 |
| SERPINA4 | Kallistatin precursor | 19 | IPI: IPI00328609.3 | 1.09 | 1.50 | 0.73 |
| SERPINA7 | Thyroxine-binding globulin precursor | 20 | IPI: IPI00292946.1 | 2.09 | 1.89 | 1.11 |
| SERPINC1 | Antithrombin III variant | 49 | IPI: IPI00032179.2 | 7.26 | 7.87 | 0.92 |
| SERPINC1 | SERPINC1 protein | 27 | IPI: IPI00844156.2 | 4.65 | 4.06 | 1.14 |
| SERPIND1 | Serpin peptidase inhibitor, clade D (Heparin cofactor), member 1 | 22 | IPI: IPI00292950.4 | 5.63 | 5.30 | 1.06 |
| SERPINF1 | Pigment epithelium-derived factor precursor | 27 | IPI: IPI00006114.4 | 2.07 | 2.83 | 0.73 |
| SERPINF2 | Alpha-2-antiplasmin precursor | 24 | IPI: IPI00879231.1 | 6.34 | 6.17 | 1.03 |
| SERPING1 | Plasma protease C1 inhibitor precursor | 42 | IPI: IPI00291866.5 | 7.43 | 10.58 | 0.70 |
| SHBG | Isoform 1 of Sex hormone-binding globulin precursor | 10 | IPI: IPI00023019.1 | 0.33 | 0.42 | 0.78 |
| TAGLN2 | Transgelin-2 | 6 | IPI: IPI00550363.3 | 0.42 | 0.31 | 1.36 |
| THBS1 | Thrombospondin-1 precursor | 18 | IPI: IPI00296099.6 | 0.49 | 0.37 | 1.31 |
| TIMP1 | Metalloproteinase inhibitor 1 precursor | 2 | IPI: IPI00032292.1 | 0.74 | 3.51 | 0.21 |
| TLN1 | Talin-1 | 40 | IPI: IPI00298994.6 | 0.83 | 0.39 | 2.15 |
| TNC | Isoform 1 of Tenascin precursor | 3 | IPI: IPI00031008.1 | 0.91 | 0.94 | 0.97 |
| TPM2 | Tropomyosin 2 | 4 | IPI: IPI00513698.1 | 0.37 | 0.32 | 1.17 |
| TTR | Transthyretin precursor | 19 | IPI: IPI00022432.1 | 6.96 | 9.74 | 0.71 |
| VASN | Vasorin precursor | 3 | IPI: IPI00395488.2 | 0.25 | 0.32 | 0.77 |
| VCL | Isoform 1 of Vinculin | 20 | IPI: IPI00291175.7 | 0.35 | 0.25 | 1.40 |
| VTN | Vitronectin precursor | 15 | IPI: IPI00298971.1 | 9.92 | 10.69 | 0.93 |
| VWF | von Willebrand factor precursor | 25 | IPI: IPI00023014.1 | 1.34 | 1.09 | 1.22 |

TABLE S2-continued

Identified significant proteins

| GENE SYMBOL | Description | #peptides/ protein | Reference | Average HL positive | Average HL negative | Ratio HL positive/HL negative |
|---|---|---|---|---|---|---|
| YWHAB | Isoform Short of 14-3-3 protein beta/alpha | 4 | IPI: IPI00759832.1 | 0.28 | 0.23 | 1.22 |
| YWHAG | 14-3-3 protein gamma | 4 | IPI: IPI00220642.7 | 0.37 | 0.63 | 0.59 |

TABLE S3

Significantly altered proteins and related biological functions. Peptides were initially identified by mass spectrometry. Selected biological functions and expression sites associated with the individual proteins were identified by Ingenuity Pathway Analysis (IPA).

| Protein | Gene Symbol | #pept/ protein | Ratio$^a$ | Biological Function | Expressed$^b$ in Liver | WBC$^c$ |
|---|---|---|---|---|---|---|
| 14-3-3 protein gamma | YWHAG | 4 | 0.59 | Cancer | | X |
| Actin, alpha skeletal muscle | ACTA1 | 19 | 0.54 | | X | X |
| Alpha 3 type VI collagen | COL6A3 | 3 | 0.02 | Cancer | X | X |
| Alpha-2-glycoprotein 1, zinc | AZGP1 | 15 | 0.61 | Cancer | | |
| Alpha-2-HS-glycoprotein | AHSG | 11 | 1.71 | IR$^d$, Cancer | X | |
| Alpha-actinin-1 | ACTN1 | 21 | 1.70 | | | X |
| AMBP protein | AMBP | 6 | 0.45 | IR, Cancer | X | |
| Apolipoprotein | LPA | 11 | 0.70 | | | |
| Apolipoprotein C-I | APOC1 | 6 | 5.04 | Cancer | X | X |
| Apolipoprotein C-II | APOC2 | 9 | 1.97 | | | |
| Apolipoprotein E | APOE | 25 | 2.07 | IR, Cancer | X | |
| apolipoprotein F | APOF | 2 | 3.85 | Cancer | X | |
| Apolipoprotein M | APOM | 3 | 1.50 | | X | |
| Argininosuccinate lyase | ASL | 2 | 0.62 | | X | |
| Beta-2-microglobulin | B2M | 5 | 0.61 | IR, Cancer | X | X |
| C4B1 | C4B | 128 | 1.50 | IR, Cancer | X | |
| Cat eye syndrome critical region protein 1 | CECR1 | 2 | 8.40 | | | |
| Cell surface glycoprotein MUC18 | MCAM | 2 | 1.79 | IR, Cancer | | |
| Cholinesterase | BCHE | 13 | 1.58 | | | |
| Coagulation factor X | F10 | 9 | 0.69 | | X | |
| Complement component 4A | C4A | 126 | 1.29 | IR, Cancer | X | |
| Complement component C8 alpha chain | C8A | 18 | 0.59 | IR | X | |
| Complement factor D preproprotein | CFD | 4 | 0.20 | IR, Cancer | X | |
| Contactin-1 | CNTN1 | 2 | 2.36 | | | |
| C-reactive protein | CRP | 9 | 4.71 | IR, Cancer | X | |
| Cystatin-C | CST3 | 3 | 1.57 | Cancer | | X |
| EGF-containing fibulin-like extracellular matrix protein 1 | EFEMP1 | 4 | 0.53 | Cancer | X | |
| Gelsolin | GSN | 44 | 0.58 | IR, Cancer | | |
| Insulin-like growth factor-binding protein 2 | IGFBP2 | 2 | 1.68 | Cancer | X | X |
| Inter-alpha-trypsin inhibitor heavy chain H1 | ITIH1 | 38 | 0.70 | | X | |
| Inter-alpha-trypsin inhibitor heavy chain H2 | ITIH2 | 62 | 0.70 | | X | |
| Phosphatidylinositol-glycan-specific phospholipase D | GPLD1 | 11 | 5.77 | | X | |
| Sulfhydryl oxidase 1 | QSOX1 | 2 | 3.13 | | | X |
| Kallistatin | SERPINA4 | 19 | 0.70 | | | |
| Keratin, type I cytoskeletal 10 | KRT10 | 9 | 0.64 | | X | X |
| Keratin, type II cytoskeletal 2 epidermal | KRT2 | 4 | 2.74 | | | |
| L-lactate dehydrogenase B chain | LDHB | 9 | 2.08 | | | X |
| Lumican | LUM | 11 | 0.41 | IR | | X |
| Mannan-binding lectin serine protease 1 | MASP1 | 5 | 0.57 | IR, Cancer | X | |
| Mannose-binding protein C | MBL2 | 5 | 2.97 | IR | | |
| Metalloproteinase inhibitor 1 | TIMP1 | 2 | 0.21 | IR, Cancer | X | X |
| Moesin | MSN | 4 | 3.07 | IR | | X |

TABLE S3-continued

Significantly altered proteins and related biological functions. Peptides were initially identified by mass spectrometry. Selected biological functions and expression sites associated with the individual proteins were identified by Ingenuity Pathway Analysis (IPA).

| Protein | Gene Symbol | #pept/ protein | Ratio[a] | Biological Function | Expressed[b] in Liver | WBC[c] |
|---|---|---|---|---|---|---|
| Monocyte differentiation antigen CD14 | CD14 | 7 | 1.5 | IR, Cancer | | X |
| Peptidase inhibitor 16 | PI16 | 3 | 1.50 | | | X |
| Pigment epithelium-derived factor | SERPINF1 | 27 | 0.70 | | | X |
| Plasma protease C1 inhibitor | SERPING1 | 42 | 0.70 | | X | X |
| Platelet basic protein | PPBP | 5 | 1.63 | IR | | X |
| Poliovirus receptor | PVR | 2 | 0.56 | IR | | X |
| Pregnancy zone protein | PZP | 12 | 2.15 | | | |
| Prostaglandin-H2 D-isomerase | PTGDS | 3 | 0.06 | IR, Cancer | X | |
| Protein disulfide-isomerase A3 | PDIA3 | 4 | 0.68 | | | X |
| Purine nucleoside phosphorylase | PNP | 2 | 0.53 | IR, Cancer | | X |
| Rho GDP-dissociation inhibitor 2 | ARHGDIB | 4 | 0.13 | IR, Cancer | X | X |
| Selenium-binding protein 1 | SELENBP1 | 2 | 0.58 | Cancer | | |
| Selenoprotein P | SEPP1 | 3 | 0.70 | | X | X |
| Semaphorin-7A/CD108 | SEMA7A | 2 | 1.76 | IR | | X |
| Serum amyloid A | SAA2 | 8 | 1.75 | | X | X |
| Serum amyloid A2 | SAA1 | 7 | 2.86 | IR, Cancer | X | X |
| Talin-1 | TLN1 | 40 | 2.15 | | | X |
| Transthyretin | TTR | 19 | 0.70 | | X | |

[a]Ratio of the protein concentrations from HIV-infected patients with HL versus HIV-infected patients without HL.
[b]An "X" indicates that IPA lists these tissues or cell types as a known source of these proteins. There are commonly other tissues or cellular sources for these proteins that are not included in this table.
[c]WBC, white blood cells.
[d]IR, inflammatory response.

---

We claim:

1. A method consisting of:
   measuring the level of all proteins listed in Table S3 in a plasma sample from a person; and
   comparing the level of the proteins in the plasma sample with the level of the proteins in a normal or healthy subject.

2. The method of claim 1, wherein the person has lymphoma.

3. The method of claim 1, wherein the person has Hodgkin's lymphoma or non-Hodgkin's lymphoma.

4. The method of claim 1, wherein the measuring comprises contacting the plasma sample with a reagent that reacts with proteins in the plasma sample to detect the presence of the proteins listed in Table S3.

5. The method of claim 4, wherein the reagent is an antibody.

6. The method of claim 3, wherein the person is infected with human immunodeficiency virus (HIV).

7. The method of claim 1, wherein measuring the level of all proteins listed in Table S3 comprises analyzing the plasma sample with mass spectrometry.

8. The method of claim 1, wherein comparing the level of the proteins in the plasma sample to the normal or healthy subject comprises determining if the level of all of the proteins listed in Table S3 in the plasma sample differ by at least 1.5 fold in comparison to the level of all of the proteins listed in Table S3 in the normal or healthy subject.

* * * * *